US012662669B2

(12) United States Patent
Mueller et al.

(10) Patent No.: US 12,662,669 B2
(45) Date of Patent: *Jun. 23, 2026

(54) RAAV-BASED COMPOSITIONS AND METHODS FOR TREATING AMYOTROPHIC LATERAL SCLEROSIS

(71) Applicant: University of Massachusetts, Westborough, MA (US)

(72) Inventors: Christian Mueller, Worcester, MA (US); Robert H. Brown, Jr., Worcester, MA (US)

(73) Assignee: University of Massachusetts, Westborough, MA (US)

( * ) Notice: Subject to any disclaimer, the term of this patent is extended or adjusted under 35 U.S.C. 154(b) by 156 days.

This patent is subject to a terminal disclaimer.

(21) Appl. No.: 18/362,190

(22) Filed: Jul. 31, 2023

(65) Prior Publication Data
US 2024/0076668 A1      Mar. 7, 2024

Related U.S. Application Data

(60) Division of application No. 17/174,452, filed on Feb. 12, 2021, now Pat. No. 11,760,999, which is a continuation of application No. 16/295,621, filed on Mar. 7, 2019, now Pat. No. 10,954,518, which is a continuation of application No. 15/126,688, filed as application No. PCT/US2015/021321 on Mar. 18, 2015, now Pat. No. 10,280,418.

(60) Provisional application No. 61/955,189, filed on Mar. 18, 2014.

(51) Int. Cl.
| | |
|---|---|
| *C12N 15/113* | (2010.01) |
| *C12N 15/11* | (2006.01) |
| *C12N 15/86* | (2006.01) |

(52) U.S. Cl.
CPC .......... *C12N 15/113* (2013.01); *C12N 15/111* (2013.01); *C12N 15/1137* (2013.01); *C12N 15/86* (2013.01); *C12Y 115/01001* (2013.01); *C12N 2310/14* (2013.01); *C12N 2310/141* (2013.01); *C12N 2320/32* (2013.01); *C12N 2330/51* (2013.01); *C12N 2750/14143* (2013.01)

(58) Field of Classification Search
CPC ..... C12N 15/113; C12N 15/111; C12N 15/86; C12N 2310/14; C12N 2310/141; C12N 2320/32; C12N 2750/14143; C12Y 115/01001
See application file for complete search history.

(56) References Cited

U.S. PATENT DOCUMENTS

| | | | |
|---|---|---|---|
| 5,478,745 | A | 12/1995 | Samulski et al. |
| 5,871,982 | A | 2/1999 | Wilson et al. |
| 6,001,650 | A | 12/1999 | Colosi |
| 6,156,303 | A | 12/2000 | Russell et al. |
| 6,177,403 | B1 | 1/2001 | Stedman |
| 6,251,677 | B1 | 6/2001 | Wilson et al. |
| 6,485,966 | B2 | 11/2002 | Gao et al. |
| 6,544,786 | B1 | 4/2003 | Xiao et al. |
| 6,953,690 | B1 | 10/2005 | Gao et al. |
| 7,022,519 | B2 | 4/2006 | Gao et al. |
| 7,132,530 | B2 | 11/2006 | Bennett et al. |
| 7,198,951 | B2 | 4/2007 | Gao et al. |
| 7,235,393 | B2 | 6/2007 | Gao et al. |
| 7,387,896 | B2 | 6/2008 | Turner et al. |
| 7,427,396 | B2 | 9/2008 | Arbetman et al. |
| 7,456,015 | B2 | 11/2008 | Bohn et al. |
| 7,498,316 | B2 | 3/2009 | Xu et al. |
| 7,622,455 | B2 | 11/2009 | Bennett et al. |
| 7,678,895 | B2 | 3/2010 | Bennett et al. |
| 7,691,995 | B2 | 4/2010 | Zamore et al. |
| 7,750,144 | B2 | 7/2010 | Zamore et al. |
| 7,772,203 | B2 | 8/2010 | Zamore et al. |
| 7,892,793 | B2 | 2/2011 | Xu |
| 7,902,163 | B2 | 3/2011 | Bennett et al. |
| 7,906,111 | B2 | 3/2011 | Wilson et al. |
| 8,008,271 | B2 | 8/2011 | Xu et al. |
| 8,202,846 | B2 | 6/2012 | Hannon et al. |
| 8,222,221 | B2 | 7/2012 | Corey et al. |
| 8,309,533 | B2 | 11/2012 | Xu |
| 8,524,446 | B2 | 9/2013 | Gao et al. |
| 8,729,036 | B2 | 5/2014 | Zamore et al. |
| 8,734,809 | B2 | 5/2014 | Gao et al. |
| 8,993,529 | B2 | 3/2015 | Bennett et al. |
| 9,102,949 | B2 | 8/2015 | Gao et al. |
| 9,121,018 | B2 | 9/2015 | Zamore et al. |
| 9,193,753 | B2 | 11/2015 | Tuschl et al. |
| 9,217,155 | B2 | 12/2015 | Gao et al. |
| 9,226,976 | B2 | 1/2016 | Flotte et al. |

(Continued)

FOREIGN PATENT DOCUMENTS

| | | |
|---|---|---|
| JP | 2011-511636 A | 4/2011 |
| JP | 2017-510298 A | 4/2017 |

(Continued)

OTHER PUBLICATIONS

McMenamin et al. ("Progress and prospects: Immunobiology of gene therapy for neurodegenerative disease: prospects and risks." Gene Therapy 17.4 (2010): 448-458).*

(Continued)

*Primary Examiner* — Kimberly Chong

(74) *Attorney, Agent, or Firm* — Wolf, Greenfield & Sacks, P.C.

(57) ABSTRACT

The invention relates to inhibitory nucleic acids and rAAV-based compositions, methods and kits useful for treating Amyotrophic Lateral Sclerosis.

20 Claims, 22 Drawing Sheets

Specification includes a Sequence Listing.

(56) References Cited

U.S. PATENT DOCUMENTS

| | | | |
|---|---|---|---|
| 9,249,424 | B2 | 2/2016 | Wolf et al. |
| 9,272,053 | B2 | 3/2016 | Gao et al. |
| 9,284,357 | B2 | 3/2016 | Gao et al. |
| 9,546,369 | B2 | 1/2017 | Gao et al. |
| 9,596,835 | B2 | 3/2017 | Gao et al. |
| 9,611,472 | B2 | 4/2017 | Zamore et al. |
| 9,701,984 | B2 | 7/2017 | Gao et al. |
| 9,725,719 | B2* | 8/2017 | Kaspar .................. A61P 43/00 |
| 9,850,487 | B2 | 12/2017 | Zamore et al. |
| 9,879,253 | B2 | 1/2018 | Zamore et al. |
| 9,885,057 | B2 | 2/2018 | Flotte et al. |
| 10,072,251 | B2 | 9/2018 | Gao et al. |
| 10,077,452 | B2 | 9/2018 | Flotte et al. |
| 10,166,297 | B2 | 1/2019 | Gao et al. |
| 10,280,418 | B2 | 5/2019 | Mueller et al. |
| 10,300,146 | B2 | 5/2019 | Gao et al. |
| 10,370,432 | B2 | 8/2019 | Esteves et al. |
| 10,597,656 | B2 | 3/2020 | Flotte et al. |
| 10,711,274 | B2 | 7/2020 | Mueller et al. |
| 10,781,453 | B2 | 9/2020 | Heslin et al. |
| 10,793,861 | B2 | 10/2020 | Kaspar et al. |
| 10,954,518 | B2 | 3/2021 | Mueller et al. |
| 11,739,330 | B2 | 8/2023 | Mueller et al. |
| 11,760,999 | B2 | 9/2023 | Mueller et al. |
| 11,859,179 | B2 | 1/2024 | Mueller et al. |
| 12,312,587 | B2 | 5/2025 | Mueller et al. |
| 12,529,051 | B2 | 1/2026 | Mueller et al. |
| 2001/0016355 | A1 | 8/2001 | Samulski et al. |
| 2002/0164783 | A1 | 11/2002 | Feldhaus |
| 2002/0192823 | A1 | 12/2002 | Bartlett |
| 2003/0103939 | A1 | 6/2003 | Engelhardt et al. |
| 2003/0110526 | A1 | 6/2003 | Brown et al. |
| 2003/0138772 | A1 | 7/2003 | Gao et al. |
| 2004/0101514 | A1 | 5/2004 | Liu et al. |
| 2004/0219528 | A1 | 11/2004 | Morris et al. |
| 2005/0014262 | A1 | 1/2005 | Gao et al. |
| 2005/0019915 | A1 | 1/2005 | Bennett et al. |
| 2005/0032219 | A1 | 2/2005 | Aubourg et al. |
| 2005/0037988 | A1 | 2/2005 | Zamore et al. |
| 2005/0137153 | A1 | 6/2005 | McSwiggen et al. |
| 2005/0197313 | A1 | 9/2005 | Roelvink et al. |
| 2005/0255086 | A1 | 11/2005 | Davidson et al. |
| 2005/0255089 | A1 | 11/2005 | Chiorini et al. |
| 2005/0255487 | A1 | 11/2005 | Khvorova et al. |
| 2005/0261218 | A1 | 11/2005 | Esau et al. |
| 2005/0287122 | A1 | 12/2005 | Bartlett et al. |
| 2005/0288243 | A1 | 12/2005 | Xu et al. |
| 2006/0063174 | A1 | 3/2006 | Turner et al. |
| 2006/0093589 | A1 | 5/2006 | Warrington et al. |
| 2006/0153826 | A1 | 7/2006 | Arnould et al. |
| 2006/0189564 | A1 | 8/2006 | Burright et al. |
| 2006/0228800 | A1 | 10/2006 | Lin et al. |
| 2006/0229268 | A1 | 10/2006 | Benjamin et al. |
| 2006/0292117 | A1 | 12/2006 | Loiler et al. |
| 2007/0036760 | A1 | 2/2007 | Wilson et al. |
| 2007/0243526 | A1 | 10/2007 | Kay et al. |
| 2007/0253936 | A1 | 11/2007 | Kay et al. |
| 2007/0292410 | A1 | 12/2007 | Cashman et al. |
| 2008/0200420 | A1 | 8/2008 | Zamore et al. |
| 2009/0042828 | A1 | 2/2009 | Xu et al. |
| 2009/0111766 | A1 | 4/2009 | Atkinson et al. |
| 2009/0149409 | A1 | 6/2009 | Bohn et al. |
| 2009/0197338 | A1 | 8/2009 | Vandenberghe et al. |
| 2009/0215879 | A1 | 8/2009 | DiPrimio et al. |
| 2009/0239240 | A1 | 9/2009 | Chu |
| 2010/0186103 | A1 | 7/2010 | Gao et al. |
| 2010/0323001 | A1 | 12/2010 | Pachuk |
| 2011/0039914 | A1 | 2/2011 | Pavco et al. |
| 2011/0171262 | A1 | 7/2011 | Bakker et al. |
| 2011/0172293 | A1 | 7/2011 | Fish et al. |
| 2011/0212520 | A1 | 9/2011 | Davidson et al. |
| 2011/0258716 | A1 | 10/2011 | Baltimore et al. |
| 2012/0077870 | A1 | 3/2012 | Blanks et al. |
| 2012/0137379 | A1 | 5/2012 | Gao et al. |
| 2012/0270930 | A1 | 10/2012 | Van Der Maarel et al. |

| | | | |
|---|---|---|---|
| 2012/0309050 | A1 | 12/2012 | Kumon et al. |
| 2013/0030042 | A1 | 1/2013 | Couto |
| 2013/0101558 | A1 | 4/2013 | Gao et al. |
| 2013/0109742 | A1 | 5/2013 | Hewitt et al. |
| 2013/0142861 | A1 | 6/2013 | Tsou et al. |
| 2013/0195801 | A1 | 8/2013 | Gao et al. |
| 2013/0281516 | A1 | 10/2013 | Gao et al. |
| 2014/0142161 | A1 | 5/2014 | Flotte et al. |
| 2014/0142288 | A1 | 5/2014 | Davidson et al. |
| 2014/0147418 | A1 | 5/2014 | Chiorini et al. |
| 2014/0179770 | A1 | 6/2014 | Zhang et al. |
| 2014/0201857 | A1 | 7/2014 | Fahrenkrug et al. |
| 2014/0296486 | A1 | 10/2014 | Gao et al. |
| 2014/0335054 | A1 | 11/2014 | Gao et al. |
| 2015/0065560 | A1 | 3/2015 | Bjorklund et al. |
| 2015/0252421 | A1 | 9/2015 | Pickering-Brown et al. |
| 2015/0258180 | A1 | 9/2015 | Mahuran et al. |
| 2015/0259679 | A1 | 9/2015 | Bennett et al. |
| 2016/0017005 | A1 | 1/2016 | Asokan et al. |
| 2016/0024496 | A1 | 1/2016 | Bennett et al. |
| 2016/0060624 | A1 | 3/2016 | Davidson et al. |
| 2016/0076054 | A1 | 3/2016 | Auricchio et al. |
| 2016/0135438 | A1 | 5/2016 | Gao et al. |
| 2016/0153005 | A1 | 6/2016 | Zhang et al. |
| 2016/0185832 | A1 | 6/2016 | Drivas et al. |
| 2016/0186211 | A1 | 6/2016 | Flotte et al. |
| 2016/0194374 | A1 | 7/2016 | Wijnholds et al. |
| 2016/0208257 | A1 | 7/2016 | Gao et al. |
| 2016/0230172 | A1 | 8/2016 | Rigo |
| 2016/0251655 | A1 | 9/2016 | Freier et al. |
| 2016/0272976 | A1 | 9/2016 | Kaspar |
| 2016/0326524 | A1 | 11/2016 | Flotte et al. |
| 2017/0029785 | A1 | 2/2017 | Zhao et al. |
| 2017/0101645 | A1 | 4/2017 | Brown et al. |
| 2017/0114340 | A1 | 4/2017 | Mueller et al. |
| 2017/0145439 | A1 | 5/2017 | Gao et al. |
| 2017/0152517 | A1 | 6/2017 | Barkats et al. |
| 2017/0159071 | A9 | 6/2017 | Flotte et al. |
| 2017/0165377 | A1 | 6/2017 | Gao et al. |
| 2017/0166927 | A1 | 6/2017 | Gao et al. |
| 2017/0191039 | A1 | 7/2017 | Gao et al. |
| 2017/0349911 | A1 | 12/2017 | Gao et al. |
| 2018/0094267 | A1 | 4/2018 | Heslin et al. |
| 2018/0140810 | A1 | 5/2018 | Cataltepe et al. |
| 2018/0214576 | A1 | 8/2018 | Fitzgerald et al. |
| 2018/0265571 | A1 | 9/2018 | Esteves et al. |
| 2018/0265863 | A1 | 9/2018 | Esteves et al. |
| 2018/0265865 | A2 | 9/2018 | Flotte et al. |
| 2018/0298380 | A1 | 10/2018 | Gao et al. |
| 2018/0311290 | A1 | 11/2018 | Sena-Esteves et al. |
| 2019/0211327 | A1 | 7/2019 | Flotte et al. |
| 2019/0276826 | A1 | 9/2019 | Mueller et al. |
| 2019/0282709 | A1 | 9/2019 | Gao et al. |
| 2019/0316126 | A1 | 10/2019 | Mueller et al. |
| 2020/0032256 | A1 | 1/2020 | Mueller et al. |
| 2020/0248187 | A1 | 8/2020 | Mueller et al. |
| 2020/0354716 | A1 | 11/2020 | Mueller et al. |
| 2021/0246450 | A1 | 8/2021 | Mueller et al. |
| 2023/0416757 | A1 | 12/2023 | Mueller et al. |
| 2024/0167025 | A1 | 5/2024 | Mueller et al. |

FOREIGN PATENT DOCUMENTS

| | | | |
|---|---|---|---|
| JP | 2018-538002 A | | 12/2018 |
| WO | WO 2003/006477 A1 | | 1/2003 |
| WO | WO 2003/042397 A2 | | 5/2003 |
| WO | WO 2005/033321 A2 | | 4/2005 |
| WO | WO 2005/062937 A2 | | 7/2005 |
| WO | WO 2005/116204 A1 | | 12/2005 |
| WO | WO 2006/031267 A2 | | 3/2006 |
| WO | WO 2006/066066 A2 | | 6/2006 |
| WO | WO 2006/119432 A2 | | 11/2006 |
| WO | WO 2007/000668 A2 | | 1/2007 |
| WO | WO 2007/027775 A2 | | 3/2007 |
| WO | WO 2008/091703 A2 | | 7/2008 |
| WO | WO 2008/125846 A2 | | 10/2008 |
| WO | WO 2008/147839 A1 | | 12/2008 |
| WO | WO 2008/150897 A2 | | 12/2008 |
| WO | WO 2009/102427 A2 | | 8/2009 |

(56) References Cited

FOREIGN PATENT DOCUMENTS

| WO | WO 2009/109665 A1 | 9/2009 |
|----|----|----|
| WO | WO 2009/146178 A1 | 12/2009 |
| WO | WO 2010/027446 A2 | 3/2010 |
| WO | WO 2010/034314 A1 | 4/2010 |
| WO | WO 2010/071454 A1 | 6/2010 |
| WO | WO 2010/099383 A2 | 9/2010 |
| WO | WO 2010/129021 A1 | 11/2010 |
| WO | WO 2010/138263 A2 | 12/2010 |
| WO | WO 2011/094198 A1 | 8/2011 |
| WO | WO 2011/133890 A1 | 10/2011 |
| WO | WO 2011/135396 A1 | 11/2011 |
| WO | WO 2013/055865 A1 | 4/2013 |
| WO | WO 2013/123503 A1 | 8/2013 |
| WO | WO 2013/170078 A1 | 11/2013 |
| WO | WO 2013/190059 A1 | 12/2013 |
| WO | WO 2014/062691 A2 | 4/2014 |
| WO | WO 2014/114303 A1 | 7/2014 |
| WO | WO 2014/160092 A1 | 10/2014 |
| WO | WO 2014/186746 A1 | 11/2014 |
| WO | WO 2014/197748 A2 | 12/2014 |
| WO | WO 2015/031392 A1 | 3/2015 |
| WO | WO 2015/054676 A2 | 4/2015 |
| WO | WO 2015/057727 A1 | 4/2015 |
| WO | WO 2015/089354 A1 | 6/2015 |
| WO | WO 2015/121501 A1 | 8/2015 |
| WO | WO 2015/143078 A1 | 9/2015 |
| WO | WO 2015/164786 A1 | 10/2015 |
| WO | WO 2015/168666 A2 | 11/2015 |
| WO | WO 2015/195621 A1 | 12/2015 |
| WO | WO 2016/065001 A1 | 4/2016 |
| WO | WO 2016/112132 A1 | 7/2016 |
| WO | WO 2016/167780 A1 | 10/2016 |
| WO | WO 2016/174056 A1 | 11/2016 |
| WO | WO 2016/186772 A2 | 11/2016 |
| WO | WO 2016/187053 A1 | 11/2016 |
| WO | WO 2016/210372 A2 | 12/2016 |
| WO | WO 2017/023724 A1 | 2/2017 |
| WO | WO 2017/109757 A1 | 6/2017 |
| WO | WO 2018/064600 A1 | 4/2018 |

OTHER PUBLICATIONS

Hu, Chuhong, Ronald W. Busuttil, and Gerald S. Lipshutz. "RH10 provides superior transgene expression in mice when compared with natural AAV serotypes for neonatal gene therapy." The journal of gene medicine 12.9 (2010): 766-778.*

U.S. Appl. No. 16/611,581, filed Nov. 7, 2019, Mueller et al.

U.S. Appl. No. 18/505,163, filed Nov. 9, 2023, Mueller et al.

U.S. Appl. No. 18/344,926, filed Jun. 30, 2023, Mueller et al.

EP 15764861.9, Dec. 15, 2017, Extended European Search Report.

EP 20183218.5, Nov. 10, 2020, Partial European Search Report.

EP 20183218.5, Mar. 31, 2021, Extended European Search Report.

PCT/US2015/021321, Jun. 26, 2015, International Search Report and Written Opinion.

PCT/US2015/021321, Sep. 26, 2016, International Preliminary Report on Patentability.

U.S. Appl. No. 16/611,581, May 7, 2021, Third Party Submission.

EP 18797613.9, Dec. 8, 2020, Extended European Search Report.

PCT/US2018/031880, Sep. 14, 2018, Internatioinal Search Report and Written Opinion.

PCT/US2018/031880, Nov. 21, 2019, International Preliminary Report on Patentability.

EP 18859329.7, May 3, 2021, Extended European Search Report.

PCT/US2018/052173, Nov. 30, 2018, International Search Report and Written Opinion.

PCT/US2018/052173, Apr. 2, 2020, International Preliminary Report on Patentability.

Extended European Search Report for Application No. EP 15764861. 9, mailed Dec. 15, 2017.

Partial European Search Report for Application No. EP 20183218.5, mailed Nov. 10, 2020.

Extended European Search Report for Application No. EP 20183218. 5, mailed Mar. 31, 2021.

International Search Report and Written Opinion for Application No. PCT/US2015/021321, mailed Jun. 26, 2015.

International Preliminary Report on Patentability for Application No. PCT/US2015/021321, mailed Sep. 26, 2016.

Extended European Search Report for Application No. EP 18797613. 9, mailed Dec. 8, 2020.

Third Party Submission under 37 CFR 1.290 for U.S. Appl. No. 16/611,581, filed May 7, 2021.

International Search Report and Written Opinion for Application No. PCT/US2018/031880, mailed Sep. 14, 2018.

International Preliminary Report on Patentability for Application No. PCT/US2018/031880, mailed Nov. 21, 2019.

Extended European Search Report for application No. EP 18859329. 7, mailed May 3, 2021.

International Search Report and Written Opinion for Application No. PCT/US2018/052173, mailed Nov. 30, 2018.

International Preliminary Report on Patentability for Application No. PCT/US2018/052173, mailed Apr. 2, 2020.

Aartsma-Rus et al., New insights in gene-derived therapy: the example of Duchenne muscular dystrophy. Ann N Y Acad Sci. Dec. 2010;1214:199-212. doi: 10.1111/j.1749-6632.2010.05836.x. Epub Dec. 1, 2010.

Abdallah et al., Gene editing ALS causing (GGGGCC)n repeat expansion in C9orf72 using CRISPER/Cas9 system. Mol Ther. May 2017; 25(5): 299-300. American Society of Gene and Cell Therapy.

Adachi et al., Drawing a high-resolution functional map of adeno-associated virus capsid by massively parallel sequencing. Nat Commun 2014;5:3075. doi: 10.1038/ncomms4075.

Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].

Akache et al., The 37/67-kilodalton laminin receptor is a receptor for adeno-associated virus serotypes 8, 2, 3, and 9. J Virol. Oct. 2006;80(19):9831-6.

Alisky et al., Gene therapy for amyotrophic lateral sclerosis and other motor neuron diseases. Hum Gene Ther. Nov. 20, 2000;11(17):2315-29.

Arbuthnot et al., Hepatic delivery of RNA interference activators for therapeutic application. Curr Gene Ther. Apr. 2009;9(2):91-103.

Asokan et al., The AAV vector toolkit: poised at the clinical crossroads. Mol Ther. Apr. 2012;20(4):699-708. doi: 10.1038/mt. 2011.287. Epub Jan. 24, 2012.

Azzouz et al., VEGF delivery with retrogradely transported lentivector prolongs survival in a mouse ALS model. Nature. May 27, 2004;429(6990):413-7.

Baek et al., AAV-mediated gene delivery in adult GM1-gangliosidosis mice corrects lysosomal storage in CNS and improves survival. PLoS One. Oct. 18, 2010;5(10):e13468. doi: 10.1371/journal.pone.0013468.

Banci et al., SOD1 and amyotrophic lateral sclerosis: mutations and oligomerization. PLoS One. 2008;3(2):e1677. Published Feb. 27, 2008. doi:10.1371/journal.pone.0001677.

Berns et al., Biology of adeno-associated virus. Curr Top Microbiol Immunol. 1996;218:1-23.

Beutler et al., AAV for pain: steps towards clinical translation. Gene Ther. Apr. 2009; 16(4):461-9. Epub Mar. 5, 2009.

Biferi et al., Recombinant AAV9 vectors to silence the mutant SOD1 gene in amyotrophic lateral sclersosis. Human gene therapy. Dec. 2013;24(12):A117.

Bish et al., Adeno-associated virus (AAV) serotype 9 provides global cardiac gene transfer superior to AAV1, AAV6, AAV7, and AAV8 in the mouse and rat. Hum Gene Ther. Dec. 2008; 19(12):1359-68. doi: 10.1089/hum.2008.123.

Boillée et al., Onset and progression in inherited ALS determined by motor neurons and microglia. Science. Jun. 2, 2006;312(5778):1389-92.

Borel et al., Recombinant AAV as a platform for translating the therapeutic potential of RNA interference. Mol Ther. Apr. 2014;22(4):692-701. doi:10.1038/mt.2013.285. Epub Dec. 19, 2013.

(56) References Cited

OTHER PUBLICATIONS

Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.

Brantly et al., Phase I trial of intramuscular injection of a recombinant adeno-associated virus serotype 2 alphal-antitrypsin (AAT) vector in AAT-deficient adults. Hum Gene Ther. Dec. 2006; 17(12):1177-86.

Brown et al., A microRNA-regulated lentiviral vector mediates stable correction of hemophilia B mice. Blood. Dec. 15, 2007;110(13):4144-52. Epub Aug. 28, 2007.

Brown et al., Endogenous microRNA can be broadly exploited to regulate transgene expression according to tissue, lineage and differentiation state. Nat Biotechnol. Dec. 2007;25(12):1457-67. Epub Nov. 16, 2007.

Brown et al., Endogenous microRNA regulation suppresses transgene expression in hematopoietic lineages and enables stable gene transfer. Nat Med. May 2006; 12(5):585-91. Epub Apr. 23, 2006.

Buning et al., Receptor targeting of adeno-associated virus vectors. Gene Ther. Jul. 2003;10(14):1142-51.

Bussing et al., let-7 microRNAs in development, stem cells and cancer. Trends Mol Med. Sep. 2008;14(9):400-9. doi: 10.1016/j.molmed.2008.07.001. Epub Jul. 31, 2008.

Calcedo et al., Worldwide epidemiology of neutralizing antibodies to adeno-associated viruses. J Infect Dis. Feb. 1, 2009;199(3):381-90.

Carter et al., Adeno-associated virus gene expression and regulation. CRC Handbook of parvoviruses. 1990:227-54.

Carter, in "Handbook of Parvoviruses", ed., P. Tijsser, CRC Press, pp. 155-168 (1990).

Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.

Cearley et al., Transduction characteristics of adeno-associated virus vectors expressing cap serotypes 7, 8, 9, and Rh10 in the mouse brain. Mol Ther. Mar. 2006;13(3):528-37. Epub Jan. 18, 2006.

Chadderton et al., Improved retinal function in a mouse model of dominant retinitis pigmentosa following AAV-delivered gene therapy. Mol Ther. Apr. 2009;17(4):593-9. Epub Jan. 27, 2009.

Chang et al., miR-122, a mammalian liver-specific microRNA, is processed from her mRNA and may downregulate the high affinity cationic amino acid transporter CAT-1. RNA Biol. Jul. 2004;1(2):106-13. Epub Jul. 1, 2004.

Chen et al., Comparative study of anti-hepatitis B virus RNA interference by double-stranded adeno-associated virus serotypes 7, 8, and 9. Mol Ther. Feb. 2009;17(2):352-9. Epub Dec. 9, 2008.

Chen et al., Efficient transduction of vascular endothelial cells with recombinant adeno-associated virus serotype 1 and 5 vectors. Hum Gene Ther. Feb. 2005;16(2):235-47.

Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.

Chen et al., Regulation of immune responses and tolerance: the microRNA perspective. Immunol Rev. May 2013;253(1):112-28. doi:10.1111/imr.12060.

Chen et al., Development of hybrid baculovirus vectors for artificial MicroRNA delivery and prolonged gene suppression. Biotechnol Bioeng. Dec. 2011;108(12):2958-67. doi: 10.1002/bit.23250. Epub Jul. 19, 2011.

Cheng et al., Development of optimized AAV3 serotype vectors: mechanism of high-efficiency transduction of human liver cancer cells. Gene Ther. Apr. 2012; 19(4):375-84. doi: 10.1038/gt.2011. 105. Epub Jul. 21, 2011.

Choudhury et al., Identification of Novel vectors capable of CNS transduction in adult mice after single round selection using DNA shuffled AAV capsid library. Mol Ther. May 1, 2013;21(1):S1.

Christensen et al., A let-7 microRNA-binding site polymorphism in the KRAS 3' UTR is associated with reduced survival in oral cancers. Carcinogenesis. Jun. 2009;30(6):1003-7. doi: 10.1093/carcin/bgp099. Epub Apr. 20, 2009.

Chung et al., Polycistronic RNA polymerase II expression vectors for RNA interference based on BIC/miR-155. Nucleic Acids Res. Apr. 13, 2006;34(7):e53.

Ciura et al., Loss of function of C9orf72 causes motor deficits in a zebrafish model of amyotrophic lateral sclerosis. Ann Neurol. Aug. 2013;74(2):180-7. doi: 10.1002/ana.23946.

Cleary, Effect of C9orf72 hexanucleotide repeat expansions on human induced pluripotent stem cell derived oligodendrocytes. The University of Edinburgh PhD Dissertation. Jan. 12, 2017. 220 pages.

Conlon et al., Ribozyme Approaches towards Down-Regulation of Pi*Z Mutant Human a-1 Anti-Trypsin. Mol. Therapy. 2004;9:S333. Abstract 875.

Conrad et al., Safety of single-dose administration of an adeno-associated virus (AAV)-CFTR vector in the primate lung. Gene Ther. Aug. 1996;3(8):658-68.

Coulouarn et al., Loss of miR-122 expression in liver cancer correlates with suppression of the hepatic phenotype and gain of metastatic properties. Oncogene. Oct. 8, 2009;28(40):3526-36. doi: 10.1038/onc.2009.211. Epub Jul. 20, 2009.

Cruz et al., The promise of gene therapy for the treatment of alpha-1 antitrypsin deficiency. Pharmacogenomics. Sep. 2007;8(9):1191-8.

Csak et al., microRNA-122 regulates hypoxia-inducible factor-1 and vimentin in hepatocytes and correlates with fibrosis in diet-induced steatohepatitis. Liver Int. Feb. 2015;35(2):532-41. doi: 10.1111/liv.12633. Epub Jul. 28, 2014.

Czech, MicroRNAs as therapeutic targets. N Engl J Med. Mar. 16, 2006;354(11):1194-5.

Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.

Davidson et al., Recombinant adeno-associated virus type 2, 4, and 5 vectors: transduction of variant cell types and regions in the mammalian central nervous system. Proc Natl Acad Sci U S A. Mar. 28, 2000;97(7):3428-32.

Daya et al., Gene therapy using adeno-associated virus vectors. Clin Microbiol Rev. Oct. 2008;21(4):583-93. doi: 10.1128/CMR.00008-08.

Di Giorgio et al., Non-cell autonomous effect of glia on motor neurons in an embryonic stem cell-based ALS model. Nat Neurosci. May 2007;10(5):608-14. Epub Apr. 15, 2007.

Dominov et al., A novel dysferlin mutant pseudoexon bypassed with antisense oligonucleotides. Ann Clin Transl Neurol. Sep. 2014; 1(9):703-20. doi: 10.1002/acn3.96. Epub Sep. 27, 2014.

Donnelly et al., RNA toxicity from the ALS/FTD C9ORF72 expansion is mitigated by antisense intervention. Neuron. Oct. 16, 2013;80(2):415-28. doi: 10.1016/j.neuron.2013.10.015. Erratum in: Neuron. Nov. 20, 2013;80(4):1102. Heusler, Aaron R [corrected to Haeusler, Aaron R].

Donnelly et al., RNA toxicity from the ALS/FTD C9ORF72 expansion is mitigated by antisense intervention. Neuron. Oct. 16, 2013;80(Supplemental Information). 33 pages.

Duque et al., Intravenous administration of self-complementary AAV9 enables transgene delivery to adult motor neurons. Mol Ther. Jul. 2009; 17(7):1187-96. doi: 10.1038/mt.2009.71. Epub Apr. 14, 2009.

Eberling et al., Results from a phase I safety trial of hAADC gene therapy for Parkinson disease. Neurology. May 2, 20080;70(21):1980-3. doi: 10.1212/01.wnl.0000312381.29287.ff. Epub Apr. 9, 2008.

Ebert et al., MicroRNA sponges: competitive inhibitors of small RNAs in mammalian cells. Nat Methods. Sep. 2007;4(9):721-6. Epub Aug. 12, 2007.

Ehlert et al., Cellular toxicity following application of adeno-associated viral vector-mediated RNA interference in the nervous system. BMC Neurosci. Feb. 18, 2010;11:20.

Elmén et al., LNA-mediated microRNA silencing in non-human primates. Nature. Apr. 2008;452(17): 896-900.

Elmén et al., bAntagonism of microRNA-122 in mice by systemically administered LNA-antimiR leads to up-regulation of a large

(56)　　　　　References Cited

OTHER PUBLICATIONS set of predicted target mRNAs in the liver. Nucleic Acids Res. Mar. 2008;36(4):1153-62. Epub Dec. 23, 2007.

Esau et al., miR-122 regulation of lipid metabolism revealed by in vivo antisense targeting. Cell Metab. Feb. 2006;3(2):87-98.

Fabani et al., miR-122 targeting with LNA/2'-O-methyl oligonucleotide mixmers, peptide nucleic acids (PNA), and PNA-peptide conjugates. RNA. Feb. 2008; 14(2):336-46. Epub Dec. 11, 2007.

Fechner et al., Cardiac-targeted RNA interference mediated by an AAV9 vector improves cardiac function in coxsackievirus B3 cardiomyopathy. J Mol Med (Berl). Sep. 2008;86(9):987-97. doi: 10.1007/s00109-008-0363-x. Epub Jun. 12, 2008.

Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.

Fernandes et al., Oligonucleotide-Based Therapy for FTD/ALS Caused by the C9orf72 Repeat Expansion: A Perspective. J Nucleic Acids. 2013;2013:208245. doi: 10.1155/2013/208245. Epub Nov. 17, 2013.

Fischer et al., Successful transgene expression with serial doses of aerosolized rAAV2 vectors in rhesus macaques. Mol Ther. Dec. 2003;8(6):918-26.

Fisher et al., Transduction with recombinant adeno-associated virus for gene therapy is limited by leading-strand synthesis. J Virol. Jan. 1996;70(1):520-32.

Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.

Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.

Forman et al., A search for conserved sequences in coding regions reveals that the let-7 microRNA targets Dicer within its coding sequence. Proc Natl Acad Sci U S A. Sep. 30, 2008;105(39):14879-84. doi: 10.1073/pnas.0803230105. Epub Sep. 23, 2008.

Foust et al., Intravascular AAV9 preferentially targets neonatal-neurons and adult-astrocytes. Nature Biotechnology, 27; 59-65 2009.

Foust et al., Rescue of the spinal muscular atrophy phenotype in a mouse model by early postnatal delivery of SMN. Nat Biotechnol. Mar. 2010;28(3):271-4. doi: 10.1038/nbt.1610. Epub Feb. 28, 2010.

Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.

Fu et al., Self-complementary adeno-associated virus serotype 2 vector: global distribution and broad dispersion of AAV-mediated transgene expression in mouse brain. Mol Ther. Dec. 2003;8(6):911-7.

Gadalla et al., Improved survival and reduced phenotypic severity following AAV9/MECP2 gene transfer to neonatal and juvenile male Mecp2 knockout mice. Mol Ther. Jan. 2013;21(1):18-30. doi:10.1038/mt.2012.200. Epub Sep. 25, 2012.

Gaj et al., Genome Engineering Using Adeno-associated Virus: Basic and Clinical Research Applications. Mol Ther. Mar. 2016;24(3):458-64. doi: 10.1038/mt.2015.151. Epub Sep. 16, 2015.

Gao et al., Erythropoietin gene therapy leads to autoimmune anemia in macaques. Blood. May 1, 2004;103(9):3300-2. Epub Dec. 24, 2003.

Gao et al., Inadvertent gene transfer of co-packaged rep and cap sequences during the production of AAV vector and its potential impact on vector performance. Molecular Therapy. May 2008; 16(Suppl. 1):S105-S106. Abstract 279.

Gao et al., Novel adeno-associated viruses from rhesus monkeys as vectors for human gene therapy. Proc Natl Acad Sci U S A. Sep. 3, 2002;99(18):11854-9. Epub Aug. 21, 2002.

Gao et al., RAAV-mediated targeting in adult mice and its potential in generating animal models of tissue-specific somatic transgenics or knock down. Molecular Therapy. May 2008;16(1):S118-S119. Abstract 316.

GENBANK Submission; NCBI, Accession No. AAS99264; Gao et al.; Jun. 24, 2004.

GENBANK Submission; NCBI, Accession No. AY530579.10; 2004.

Gentner et al., Stable knockdown of microRNA in vivo by lentiviral vectors. Nat Methods. Jan. 2009;6(1):63-6. doi: 10.1038/nmeth.1277. Epub Nov. 30, 2008.

Georgiadis et al., AAV-mediated knockdown of peripherin-2 in vivo using miRNA-based hairpins. Gene Ther. Apr. 2010;17(4):486-93. doi: 10.1038/gt.2009.162. Epub Dec. 10, 2009.

Girard et al., miR-122, a paradigm for the role of microRNAs in the liver. J Hepatol. Apr. 2008;48(4):648-56. doi: 10.1016/j.jhep.2008.01.019. Epub Feb. 12, 2008.

Gramantieri et al., Cyclin G1 is a target of miR-122a, a microRNA frequently down-regulated in human hepatocellular carcinoma. Cancer Res. Jul. 1, 2007;67(13):6092-9.

Grimm et al., Fatality in mice due to oversaturation of cellular microRNA/short hairpin RNA pathways. Nature. May 25, 2006;441(7092):537-41.

Grimm, Small silencing RNAs: state-of-the-art. Adv Drug Deliv Rev. Jul. 25, 2009;61(9):672- 703. doi: 10.1016/j.addr.2009.05.002. Epub May 7, 2009.

Haraguchi et al., Vectors expressing efficient RNA decoys achieve the long-term suppression of specific microRNA activity in mammalian cells. Nucleic Acids Res. Apr. 2009;37(6):e43. doi: 10.1093/nar/gkp040. Epub Feb. 17, 2009.

Haussecker et al., miR-122 continues to blaze the trail for microRNA therapeutics. Mol Ther. Feb. 2010;18(2):240-2. doi: 10.1038/mt.2009.313.

Hernandez et al., Latent adeno-associated virus infection elicits humoral but not cell-mediated immune responses in a nonhuman primate model. J Virol. Oct. 1999;73(10):8549-58.

Hinderer et al., Widespread gene transfer in the central nervous system of cynomolgus macaques following delivery of AAV9 into the cisterna magna. Mol Ther Methods Clin Dev. Dec. 10, 2014;1:14051. doi: 10.1038/mtm.2014.51. PMID: 26052519; PMCID: PMC4448732.

Horwich et al., Design and delivery of antisense oligonucleotides to block microRNA function in cultured Drosophila and human cells. Nat Protoc. 2008;3(10):1537-49. doi: 10.1038/nprot.2008.145.

Hsu et al., Essential metabolic, anti-inflammatory, and anti-tumorigenic functions of miR-122 in liver. J Clin Invest. Aug. 2012;122(8):2871-83. doi: 10.1172/JCI63539. Epub Jul. 23, 2012.

Hutvágner et al., Sequence-specific inhibition of small RNA function. PLoS Biol. Apr. 2004;2(4): E98. Epub Feb. 24, 2004.

Iida et al., Systemic Delivery of Tyrosine-Mutant AAV Vectors Results in Robust Transduction of Neurons in Adult Mice. BioMed Res Int. 2013;2013.

Jakobsson et al., Lentiviral vectors for use in the central nervous system. Mol Ther. Mar. 2006;13(3):484-93. Epub Jan. 3, 2006.

Johnson et al., RAS is regulated by the let-7 microRNA family. Cell. Mar. 11, 2005;120(5):635-47.

Kaspar et al., Retrograde viral delivery of IGF-1 prolongs survival in a mouse ALS model. Science. Aug. 8, 2003;301(5634):839-42.

Koornneef et al., Apolipoprotein B knockdown by AAV-delivered shRNA lowers plasma cholesterol in mice. Mol Ther. Apr. 2011;19(4):731-40. doi:10.1038/mt.2011.6. Epub Feb. 8, 2011.

Kota et al., AAV8-Mediated Delivery of miR-26a inhibits cancer cell proliferation and induces tumor-specific apoptosis in a liver cancer model. Mol. Therapy. May 2009. 17(1):S300. Abstract 783.

Kota et al., Therapeutic microRNA delivery suppresses tumorigenesis in a murine liver cancer model. Cell. Jun. 12, 2009;137(6):1005-17. doi: 10.1016/j.cell.2009.04.021.

Kotin et al., Organization of adeno-associated virus DNA in latently infected Detroit 6 cells. Virology. Jun. 1989;170(2):460-7.

Kotin et al., Site-specific integration by adeno-associated virus. Proc Natl Acad Sci U S A. Mar. 1990;87(6):2211-5.

Krützfeldt et al., Silencing of microRNAs in vivo with 'antagomirs'. Nature. Dec. 1, 2005;438(7068):685-9. Epub Oct. 30, 2005.

(56)        References Cited

OTHER PUBLICATIONS

Kubodera et al., In vivo application of an RNAi strategy for the selective suppression of a mutant allele. Hum Gene Ther. Jan. 2011;22(1):27-34. doi: 10.1089/hum.2010.054. PMID: 20649474.

Kutay et al., Downregulation of miR-122 in the rodent and human hepatocellular carcinomas. J Cell Biochem. Oct. 15, 2006;99(3):671-8.

Lagier-Tourenne et al., Targeted degradation of sense and antisense C9orf72 RNA foci as therapy for ALS and frontotemporal degeneration. Proc Natl Acad Sci U S A. Nov. 19, 2013;110(47):E4530-9. doi: 10.1073/pnas.1318835110. Epub Oct. 29, 2013.

Lanford et al., Therapeutic silencing of microRNA-122 in primates with chronic hepatitis C virus infection. Science. Jan. 8, 2010;327(5962):198-201. Epub Dec. 3, 2009.

Lebedeva et al., Phosphorothioate Oligodeoxynucleotides as Inhibitors of Gene Expression: Antisense and Non-Antisense Effects. In: Rabbani, L.E. (eds) Applications of Antisense Therapies to Restenosis. Perspectives in Antisense Science. 1999; 3:99-118. https://doi.org/10.1007/978-1-4615-5183-6_6.

Lewis et al., Conserved seed pairing, often flanked by adenosines, indicates that thousands of human genes are microRNA targets. Cell. Jan. 14, 2005;120(1):15-20.

Lewis et al., Prediction of mammalian microRNA targets. Cell. Dec. 26, 2003;115(7):787-98.

Li et al., Efficient and Targeted Transduction of Nonhuman Primate Liver With Systemically Delivered Optimized AAV3B Vectors. Mol Ther. Dec. 2015;23(12):1867-76. doi: 10.1038/mt.2015.174. Epub Sep. 25, 2015.

Li et al., Intronic microRNA: discovery and biological implications. DNA Cell Biol. Apr. 2007;26(4):195-207.

Li et al., Protein trans-splicing as a means for viral vector-mediated in vivo gene therapy. Hum Gene Ther. Sep. 2008;19(9):958-64. doi: 10.1089/hum.2008.009.

Liu et al., Altered microRNA expression following traumatic spinal cord injury. Exp Neurol. Oct. 2009;219(2):424-9. doi: 10.1016/j.expneurol.2009.06.015. Epub Jul. 1, 2009.

Liu et al., Identification of a novel loss-of-function C9orf72 splice site mutation in a patient with amyotrophic lateral sclerosis. Neurobiol Aging. Nov. 2016;47:219.e1-219.e5. doi: 10.1016/j.neurobiolaging.2016.07.027. Epub Aug. 8, 2016.

Liu et al., miRNA cassettes in viral vectors: problems and solutions. Biochim Biophys Acta. Nov.-Dec. 2011;1809(11-12):732-45. doi: 10.1016/j.bbagrm.2011.05.014. Epub Jun. 7, 2011.

Lisowski et al., Adeno-associated virus serotypes for gene therapeutics. Curr Opin Pharmacol. Oct. 2015;24:59-67. doi: 10.1016/j.coph.2015.07.006. Epub Aug. 25, 2015.

Lowenstein, Crossing the rubicon. Nat Biotechnol. Jan. 2009;27(1):42-4.

Loya et al., Transgenic microRNA inhibition with spatiotemporal specificity in intact organisms. Nat Methods. Dec. 2009;6(12):897-903. doi: 10.1038/nmeth.1402. Epub Nov. 15, 2009.

Lux et al., Green fluorescent protein-tagged adeno-associated virus particles allow the study of cytosolic and nuclear trafficking. J Virol. Sep. 2005;79(18):11776-87.

Lynn, Meta-regulation: microRNA regulation of glucose and lipid metabolism. Trends Endocrinol Metab. Nov. 2009;20(9):452-9. doi: 10.1016/j.tem.2009.05.007. Epub Sep. 30, 2009.

Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.

Maguire et al., Directed evolution of adeno-associated virus for glioma cell transduction. J Neurooncol. Feb. 2010;96(3):337-47. doi: 10.1007/s11060-009-9972-7. Epub Jul. 19, 2009.

Maguire et al., Gene therapy for the nervous system: challenges and new strategies. Neurotherapeutics. Oct. 2014; 11(4):817-39. doi: 10.1007/s13311-014-0299-5.

Mandel et al., Recombinant adeno-associated viral vectors as therapeutic agents to treat neurological disorders. Mol Ther. Mar. 2006; 13(3):463-83. Epub Jan. 18, 2006.

Manfredsson et al., AAV9: a potential blood-brain barrier buster. Mol Ther. Mar. 2009;17(3):403-5.

Matalon et al., Adeno-associated virus-mediated aspartoacylase gene transfer to the brain of knockout mouse for canavan disease. Mol Ther. May 2003;7(5 Pt 1):580-7.

Mcbride et al., Artificial miRNAs mitigate shRNA-mediated toxicity in the brain: implications for the therapeutic development of RNAi. Proc Natl Acad Sci U S A. Apr. 15, 2008;105(15):5868-73. Epub Apr. 8, 2008.

Mccarty et al., Adeno-associated virus terminal repeat (TR) mutant generates self-complementary vectors to overcome the rate-limiting step to transduction in vivo. Gene Ther. Dec. 2003;10(26):2112-8.

Mccarty et al., Integration of adeno-associated virus (AAV) and recombinant AAV vectors. Annu Rev Genet. 2004;38:819-45.

Mccarty et al., Self-complementary recombinant adeno-associated virus (scAAV) vectors promote efficient transduction independently of DNA synthesis. Gene Ther. Aug. 2001;8(16):1248-54.

Mccarty, Self-complementary AAV vectors; advances and applications. Mol Ther. Oct. 2008;16(10):1648-56. Epub Aug. 5, 2008.

Mccurdy et al., Sustained normalization of neurological disease after intracranial gene therapy in a feline model. Sci Transl Med. Apr. 9, 2014;6(231):231ra48. doi: 10.1126/scitranslmed.3007733.

Meijer et al., Controlling brain tumor growth by intraventricular administration of an AAV vector encoding IFN-beta. Cancer Gene Ther. Aug. 2009;16(8):664-71. doi: 10.1038/cgt.2009.8. Epub Feb. 6, 2009.

Meister et al., Sequence-specific inhibition of microRNA- and siRNA-induced RNA silencing. RNA. Mar. 2004;10(3):544-50.

Mietzsch et al., OneBac 2.0: Sf9 Cell Lines for Production of AAV5 Vectors with Enhanced Infectivity and Minimal Encapsidation of Foreign DNA. Hum Gene Ther. Oct. 2015;26(10):688-97. doi:10. 1089/hum.2015.050. Epub Aug. 6, 2015.

MiRBase accession No. MI0000472. Last accessed on May 18, 2018 at http://www.mirbase.org/cgi-bin/mirna_entry.pl?acc= MI0000472.

Moffett et al., N-Acetylaspartate in the CNS: from neurodiagnostics to neurobiology. Prog Neurobiol. Feb. 2007;81(2):89-131. Epub Jan. 5, 2007.

Moss et al., Repeated adeno-associated virus serotype 2 aerosol-mediated cystic fibrosis transmembrane regulator gene transfer to the lungs of patients with cystic fibrosis: a multicenter, double-blind, placebo-controlled trial. Chest. Feb. 2004;125(2):509-21.

Mueller et al., Development of Simultaneous Gene Augmentation and Reduction of Mutant Gene Expression with a Single Recombinant AAV for Alpha-1 Antitrypsin Disease. Molecular Therapy May 2009; 17(1):S391-S392. Abstract 1030.

Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.

Mueller et al., Using rAAV Delivered miRNAs To Knockdown Misfolded Human Alpha 1 Antitrypsin in a Transgenic Mouse Model. Molecular Therapy May 2010;18(1):S21. Abstract 51.

O'Reilly et al., RNA interference-mediated suppression and replacement of human rhodopsin in vivo. Am J Hum Genet. Jul. 2007;81(1):127-35. Epub May 23, 2007.

Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.

Pertin et al., Efficacy and specificity of recombinant adeno-associated virus serotype 6 mediated gene transfer to drg neurons through different routes of delivery. Poster sessions. Eur J. Pain. 2009;13:S74. Abstract 229.

Pinto et al., Impeding Transcription of Expanded Microsatellite Repeats by Deactivated Cas9. Mol Cell. Nov. 2, 2017;68(3):479-490.e5. doi: 10.1016/j.molcel.2017.09.033. Epub Oct. 19, 2017.

Pribadi et al., CRISPR-Cas9 targeted deletion of the C9orf72 repeat expansion mutation corrects cellular phenotypes in patient-derived iPS cells. Preprint published May 2, 2016.

Ralph et al., Silencing mutant SOD1 using RNAi protects against neurodegeneration and extends survival in an ALS model. Nat Med. Apr. 2005;11(4):429-33. Epub Mar. 13, 2005.

(56) References Cited

OTHER PUBLICATIONS

Ran et al., In vivo genome editing using *Staphylococcus aureus* Cas9. Nature. Apr. 9, 2015;520(7546):186-91. doi: 10.1038/nature14299. Epub Apr. 1, 2015.

Raoul et al., Lentiviral-mediated silencing of SOD1 through RNA interference retards disease onset and progression in a mouse model of ALS. Nat Med. Apr. 2005;11(4):423-8. Epub Mar. 13, 2005.

Renton et al., State of play in amyotrophic lateral sclerosis genetics. Nat Neurosci. 2014;17(1):17-23. doi:10.1038/nn.3584.

Sambrook et al., "Molecular Cloning. A Laboratory Manual", 2d ed., Cold Spring Harbor Laboratory, New York (1989).

Sareen et al., Targeting RNA foci in iPSC-derived motor neurons from ALS patients with a C9ORF72 repeat expansion. Sci Transl Med. Oct. 23, 2013;5(208):208ra149. doi: 10.1126/scitranslmed.3007529.

Schnepp et al., Characterization of adeno-associated virus genomes isolated from human tissues. J Virol. Dec. 2005;79(23):14793-803.

Sen et al., Micromanaging vascular biology: tiny microRNAs play big band. J Vasc Res. 2009;46(6):527-40. doi: 10.1159/000226221. Epub Jun. 30, 2009.

Shan et al., A quick and efficient approach for gene silencing by using triple putative microRNA-based short hairpin RNAs. Mol Cell Biochem. Mar. 2009;323(1-2):81-9. doi: 10.1007/s11010-008-9966-3. Epub Nov. 27, 2008.

Sin et al., Gene silencing efficiency and INF-ß induction effects of splicing miRNA 155-based artificial miRNA with pre-miRNA stem-loop structures. Biochem Genet. Feb. 2012;50(1-2):112-21. doi: 10.1007/s10528-011-9476-y. Epub Nov. 27, 2011.

Sirninger et al., Functional characterization of a recombinant adeno-associated virus 5-pseudotyped cystic fibrosis transmembrane conductance regulator vector. Hum Gene Ther. Sep. 2004;15(9):832-41. doi: 10.1089/hum.2004.15.832.

Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.

Sondhi et al., Enhanced survival of the LINCL mouse following CLN2 gene transfer using the rh.10 rhesus macaque-derived adeno-associated virus vector. Mol Ther. Mar. 2007;15(3):481-91. Epub Dec. 19, 2006.

Stoica et al., Targeting Human SOD1 Using AAV mediated RNAi in a mouse model of amyotrophic lateral sclerosis. Mol ther. Jun. 2013;21(1):S149.

Stoica et al., Adeno-associated virus-delivered artificial microRNA extends survival and delays paralysis in an amyotrophic lateral sclerosis mouse model. Ann Neurol. Apr. 2016;79(4):687-700. doi: 10.1002/ana.24618. Epub Mar. 11, 2016. Author Manuscript, 24 pages.

Storek et al., Intrathecal long-term gene expression by self-complementary adeno-associated virus type 1 suitable for chronic pain studies in rats. Mol Pain. Jan. 30, 2006;2:4.

Storkebaum et al., Treatment of motoneuron degeneration by intracerebroventricular delivery of VEGF in a rat model of ALS. Nat Neurosci. Jan. 2005;8(1):85-92. Epub Nov. 28, 2004.

Suckau et al., 851. The Effect of Genome Size and Design of scAAV Vectors on Efficiency of shRNA Expression and Gene Knockdown. May 1, 2007;15(1):S325.

Tanimizu et al., Downregulation of miR122 by grainyhead-like 2 restricts the hepatocytic differentiation potential of adult liver progenitor cells. Development. Dec. 2014;141(23):4448-56. doi:10.1242/dev.113654. Epub Nov. 18, 2014.

Tenenbaum et al., Recombinant AAV-mediated gene delivery to the central nervous system. J Gene Med. Feb. 2004;6 Suppl 1:S212-22.

Tokumaru et al., let-7 regulates Dicer expression and constitutes a negative feedback loop. Carcinogenesis. Nov. 2008;29(11):2073-7. doi: 10.1093/carcin/bgn187. Epub Aug. 11, 2008.

Tomar et al., Use of adeno-associated viral vector for delivery of small interfering RNA. Oncogene. Aug. 28, 2003;22(36):5712-5.

Toro et al., 603. Artificial MicroRNAs Against Spliced Variants of the Gene C9ORF72, the Major Cause for Familial Amyotrophic Lateral Sclerosis. Mol Ther. May 2013;21(Supplement 1):S230-S231. doi: 10.1016/S1525-0016(16)34938-3.

Towne et al., Systemic AAV6 delivery mediating RNA interference against SOD1: neuromuscular transduction does not alter disease progression in fALS mice. Mol Ther. Jun. 2008;16(6):1018-25. doi: 10.1038/mt.2008.73. Epub Apr. 15, 2008.

Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.

Tsai et al., MicroRNA-122, a tumor suppressor microRNA that regulates intrahepatic metastasis of hepatocellular carcinoma. Hepatology. May 2009;49(5):1571-82. doi: 10.1002/hep.22806.

U.S. Appl. No. 15/098,833, filed Apr. 14, 2016, Flotte et al.

U.S. Appl. No. 15/120,294, filed Aug. 19, 2016, Gao et al.

U.S. Appl. No. 15/316,027, filed Dec. 2, 2016, Brown et al.

U.S. Appl. No. 15/367,708, filed Dec. 2, 2016, Gao et al.

U.S. Appl. No. 15/423,702, filed Feb. 3, 2017, Gao et al.

U.S. Appl. No. 15/423,720, filed Feb. 3, 2017, Gao et al.

U.S. Appl. No. 15/516,582, filed Apr. 3, 2017, Esteves et al.

U.S. Appl. No. 15/516,585, filed Apr. 3, 2017, Esteves et al.

U.S. Appl. No. 15/567,847, filed Oct. 19, 2017, Esteves et al.

U.S. Appl. No. 15/568,650, filed Oct. 23, 2017, Gao et al.

U.S. Appl. No. 15/578,994, filed Dec. 1, 2017, Cataltepe.

U.S. Appl. No. 15/613,646, filed Jun. 5, 2017, Gao et al.

U.S. Appl. No. 15/747,801, filed Jan. 26, 2018, Fitzgerald et al.

UNIPROT Submission; Accession No. A8IGP7; Nov. 13, 2013.

UNIPROT Submission; Accession No. H3GK32; Feb. 6, 2013.

UNIPROT Submission; Accession No. T2BRA8; Nov. 13, 2013.

Vandenberghe et al., Heparin binding directs activation of T cells against adeno-associated virus serotype 2 capsid. Nat Med. Aug. 2006;12(8):967-71. Epub Jul. 16, 2006.

Vandenberghe et al., Tailoring the AAV vector capsid for gene therapy. Gene Ther. Mar. 2009; 16(3):311-9. Epub Dec. 4, 2008.

Vandendriessche et al., Efficacy and safety of adeno-associated viral vectors based on serotype 8 and 9 vs. lentiviral vectors for hemophilia B gene therapy. J Thromb Haemost. Jan. 2007;5(1):16-24. Epub Sep. 26, 2006.

Vaucheret et al., The action of ARGONAUTE1 in the miRNA pathway and its regulation by the miRNA pathway are crucial for plant development. Genes Dev. May 15, 2004;18(10):1187-97. Epub May 6, 2004.

Vermeulen et al., Double-stranded regions are essential design components of potent inhibitors of RISC function. RNA. May 2007;13(5):723-30. Epub Mar. 30, 2007.

Vulchanova et al., Differential adeno-associated virus mediated gene transfer to sensory neurons following intrathecal delivery by direct lumbar puncture. Mol Pain. May 28, 2010;6:31. doi: 10.1186/1744-8069-6-31.

Waldman et al., Applications of microRNA in cancer: Exploring the advantages of miRNA. Clin Transl Sci. Jun. 2009;2(3):248-9. doi: 10.1111/j.1752-8062.2009.00110.x.

Wang et al., Neuroprotective effects of glial cell line-derived neurotrophic factor mediated by an adeno-associated virus vector in a transgenic animal model of amyotrophic lateral sclerosis. J Neurosci. Aug. 15, 2002;22(16):6920-8.

Wang et al., Rescue and replication of adeno-associated virus type 2 as well as vector DNA sequences from recombinant plasmids containing deletions in the viral inverted terminal repeats: selective encapsidation of viral genomes in progeny virions. J Virol. Mar. 1996;70(3):1668-77.

Wang et al., Somatically Repairing Compound Heterozygous Recessive Mutations by Chromosomal Cut-and-Paste for in Vivo Gene Therapy. May 2016. 24(1):S289. Abstract 733.

Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.

Wang et al., The design of vectors for RNAi delivery system. Curr Pharm Des. 2008;14(13):1327-40.

Wang et al., The potential of adeno-associated viral vectors for gene delivery to muscle tissue. Expert Opin Drug Deliv. Mar. 2014; 11(3):345-64. doi: 10.1517/17425247.2014.871258. Epub Jan. 3, 2014.

(56)         References Cited

OTHER PUBLICATIONS

Wang et al., Therapeutic gene silencing delivered by a chemically modified small interfering RNA against mutant SOD1 slows amyotrophic lateral sclerosis progression. J Biol Chem. Jun. 6, 2008;283(23):15845-52. doi: 10.1074/jbc.M800834200. Epub Mar. 26, 2008.

Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.

Watson et al., Intrathecal administration of AAV vectors for the treatment of lysosomal storage in the brains of MPS I mice. Gene Ther. Jun. 2006;13(11):917-25.

Wein et al., Efficient bypass of mutations in dysferlin deficient patient cells by antisense-induced exon skipping. Hum Mutat. Feb. 2010;31(2):136-42. doi: 10.1002/humu.21160.

Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.

Weismann, Approaches and Considerations Towards a Safe and Effective Adena-Associated Virus Mediated Therapeutic Intervention for GM 1-Gangliosidosis: A Dissertation. University Massachusetts Medical School. Aug. 5, 2014.

Xia et al., Allele-specific RNAi selectively silences mutant SOD1 and achieves significant therapeutic benefit in vivo. Neurobiol Dis. Sep. 2006;23(3):578-86. Epub Jul. 20, 2006.

Xie et al., 676. DNA Sequences Encoding shRNAs Can Replace Mutant ITR in scAAV Genome for Efficient Replication and Packaging and Transcribe shRNAs by pol III Promoter Activity of wt ITR for Efficient Gene Silencing Mol Therapy. May 2015;23(1):S269.

Xie et al., Characterization of positioning effect of pol III-shRNA transcription unit in scAAV vector genome on the packaging efficiency and functionality of shRNA silencing. Molecular Therapy. May 2010;18(1): S262. Abstract 671.

Xie et al., Isolation of transcriptionally active novel AAV capsid sequences from chimpanzee tissues for vector development. Meeting Abstract: 12th Annual Meeting of the American Society of Gene Therapy. May 1, 2009. Abstract 91.

Xie et al., MicroRNA regulated tissue specific transduction by rAAV vector. Molecular Therapy. May 2009;17(1): S279. Abstract 732.

Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.

Xie et al., rAAV-mediated delivery of micro RNA scavengers leads to efficient and stable knockdown of cognate micro RNAs, upregulation of their natural target genes and phenotypic changes in mice. Molecular Therapy. May 2010;18(1): S140. Abstract362.

Xie et al., Short DNA Hairpins Compromise Recombinant Adeno-Associated Virus Genome Homogeneity. Mol Ther. Jun. 7, 2017;25(6):1363-1374. doi: 10.1016/j.ymthe.2017.03.028. Epub Apr. 24, 2017.

Xu et al., Delivery of MDR1 small interfering RNA by self-complementary recombinant adeno-associated virus vector. Mol Ther. Apr. 2005;11(4):523-30.

Yamada et al., RNA interference (RNAi). Clinical Chemistry. Sep. 2005;34(3):216-223.

Yamanaka et al., Astrocytes as determinants of disease progression in inherited amyotrophic lateral sclerosis. Nat Neurosci. Mar. 2008;11(3):251-3. doi: 10.1038/nn2047. Epub Feb. 3, 2008.

Yang et al., The muscle-specific microRNA miR-1 regulates cardiac arrhythmogenic potential by targeting GJA1 and KCNJ2. Nat Med. Apr. 2007;13(4):486-91. Epub Apr. 1, 2007. Erratum in: Nat Med. Dec. 2011;17(12):1693.

Yu et al., let-7 regulates self renewal and tumorigenicity of breast cancer cells. Cell. Dec. 14, 2007;131(6):1109-23.

Zhang et al., Characterization of 12 AAV vectors for intravascular delivery to target CNS and detarget non-CNS tissues by mirna regulation: implications in treatment of canavan disease. Molecular Therapy. May 2010;18(1): S174. Abstract 450.

Zhang et al., Efficient inhibition of HIV-1 replication by an artificial polycistronic miRNA construct. Virol J. Jun. 18, 2012:9:118. doi: 10.1186/1743-422X-9-118.

Zhong et al., Chimpanzee-derived novel natural variants of aav9: vector development and interrogation of correlations between capsid structure and vector biology. Molecular Therapy. May 2010;18(1): S24. Abstract 58.

Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.

Zolotukhin et al., Production and purification of serotype 1, 2, and 5 recombinant adeno-associated viral vectors. Methods. Oct. 2002;28(2):158-67.

Zu et al., RAN proteins and RNA foci from antisense transcripts in C9ORF72 Als and frontotemporal dementia. Proc Natl Acad Sci U S A. 2013;110(51):E4968-E4977. doi:10.1073/pnas.1315438110.

Extended European Search Report for Application No. 24170036.8, mailed Oct. 28, 2024 (U0120.70061EP02).

No Author Listed, Score result for SEQ 3 of U.S. Appl. No. 18/505,163 relating to US20160230172A1, filed Apr. 13, 2016. 1 page. Last accessed: May 12, 2025.

Chatterjee-Kishore et al., Exploring the sounds of silence: RNAi-mediated gene silencing for target identification and validation. Drug Discov Today. Nov. 15, 2005;10(22):1559-65. doi: 10.1016/S1359-6446(05)03623-8.

Crooke et al., Mechanisms of Antisense Drug Action, an Introduction. Chapter 1 in: Antisense Drug Technology. 2nd Edition. CRC Press, eds. 2008. DOI: 10.1201/9780849387951. 54 pages.

Gao et al., Adeno-associated viruses undergo substantial evolution in primates during natural infections. Proc Natl Acad Sci USA. May 13, 2003;100(10):6081-6. doi: 10.1073/pnas.0937739100. Epub Apr. 25, 2003.

Gao et al., Clades of Adeno-associated viruses are widely disseminated in human tissues. J Virol. Jun. 2004;78(12):6381-8. doi: 10.1128/JVI.78.12.6381-6388.2004.

Martier et al., Artificial MicroRNAs Targeting C9orf72 Can Reduce Accumulation of Intra-nuclear Transcripts in ALS and FTD Patients. Mol Ther Nucleic Acids. Mar. 1, 2019:14:593-608. doi: 10.1016/j.omtn.2019.01.010. Epub Jan. 30, 2019.

Sasaki et al., Argonaute: The Structural Basis of RNA Silencing. RegionFusion Review. Sep. 2012; 1: e001. DOI: 10.7875/leading.author.1.e001.

* cited by examiner

| Av Ct | SET 1 | SET 2 | SET 3 |
|---|---|---|---|
| miR220 | 20.91 | 25.91 | 27.35 |
| miR SOD | 19.80 | 24.88 | 28.81 |
| GAPDH | 13.42 | 14.22 | 16.44 |
| | 14.21 | 14.76 | 20.32 |

```
5' UG |                    AU              UUGGCC
   CUGAUGAACAUGGA   CCAUGCAGGUU                 \
   ||||||||||||||   |||||||||||              A
   GACUACUUGUACCU__GGUACGUCCAG               /
3' AG |                    UCAGUC
```

AAVrh10 VECTOR CONSTRUCTS

PROMOTERS: CB (CHICKEN BETA ACTIN) AND U6
CMVE: CMV ENHANCER
CARGO: GFP OR ANTI-SOD1 microRNA (miR)

| rAAV CONSTRUCT | CB6-GFP | CB6-GFP-127miRNA | U6-127miRNA-GFP |
|---|---|---|---|
| NUMBER OF ANIMALS | 3 MARMOSETS UNDER 4 YEARS OF AGE | 3 MARMOSETS UNDER 4 YEARS OF AGE | 3 MARMOSETS UNDER 4 YEARS OF AGE |
| VECTOR ROUTE OF DELIVERY AND VOLUME | AAVRh10 INTRATHECAL (300UL) | AAVRh10 INTRATHECAL (300UL) | AAVRh10 INTRATHECAL (300UL) |
| TOTAL rAAV DOSE | $3 \times 10^{12}$ VECTOR PARTICLES (VP) | $3 \times 10^{12}$ VECTOR PARTICLES | $3 \times 10^{12}$ VECTOR PARTICLES |
| APPROX. NHP WEIGHT | 400-500 GRAMS | 400-500 GRAMS | 400-500 GRAMS |
| APPROX. DOSE/WEIGHT | $6 \times 10^{12}$ VP/KILOGRAM | $6 \times 10^{12}$ VP/KILOGRAM | $6 \times 10^{12}$ VP/KILOGRAM |
| PROMOTER DRIVING GFP | CHICKEN/BETA ACTIN HYBRID WITH PROMEGA (INTRON) | CHICKEN/BETA ACTIN HYBRID WITH PROMEGA (INTRON) | CHICKEN/BETA ACTIN HYBRID WITH SV40 (INTRON) |
| PROMOTER DRIVING miRNA | POLYMERASE II (SAME AS ABOVE) | POLYMERASE II (SAME AS ABOVE) | POLYMERASE III (U6 PROMOTER) |

FIG. 14

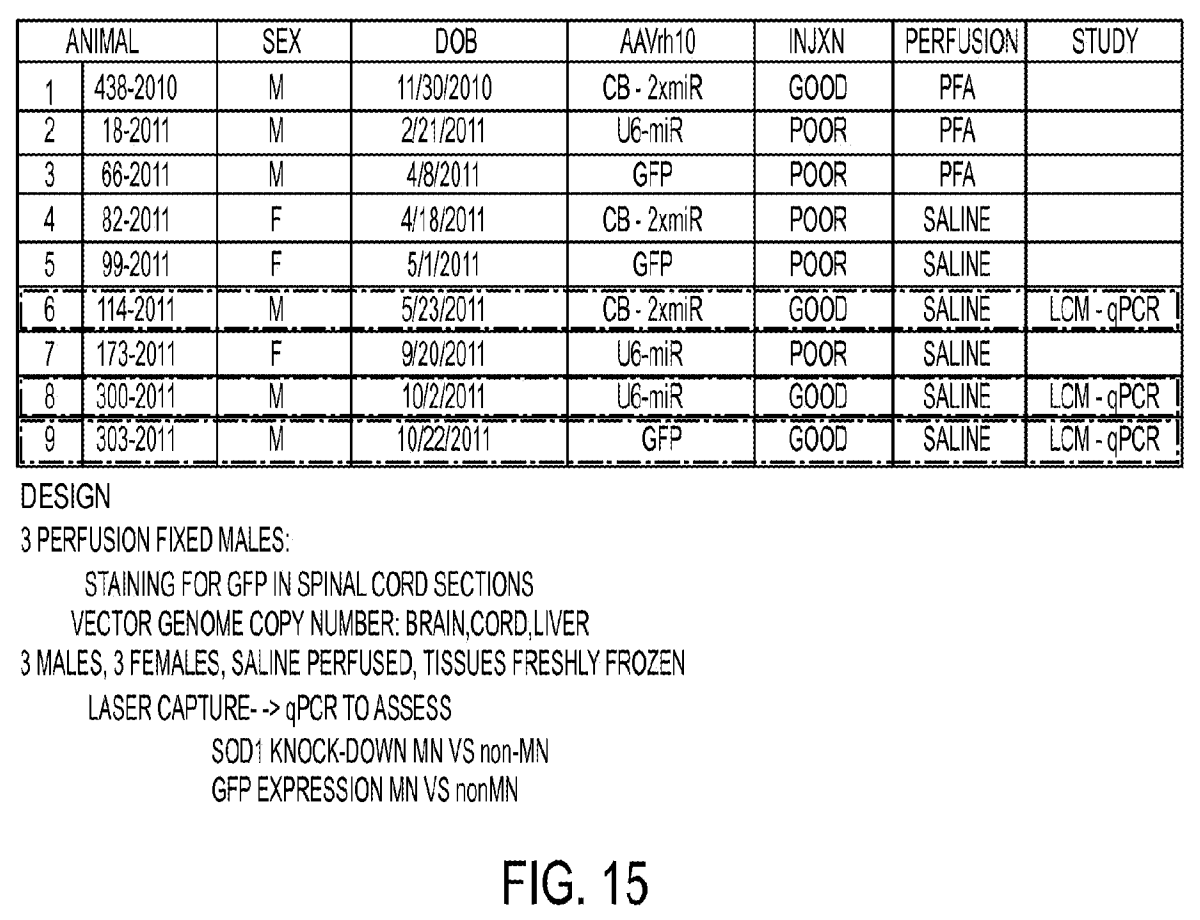

| | ANIMAL | SEX | DOB | AAVrh10 | INJXN | PERFUSION | STUDY |
|---|---|---|---|---|---|---|---|
| 1 | 438-2010 | M | 11/30/2010 | CB - 2xmiR | GOOD | PFA | |
| 2 | 18-2011 | M | 2/21/2011 | U6-miR | POOR | PFA | |
| 3 | 66-2011 | M | 4/8/2011 | GFP | POOR | PFA | |
| 4 | 82-2011 | F | 4/18/2011 | CB - 2xmiR | POOR | SALINE | |
| 5 | 99-2011 | F | 5/1/2011 | GFP | POOR | SALINE | |
| 6 | 114-2011 | M | 5/23/2011 | CB - 2xmiR | GOOD | SALINE | LCM - qPCR |
| 7 | 173-2011 | F | 9/20/2011 | U6-miR | POOR | SALINE | |
| 8 | 300-2011 | M | 10/2/2011 | U6-miR | GOOD | SALINE | LCM - qPCR |
| 9 | 303-2011 | M | 10/22/2011 | GFP | GOOD | SALINE | LCM - qPCR |

DESIGN

3 PERFUSION FIXED MALES:

STAINING FOR GFP IN SPINAL CORD SECTIONS

VECTOR GENOME COPY NUMBER: BRAIN,CORD,LIVER

3 MALES, 3 FEMALES, SALINE PERFUSED, TISSUES FRESHLY FROZEN

LASER CAPTURE--> qPCR TO ASSESS

SOD1 KNOCK-DOWN MN VS non-MN

GFP EXPRESSION MN VS nonMN

FIG. 15

RAAV-BASED COMPOSITIONS AND METHODS FOR TREATING AMYOTROPHIC LATERAL SCLEROSIS

RELATED APPLICATIONS

This application is a divisional under 35 U.S.C. § 120 of U.S. patent application Ser. No. 17/174,452, filed Feb. 12, 2021, which is a continuation under 35 U.S.C. § 120 of U.S. patent application Ser. No. 16/295,621, filed Mar. 7, 2019, which is a continuation under 35 U.S.C. § 120 of U.S. patent application Ser. No. 15/126,688, filed Sep. 16, 2016, which is a National Stage Application of PCT/US2015/021321, filed Mar. 18, 2015, which claims the benefit under 35 U.S.C. § 119 (e) of the filing date of U.S. Provisional Patent Application Ser. No. 61/955,189, filed Mar. 18, 2014, each of which applications is incorporated by reference herein in its entirety.

REFERENCE TO AN ELECTRONIC SEQUENCE LISTING

The contents of the electronic sequence listing (U012070061US06-SUBSEQ-SCC.xml; Size: 39,896 bytes; and Date of Creation: Jul. 1, 2025) is herein incorporated by reference in its entirety.

FIELD OF THE INVENTION

The invention relates to methods and compositions for treating genetic disease, such as Amyotrophic Lateral Sclerosis.

BACKGROUND OF THE INVENTION

Amyotrophic lateral sclerosis (ALS) is a progressive, generally fatal motor neuron disorder that sometimes develops concurrently with frontotemporal dementia (FTD). ALS is encountered in both sporadic (SALS) and familial (FALS) forms. About 10% of cases are transmitted as autosomal dominant traits. An FDA-approved therapy for ALS is riluzole, a compound that prolongs survival by about 10%.

SUMMARY OF THE INVENTION

Aspects of the disclosure relate to compositions and methods for modulating expression of genes associated with amyotrophic lateral sclerosis (ALS). In particular, inhibitory nucleic acids are provided that are useful for silencing of genes, such as C9orf72 and SOD1, which are associated with ALS. For example, in some aspects of the disclosure inhibitory nucleic acids are provided that target all variants of C9orf72. In other aspects of the disclosure, inhibitory nucleic acids are provided that target a subset of variants of C9orf72. Some embodiments of the disclosure relate to a recognition that, although certain inhibitory nucleic acids, such as miRNAs, generally function in the cytoplasm, they can be loaded onto Argonaut protein (e.g., AGO2, the catalytic component of RNA induced silencing complex or RISC) in the cytoplasm and imported back into the nucleus where they can silence pre-mRNA. Thus, in some embodiments, inhibitory nucleic acids (e.g., miRNAs) are provided that are capable of targeting both the RNA within the nucleus and the RNA in the cytoplasm to prevent or inhibiting RNA function, including protein translation.

Aspects of the disclosure relate to treatment methods that utilize intrathecal delivery of AAVs engineered to express inhibitory nucleic acids that silence genes, such as C9orf72 and SOD1, which are associated with ALS. In some embodiments, methods are provided for delivering nucleic acids that utilize neurotropic AAVs, such as AAV9 and AAV.Rh10, to target CNS tissue. The use of AAVs harboring nucleic acids that are engineered to express inhibitory nucleic acids is advantageous in part because it overcomes deficiencies associated with having to re-administer non-expressed inhibitory nucleic acids, such as, e.g., siRNA duplexes and antisense oligonucleotides, since the rAAV episomes will continually express the inhibitory nucleic acids (e.g., miRNA). Moreover, in some embodiments, methods provided herein are advantageous because they allow for the use of relatively low doses of AAVs for silencing genes in the CNS and minimize the exposure of peripheral tissues to the AAVs.

In other aspects of the disclosure, transgenic mice are provided that contain a C9orf72 $G_4C_2$ expansion. In some embodiments, the model facilitates assessment of inhibitory nucleic acids for C9orf72 gene silencing in vitro as well as in vivo in a mammalian CNS. In other aspects, the use of RAN-translated peptides is disclosed as markers, e.g., for C9orf72 activity. In some embodiments, the transgenic mouse model facilitates assessment of persistence in the CNS of neurotrophic AAVs, such as AAVs harboring an Rh10 capsid. In some embodiments, the transgenic mouse model facilitates assessment of incipient immunogenicity following administration, e.g., via intrathecal delivery.

In some aspects, the disclosure provides a method of inhibiting C9orf72 expression in a cell, the method comprising delivering to the cell an inhibitory nucleic acid that targets both pre-mRNA and mRNA encoded by a C9orf72 gene.

In some embodiments, the cell expresses C9orf72 having $G_4C2$ expansions of up to 50, up to 90, up to 160, or up to 200 repeats. In some embodiments, the level of a mRNA encoding isoform B of C9orf72 in the cell is greater than the level of a mRNA encoding isoform A of C9orf72 protein in the cell.

In some embodiments, the cell is a cell of the central nervous system. In some embodiments, the cell is a neuron.

In some embodiments, prior to being exposed to the inhibitory nucleic acid, the cell contains intranuclear $G_4C2$ foci. In some embodiments, delivery of the inhibitory nucleic acid to the cell results in a reduction in intranuclear $G_4C2$ foci.

In some embodiments, prior to being exposed to the inhibitory nucleic acid, the cell contains C9 RAN proteins. In some embodiments, delivery of the inhibitory nucleic acid to the cell results in a reduction in C9 RAN protein levels.

In some embodiments, the cell is in vivo. In some embodiments, the cell is in vitro. In some embodiments, the cell is of a subject having one or more symptoms of FTD or ALS. In some embodiments, the cell is of a subject suspected of having FTD or ALS.

In some aspects, the disclosure provides a method of inhibiting C9orf72 expression in the central nervous system (CNS) of a subject, the method comprising administering to the CNS of the subject an inhibitory nucleic acid that targets an RNA encoded by the C9orf72 gene, wherein the inhibitory nucleic acid is a microRNA.

In some aspects, the disclosure provides a method of inhibiting C9orf72 expression in the central nervous system (CNS) of a subject, the method comprising administering to the CNS of the subject an inhibitory nucleic acid that targets both pre-mRNA and mRNA encoded by a C9orf72 gene.

In some embodiments, the inhibitory nucleic acid is a microRNA.

In some embodiments, the step of administering the inhibitory nucleic acid to the subject comprises administering to the subject a recombinant adeno-associated virus (rAAV) harboring a nucleic acid that is engineered to express the inhibitory nucleic acid in a cell of the subject.

In some aspects, the disclosure provides a method of treating a subject having or suspected of having FTD or ALS, the method comprising administering to the subject an effective amount of a recombinant adeno-associated virus (rAAV) harboring a nucleic acid that is engineered to express, in a cell of the subject, an inhibitory nucleic acid that targets both pre-mRNA and mRNA encoded by a C9orf72 gene.

In some embodiments, the rAAV targets CNS tissue. In some embodiments, the rAAV comprises an AAV.Rh10 or AAV9 capsid protein.

In some embodiments, the inhibitory nucleic acid comprises a region of complementarity that is complementary with at least 5 consecutive nucleotides within exon 3 of C9orf72. In some embodiments, the at least 5 consecutive nucleotides are within nucleotides 220 to 241 of C9orf72.

In some embodiments, the inhibitory nucleic acid targets mRNA encoding isoform A and mRNA encoding isoform B of C9orf72 protein. In some embodiments, the inhibitory nucleic acid targets C9orf72 variants V1 (NM_145005.6; SEQ ID NO: 18), V2 (NM_018325.3; SEQ ID NO: 19), and V3 (NM_001256054.1; SEQ ID NO: 20). In some embodiments, the inhibitory nucleic acid targets C9orf72 variants V1 (NM_145005.6; SEQ ID NO: 18) and V3 (NM_001256054.1; SEQ ID NO: 20), but not V2 (NM_018325.3; SEQ ID NO: 19). In some embodiments, the inhibitory nucleic acid targets C9orf72 variant V1 (NM_145005.6; SEQ ID NO: 18), but not V2 (NM_018325.3; SEQ ID NO: 19) and V3 (NM_001256054.1; SEQ ID NO: 20).

In some embodiments, the inhibitory nucleic acid reduces levels of C9orf72 mRNA in a cell by at least 50%. In some embodiments, the inhibitory nucleic acid reduces levels of C9orf72 pre-mRNA in a cell by at least 50%.

In some embodiments, the inhibitory nucleic acid comprises 5, 6, 7, 8, 9, 10, 11, 12, 13, 14, 15, 16, 17, 18, 19, 20 or 21 consecutive nucleotides of a sequence as set forth in any one of SEQ ID NOs: 1 to 8. In some embodiments, the rAAV is administered by intrathecally, intracerebrally, intraventricularly or intravenously.

In some aspects, the disclosure provides a method of inhibiting SOD1 expression in a cell, the method comprising delivering to the cell an miRNA that targets SOD1 mRNA, wherein the miRNA comprises 5, 6, 7, 8, 9, 10, 11, 12, 13, 14, 15, 16, 17, 18, 19, 20 or 21 consecutive nucleotides of a sequence as set forth in:

```
SEQ ID NO: 15:
AGCATTAAAGGACTGACTGAA (SOD-miR-103);

SEQ ID NO: 16:
GACTGAAGGCCTGCATGGATT (SOD-miR-117);
or

SEQ ID NO: 17:
CTGCATGGATTCCATGTTCAT (SOD-miR-127).
```

In some aspects, the disclosure provides a method of treating a subject having or suspected of having ALS, the method comprising administering to the subject an effective amount of a recombinant adeno-associated virus (rAAV)

harboring a nucleic acid that is engineered to express, in a cell of the subject, an miRNA that targets RNA encoded by a SOD1 gene.

In some embodiments, the miRNA comprises 5, 6, 7, 8, 9, 10, 11, 12, 13, 14, 15, 16, 17, 18, 19, 20 or 21 consecutive nucleotides of a sequence as set forth in:

```
SEQ ID NO: 15:
AGCATTAAAGGACTGACTGAA (SOD-miR-103);

SEQ ID NO: 16:
GACTGAAGGCCTGCATGGATT (SOD-miR-117);
or

SEQ ID NO: 17:
CTGCATGGATTCCATGTTCAT (SOD-miR-127).
```

In some embodiments, the rAAV targets CNS tissue. In some embodiments, the rAAV comprises an AAV.Rh10 or AAV9 capsid protein.

In some aspects, the disclosure provides a synthetic microRNA comprising a sequence as set forth in any one of SEQ ID NOs: 1 to 8.

In some aspects, the disclosure provides a synthetic microRNA comprising a sequence as set forth as SEQ ID NO: 15: AGCATTAAAGGACTGACTGAA (SOD-miR-103); SEQ ID NO: 16: GACTGAAGGCCTGCATGGATT (SOD-miR-117); or SEQ ID NO: 17: CTGCATGGATTC-CATGTTCAT (SOD-miR-127). In some embodiments, the synthetic microRNA further comprise flanking regions of miR-155.

In some aspects, the disclosure provides recombinant nucleic acid encoding the microRNA as set forth in any one of SEQ ID NO: 1 to 8 or SEQ ID NO: 15 to 17 and comprising an inverted terminal repeats (ITR) of an AAV serotype. In some embodiments, the AAV serotype is selected from the group consisting of: AAV1, AAV2, AAV5, AAV6, AAV6.2, AAV7, AAV8, AAV9, AAVRh10, AAV11 and variants thereof.

In some embodiments, the recombinant nucleic acid further comprises a promoter operably linked with a region(s) encoding the microRNA. In some embodiments, the promoter is a tissue-specific promoter. In some embodiments, the promoter is a polymerase II promoter, such as a β-actin promoter. In some embodiments, the promoter is a polymerase III promoter, such as a U6 promoter.

In some aspects, the disclosure provides a composition comprising a recombinant nucleic acid as described by the disclosure.

In some aspects, the disclosure provides a recombinant Adeno-Associated Virus (AAV) harboring a recombinant nucleic acid as described by the disclosure. In some embodiments, the recombinant AAV further comprises one or more capsid proteins of one or more AAV serotypes selected from the group consisting of: AAV1, AAV2, AAV3, AAV4, AAV5, AAV6, AAV7, AAV8, AAV9, AAV.Rh10, AAV11 and variants thereof.

In some aspects, the disclosure provides a composition comprising a recombinant AAV as described by the disclosure. In some embodiments, the composition further comprises a pharmaceutically acceptable carrier.

In some aspects, the disclosure provides a kit comprising a container housing a composition as described by the disclosure.

BRIEF DESCRIPTION OF THE DRAWINGS

FIG. 1A represents the genomic organization of the gene; the lower panels are pre-mRNA variants 1-3. The boxes represent exons and the lines are introns. The hexanucleotide repeat expansion (red diamond) is transcribed in variants 1 and 3. The ATG start codon and TAA stop codon are as shown. A horizontal line represents the open reading frame for each variant (note that variants 2 and 3 produce the same protein). FIG. 1A shows the locations of the TaqMan primers used to distinguish the pre-mRNA isoforms; FIG. 1B shows the three spliced mRNAs are shown; figure annotations as above with the positions of the primer pairs that detect the three different spliced mRNA isoforms.

FIG. 6D shows motor neurons were laser captured from the lumbar spinal of control (rAAV.Rh10.GFP) and treated (rAAV.Rh10.GFP-miR-SOD1) marmosets and assayed for levels of miR-SOD1 microRNA and SOD1 mRNA RT-qPCR.

FIG. 7A shows the targeting miRNA sequences are cloned into a stem-loop, which is flanked by pri-miRNA sequences of miR-155. Sequence shown corresponds to SEQ ID NO: 25. FIG. 7B shows the sequence targeting the C9-miRs are then cloned into proviral AAV plasmids with either a polymerase II (chicken β-actin) or polymerase III (U6) promoters for in vitro testing and rAAV packaging.

FIG. 10A shows specificity of antibodies was confirmed by Western blot analysis using lysates from cells transfected to express GFP-tagged (GA) 5, (GR) 5, (GP) 5, (PA) 5 or (PR) 5. FIG. 10B shows Anti-GA, anti-GR and anti-GP immunoreactive inclusions are detected throughout the brain of C9FTD/ALS, including in the cerebellum, as shown here.

FIG. 11A shows the sequence targeting the hSOD1 mRNA was cloned into the miR-155 backbone (SEQ ID NO: 21). FIG. 11B shows two tandem copies of this miRNA were cloned into a vector that expresses either GFP or vector that only expresses the miRNAs, as would be desired in the clinical setting. FIG. 11C shows an alignment of the human, Rhesus and Marmoset SOD1 gene sequences showing that the mature miR-SOD1-127 is targeting a sequence that is 100% conserved among the primates (SEQ ID NOs: 22-24 and 17 top to bottom).

FIG. 12A shows newborn mice were administered $1.0 \times 10^{12}$ particles of either a GFP control vector or one expressing the SODImiR-127 via the facial vein. Mice were sacrificed 4 weeks after delivery and the muscle was analyzed for total hSOD1 expression by quantitative real-time RT-PCR. FIG. 12B shows adult mice were injected with $5 \times 10^{10}$ vector particles directly into the striatum. Mice were sacrificed 3 weeks after injection and the brain tissue was analyzed for hSOD1 expression by quantitative real-time RT-PCR.

FIG. 14 outlines assays performed to assess silencing of SOD1 in marmosets.

FIG. 15 is an overview of assays conducted in marmosets.

FIG. 17A shows SOD1 expression was reduced in MNs and non-MNs by IT AAV.Rh10 CB-2×-miR-SOD1 (light grey) and U6-miR-SOD1 (dark gray). The U6 construct produced greater knock-down. FIG. 17B shows relative GFP expression in MNs and non-MNs by IT rAAV.Rh10 CB-2×-mir-SOD1 and U6-miR-SOD1. The U6 construct produced the highest GFP expression.

DETAILED DESCRIPTION

Aspects of the disclosure relate to compositions and methods for modulating expression of genes associated with amyotrophic lateral sclerosis (ALS). Aspects of the disclosure relate to improved gene therapy compositions and related methods for treating ALS using the recombinant adeno-associated viral (rAAV) vectors. In particular, rAAVs are provided that harbor nucleic acids engineered to express inhibitory nucleic acids that silence genes, such as C9orf72 and SOD1, which are associated with ALS. In some embodiments, the disclosure utilizes a recombinant AAV (e.g., rAAV.Rh10) to deliver a microRNA to the CNS and thereby silence an ALS gene, such as SOD1 or C9orf72.

Figure 1A:
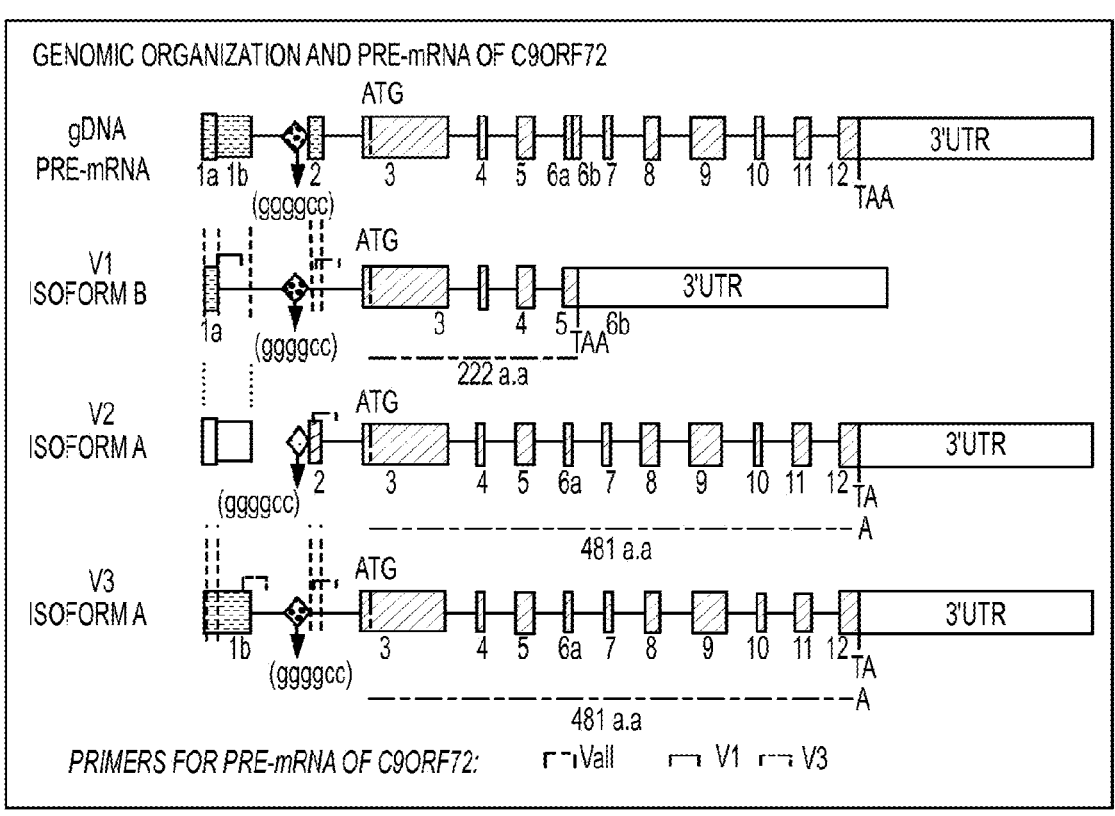
FIGS. 1A-1B provide a diagram of C9orf72 gene and primers.
Figure 1B:
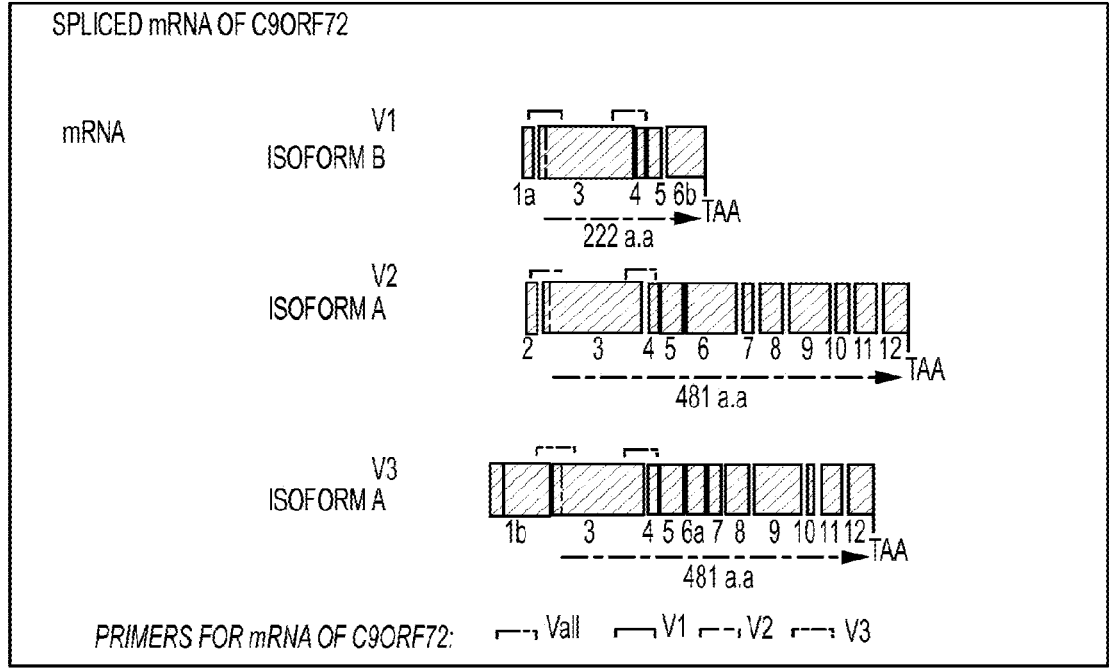

ALS occurs in both familial (FALS) and sporadic (SALS) forms. A significant number of FALS cases are associated with expansions of a non-coding hexanucleotide $G_4C_2$ expansion in the gene C9orf72. These expansions are also detected in 10-20% of familial frontotemporal dementia (FTD), 10% of sporadic FTD and in ~5% of SALS. These statistics define the C9orf72 $G_4C_2$ expansion as a common cause of ALS. In normal individuals, the $G_4C_2$ expansion ranges in size from 2 or 3 to upwards of 25 repeats; by contrast, FTD/ALS patients have hundreds or even thousands of these repeats. Transcription from the normal C9orf72 gene yields three mRNA variants V1 (e.g., Genbank: NM_145005.6; SEQ ID NO: 18), V2 (e.g., Genbank: NM_018325.3; SEQ ID NO: 19), and V3 (e.g., Genbank: NM_001256054.1; SEQ ID NO: 20). Transcript V1 contains exons 1a-6b and codes for a 222 amino acid protein. Exons V2 and V3 respectively contain exons 2-12 and exons 1b-12 and code for the same 48laa protein (FIG. 1).

Aspects of the disclosure relate to a recognition that V1 and V3 harbor the $G_4C_2$ expansion. Analysis of human ALS and FTD brains with this expansion has shown intranuclear accumulation of the RNA transcripts, generating RNA intranuclear foci in the frontal cortex and spinal cord. This supports that the expansion in transcripts V1 and V3 is a primary adverse agent causing cytotoxicity in motor neurons. While the functions of the proteins encoded by C9orf72 are not well characterized, bioinformatics approaches indicate that the C9orf72 protein shares structural features with (DENN) and GDP/GTP exchange factors (GEF) 4 and so may regulate membrane cell trafficking among other potential functions. Cytotoxicity of the $G_4C_2$ expansions may be associated with one or more gain-of-function mechanisms, such as, for example: 1) excessive sequestering by the RNA foci of transcription factors (like muscleblind in myotonic dystrophy); 2) repeat-associated non-ATG (RAN) translation of the expanded repeat, leading to expression of dipeptides (Gly-Ala; Gly-Pro; Gly-Arg); the peptides produced in this fashion form neuronal inclusions throughout the CNS; (3) and induction of haploinsufficiency due to decreased C9orf72 transcript expression. Aspects of the disclosure relate to the use of rAAV (e.g., intrathecally-delivered rAAV.Rh10) to introduce an inhibitory nucleic acid (e.g., a microRNA) to silence expression of the transcripts of C9orf72 that harbor the offending $G_4C_2$ expansion. In some embodiments, the disclosure provides methods and compositions that achieve silence key pre-mRNA and mature mRNA transcripts of C9orf72 in vitro.

Mutations in the gene encoding Superoxide dismutase (SOD1), located on chromosome 21, have been linked to familial amyotrophic lateral sclerosis. Superoxide dismutase (SOD1) is an enzyme encoded by the SOD1 gene. SOD1 binds copper and zinc ions and is one of three superoxide dismutases responsible for destroying free superoxide radicals in the body. The encoded isozyme is a soluble cytoplasmic and mitochondrial intermembrane space protein, acting as a homodimer to convert naturally occurring, but harmful, superoxide radicals to molecular oxygen and hydrogen peroxide.

Frequent SOD1 mutations that occur and cause ALS include A4V, H46R and G93A. Typically, these ALS-causing SOD1 mutations act in a dominant fashion, such that a single mutant copy of the SOD1 gene may be sufficient to cause the disease. It is believed that they mutations result in a toxic gain of function as the mutant enzymes typically retain enzymatic activity. Accordingly, mutant SOD1 can cause a wide range of cellular defects including mitochondrial dysfunctions, oxidative stress, calcium misregulation, aggregation of aberrantly processed proteins, endoplasmic reticulum (ER) stress, axonal transport disruption, neurotransmitter misregulation, programmed cell death and inflammation. Aspects of the disclosure relate to the use of rAAV (e.g., rAAV.Rh10) to introduce an inhibitory nucleic acid (e.g., a microRNA) into cells to silence expression of mutant SOD1.

Inhibitory Nucleic Acids

In some embodiments, the disclosure provides inhibitory nucleic acids that inhibit expression of genes that cause ALS, such as SOD1 and C9orf72. In some embodiments, the inhibitory nucleic acid is a nucleic acid that hybridizes to at least a portion of the target nucleic acid, such as an RNA, pre-mRNA, mRNA, and inhibits its function or expression. In some embodiments, the inhibitory nucleic acid is single stranded or double stranded. In some embodiments, the inhibitory nucleic acid is a microRNA (miRNA). In some embodiments, the inhibitory nucleic acid is a microRNA comprising a targeting sequence having flanking regions of miR-155.

In some embodiments, the inhibitory nucleic acid is 5 to 30 bases in length (e.g., 10-30, 15-25, 19-22). The inhibitory nucleic acid may also be 10-50, or 5-50 bases length. For example, the inhibitory nucleic acid may be one of any of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 bases in length. In some embodiments, the inhibitory nucleic acid comprises or consists of a sequence of bases at least 80% or 90% complementary to, e.g., at least 5, 10, 15, 20, 25 or 30 bases of, or up to 30 or 40 bases of, the target nucleic acid, or comprises a sequence of bases with up to 3 mismatches (e.g., up to 1, or up to 2 mismatches) over 10, 15, 20, 25 or 30 bases of the target nucleic acid.

In some embodiments, any one or more thymidine (T) nucleotides or uridine (U) nucleotides in a sequence provided herein may be replaced with any other nucleotide suitable for base pairing (e.g., via a Watson-Crick base pair) with an adenosine nucleotide. For example, T may be replaced with U, and U may be replaced with T. In some embodiments, inhibitory nucleic acids are provided that inhibit expression of genes in a cell of the central nervous system. In some embodiments, the cell is a neuron, astrocyte, or oligodendrocyte.

In some embodiments, the cell expresses C9orf72 having $G_4C_2$ expansions of up to 50, up to 90, up to 160, up to 200, up to 300, up to 400, up to 500 repeats, up to 600 repeats or more. In some embodiments, the inhibitory nucleic acid comprises a sequence as set forth in any one of SEQ ID NOs: 1 to 8. In some embodiments, the level of a mRNA encoding isoform B of C9orf72 in the cell is greater than the level of a mRNA encoding isoform A of C9orf72 protein in the cell. In some embodiments, the cell contains detectable levels of intranuclear $G_4C_2$ foci. In some embodiments, the cell contains detectable levels of C9 RAN proteins.

In some embodiment, the cell expresses a mutant SOD1enzyme. In some embodiments, the SOD1 mutation is selected from: A4V, H46R and G93A. In some embodiments, the inhibitory nucleic acid comprises or consists of a sequence as set forth at

```
SEQ ID NO: 15:
AGCATTAAAGGACTGACTGAA (SOD-miR-103);

SEQ ID NO: 16:
GACTGAAGGCCTGCATGGATT (SOD-miR-117);
or

SEQ ID NO: 17:
CTGCATGGATTCCATGTTCAT (SOD-miR-127).
```

Methods of Use

Methods are provided herein for inhibiting the expression of genes that are associated with FTD and/or ALS, such as C9orf72 or SOD1. In some embodiments, methods are provided for inhibiting the expression of C9orf72 in a cell that involve delivering to the cell an inhibitory nucleic acid that targets both pre-mRNA and mRNA encoded by a C9orf72 gene. In some embodiments, methods are provided for inhibiting the expression of C9orf72 in a cell that involve administering to the CNS of the subject an inhibitory nucleic acid that targets an RNA encoded by the C9orf72 gene, wherein the inhibitory nucleic acid is a microRNA.

In some embodiments, methods are provided for inhibiting C9orf72 expression in the central nervous system (CNS) of a subject. In some embodiments, the methods involve administering to the CNS of the subject an inhibitory nucleic acid that targets both pre-mRNA and mRNA encoded by a C9orf72 gene. In some embodiments, the subject has or is suspected of having FTD or ALS. In some embodiments, the methods involve administering to the subject an effective amount of a recombinant adeno-associated virus (rAAV) harboring a nucleic acid that is engineered to express, in a cell of the subject, an inhibitory nucleic acid that targets both pre-mRNA and mRNA encoded by a C9orf72 gene. In some embodiments, the inhibitory nucleic acid comprises a sequence as set forth in any one of SEQ ID NOs: 1 to 8.

In some embodiments, methods are provided for inhibiting SOD1 expression in a cell. In some embodiments, the methods involve delivering to the cell an miRNA that targets SOD1 mRNA, wherein the miRNA comprises 5, 6, 7, 8, 9, 10, 11, 12, 13, 14, 15, 16, 17, 18, 19, 20 or 21 consecutive nucleotides of a sequence as set forth in:

```
SEQ ID NO: 15:
AGCATTAAAGGACTGACTGAA (SOD-miR-103);

SEQ ID NO: 16:
GACTGAAGGCCTGCATGGATT (SOD-miR-117);
or

SEQ ID NO: 17:
CTGCATGGATTCCATGTTCAT (SOD-miR-127),
``` or of a complementary sequence of any one of them. In some embodiments, the SOD1 mRNA is set forth in GenBank: EF151142.1.

In some embodiments, methods are provided for treating a subject having or suspected of having ALS. In some embodiments, the methods involve administering to the subject an effective amount of a recombinant adeno-associated virus (rAAV) harboring a nucleic acid that is engineered to express, in a cell of the subject, an miRNA that targets RNA encoded by a SOD1 gene.

In accordance with the foregoing, certain methods provided herein involve administering to a subject an effective amount of a recombinant Adeno-Associated Virus (rAAV) harboring any of the recombinant nucleic acids disclosed herein. In general, the "effective amount" of a rAAV refers to an amount sufficient to elicit the desired biological response. In some embodiments, the effective amount refers to the amount of rAAV effective for transducing a cell or tissue ex vivo. In other embodiments, the effective amount refers to the amount effective for direct administration of rAAV to a subject. As will be appreciated by those of ordinary skill in this art, the effective amount of the recombinant AAV of the invention varies depending on such factors as the desired biological endpoint, the pharmacokinetics of the expression products, the condition being treated, the mode of administration, and the subject. Typically, the rAAV is administered with a pharmaceutically acceptable carrier.

In some instances, after administration of the rAAV at least one clinical outcome parameter or biomarker (e.g., intranuclear $G_4C_2$ RNA foci, RAN-protein expression, etc.) associated with the FTD or ALS is evaluated in the subject. Typically, the clinical outcome parameter or biomarker evaluated after administration of the rAAV is compared with the clinical outcome parameter or biomarker determined at a time prior to administration of the rAAV to determine effectiveness of the rAAV. Often an improvement in the clinical outcome parameter or biomarker after administration of the rAAV indicates effectiveness of the rAAV. Any appropriate clinical outcome parameter or biomarker may be used. Typically, the clinical outcome parameter or biomarker is indicative of the one or more symptoms of an FTD or ALS. For example, the clinical outcome parameter or biomarker may be selected from the group consisting of:

intranuclear $G_4C_2$ RNA foci, RAN-protein expression, SOD1 expression, C9orf72 expression, memory loss, and presence or absence of movement disorders such as unsteadiness, rigidity, slowness, twitches, muscle weakness or difficulty swallowing, speech and language difficulties, twitching (fasciculation) and cramping of muscles, including those in the hands and feet.

Recombinant AAVs

In some aspects, the invention provides isolated AAVs. As used herein with respect to AAVs, the term "isolated" refers to an AAV that has been isolated from its natural environment (e.g., from a host cell, tissue, or subject) or artificially produced. Isolated AAVs may be produced using recombinant methods. Such AAVs are referred to herein as "recombinant AAVs". Recombinant AAVs (rAAVs) may have tissue-specific targeting capabilities, such that a transgene of the rAAV is delivered specifically to one or more predetermined tissue(s). The AAV capsid is an important element in determining these tissue-specific targeting capabilities. Thus, a rAAV having a capsid appropriate for the tissue being targeted can be selected. In some embodiments, the rAAV comprises a capsid protein having an amino acid sequence corresponding to any one of AAV1, AAV2, AAV3, AAV4, AAV5, AAV6, AAV7, AAV8, AAV9, AAV.Rh10, AAV11 and variants thereof. The recombinant AAVs typically harbor an recombinant nucleic acid of the invention.

Methods for obtaining recombinant AAVs having a desired capsid protein are well known in the art (See, for example, U.S. Patent Publication Number 2003/0138772, the contents of which are incorporated herein by reference in their entirety). AAV capsid proteins that may be used in the rAAVs of the invention a include, for example, those disclosed in G. Gao, et al., J. Virol, 78 (12): 6381-6388 (June 2004); G. Gao, et al, Proc Natl Acad Sci USA, 100 (10): 6081-6086 (May 13, 2003); US 2003-0138772, US 2007/0036760, US 2009/0197338, and WO 2010/138263, the contents of which relating to AAVs capsid proteins and associated nucleotide and amino acid sequences are incorporated herein by reference. Typically the methods involve culturing a host cell which contains a nucleic acid sequence encoding an AAV capsid protein or fragment thereof; a functional rep gene; a recombinant AAV vector composed of AAV inverted terminal repeats (ITRs) and a transgene; and sufficient helper functions to permit packaging of the recombinant AAV vector into the AAV capsid proteins.

Suitable AAVs that may be used in the methods provided herein are disclosed in U.S. Patent Publication Number 2013/0195801, entitled "CNS TARGETING AAV VECTORS AND METHODS OF USE THEREOF," and published on Aug. 1, 2013; and U.S. Patent Publication Number 2012/0137379, entitled "NOVEL AAV'S AND USES THEREOF," and published on May 31, 2012. The contents of these publications are incorporated herein by reference for all purposes.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

The recombinant AAV vector, rep sequences, cap sequences, and helper functions required for producing the rAAV of the invention may be delivered to the packaging host cell using any appropriate genetic element (vector). The selected genetic element may be delivered by any suitable method, including those described herein. The methods used to construct any embodiment of this invention are known to those with skill in nucleic acid manipulation and include genetic engineering, recombinant engineering, and synthetic techniques. Sec, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. Sec, e.g., K. Fisher et al, J. Virol., 70:520-532 (1993) and U.S. Pat. No. 5,478,745.

In some embodiments, recombinant AAVs may be produced using the triple transfection method (e.g., as described in detail in U.S. Pat. No. 6,001,650, the contents of which relating to the triple transfection method are incorporated herein by reference). Typically, the recombinant AAVs are produced by transfecting a host cell with a recombinant AAV vector (comprising a transgene) to be packaged into AAV particles, an AAV helper function vector, and an accessory function vector. An AAV helper function vector encodes the "AAV helper function" sequences (e.g., rep and cap), which function in trans for productive AAV replication and encapsidation. In some embodiments, the AAV helper function vector supports efficient AAV vector production without generating any detectable wild-type AAV virions (e.g., AAV virions containing functional rep and cap genes). Non-limiting examples of vectors suitable for use with the present invention include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (e.g., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the invention provides transfected host cells. The term "transfection" is used to refer to the uptake of foreign DNA by a cell, and a cell has been "transfected" when exogenous DNA has been introduced inside the cell membrane. A number of transfection techniques are generally known in the art. Scc, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

In some aspects, the invention provides isolated cells. As used herein with respect to cell, the term "isolated" refers to a cell that has been isolated from its natural environment (e.g., from a tissue or subject). As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA (e.g., shRNA, miRNA) from a transcribed gene.

The foregoing methods for packaging recombinant vectors in desired AAV capsids to produce the rAAVs of the invention are not meant to be limiting and other suitable methods will be apparent to the skilled artisan.

Recombinant AAV Vectors

The recombinant nucleic acids of the invention may be recombinant AAV vectors. The recombinant AAV vector may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The transgene may comprise, as disclosed elsewhere herein, one or more regions that encode one or more inhibitory nucleic acids (e.g., miRNAs) comprising a nucleic acid that targets an endogenous mRNA of a subject. The transgene may also comprise a region encoding an exogenous mRNA that encodes a protein (e.g., a fluorescent protein).

The AAV sequences of the vector typically comprise the cis-acting 5' and 3' inverted terminal repeat sequences (Sec, e.g., B. J. Carter, in "Handbook of Parvoviruses", ed., P. Tijsser, CRC Press, pp. 155 168 (1990)). The ITR sequences are about 145 bp in length. In some embodiments, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types.

Thus, the recombinant nucleic acids may comprise inverted terminal repeats (ITR) of an AAV serotypes selected from the group consisting of: AAV1, AAV2, AAV5, AAV6, AAV6.2, AAV7, AAV8, AAV9, AAV.Rh10, AAV11 and variants thereof. The recombinant nucleic acids may also include a promoter operably linked with the one or more first inhibitory RNAs, the exogenous mRNA, and/or the one or more second inhibitory RNAs. The promoter may be tissue-specific promoter, a constitutive promoter or inducible promoter.

In addition to the major elements identified above for the recombinant AAV vector, the vector also includes conventional control elements which are operably linked with elements of the transgene in a manner that permits its transcription, translation and/or expression in a cell transfected with the vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (e.g., Kozak consensus sequence); sequences that enhance protein stability; and when desired, sequences that enhance secretion of the encoded product. A number of expression control sequences, including promoters which are native, constitutive, inducible and/or tissue-specific, are known in the art and may be utilized.

As used herein, a nucleic acid sequence (e.g., coding sequence) and regulatory sequences are said to be operably linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., miRNA).

For nucleic acids encoding proteins, a polyadenylation sequence generally is inserted following the transgene sequences and before the 3' AAV ITR sequence. A rAAV construct useful in the present invention may also contain an intron, desirably located between the promoter/enhancer sequence and the transgene. One possible intron sequence is derived from SV-40, and is referred to as the SV-40 T intron sequence. Any intron may be from the B-Actin gene. Another vector element that may be used is an internal ribosome entry site (IRES). The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer), the SV40 promoter, and the dihydrofolate reductase promoter. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system, the ecdysone insect promoter, the tetracycline-repressible system, the tetracycline-inducible system, the RU486-inducible system and the rapamycin-inducible system. Still other types of inducible promoters which may be useful in this context are those which are regulated by a specific physiological state, e.g., temperature, acute phase, a particular differentiation state of the cell, or in replicating cells only. In another embodiment, the native promoter, or fragment thereof, for the transgene will be used. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. In some embodiments, the promoter is a chicken β-actin promoter.

In some embodiments, one or more bindings sites for one or more of miRNAs are incorporated in a transgene of a rAAV vector, to inhibit the expression of the transgene in one or more tissues of a subject harboring the transgenes, e.g., non-liver tissues, non-lung tissues. The skilled artisan will appreciate that binding sites may be selected to control the expression of a transgene in a tissue specific manner. The miRNA target sites in the mRNA may be in the 5' UTR, the 3' UTR or in the coding region. Typically, the target site is in the 3' UTR of the mRNA. Furthermore, the transgene may be designed such that multiple miRNAs regulate the mRNA by recognizing the same or multiple sites. The presence of multiple miRNA binding sites may result in the cooperative action of multiple RISCs and provide highly efficient inhibition of expression. The target site sequence may comprise a total of 5-100, 10-60, or more nucleotides. The target site sequence may comprise at least 5 nucleotides of the sequence of a target gene binding site.

In some embodiments, the cloning capacity of the recombinant RNA vector may be limited and a desired coding sequence may involve the complete replacement of the virus's 4.8 kilobase genome. Large genes may, therefore, not be suitable for use in a standard recombinant AAV vector, in some cases. The skilled artisan will appreciate that options are available in the art for overcoming a limited coding capacity. For example, the AAV ITRs of two genomes can anneal to form head to tail concatamers, almost doubling the capacity of the vector. Insertion of splice sites allows for the removal of the ITRs from the transcript. Other options for overcoming a limited cloning capacity will be apparent to the skilled artisan.

Recombinant AAV Administration rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected tissue (e.g., liver tissue, lung tissue) and administration subcutaneously, intraopancreatically, intranasally, parenterally, intravenously, intramuscularly, intrathecally, intracerebrally, orally, intraperitoneally, by inhalation or by another route. Routes of administration may be combined, if desired.

Delivery of certain rAAVs to a subject may be, for example, by administration into the bloodstream of the subject. Administration into the bloodstream may be by injection into a vein, an artery, or any other vascular conduit. Moreover, in certain instances, it may be desirable to deliver the rAAVs to brain tissue, meninges, neuronal cells, glial cells, astrocytes, oligodendrocytes, cercobrospinal fluid (CSF), interstitial spaces and the like. In some embodiments, recombinant AAVs may be delivered directly to the spinal cord or brain (e.g., prefrontal cortex) by injection into the ventricular region, as well as to the striatum (e.g., the caudate nucleus or putamen of the striatum), and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

In certain circumstances it will be desirable to deliver the rAAV-based therapeutic constructs in suitably formulated pharmaceutical compositions disclosed herein either intrathecally, intracerebrally, intravenously, subcutaneously, intraopancreatically, intranasally, parenterally, intravenously, intramuscularly, orally, intraperitoneally, or by inhalation.

It can be appreciated by one skilled in the art that desirable administration of rAAV-based therapeutic constructs can also include ex vivo administration. In some embodiments, ex vivo administration comprises (1) isolation of cells or tissue(s) of interest from a subject, (2) contacting the cells or tissue(s) with rAAVs in sufficient amounts to transfect the cells or tissue to provide sufficient levels of gene transfer and expression without undue adverse effect, and (3) transferring cells or tissue back into the subject. In some embodiments, cells or tissues may be cultured ex vivo for several days before and/or after transfection.

Cells or tissues can be isolated from a subject by any suitable method. For example, cells or tissues may be isolated by surgery, biopsy (e.g., biopsy of skin tissue, lung tissue, liver tissue, adipose tissue), or collection of biological fluids such as blood. In some embodiments, cells are isolated from bone marrow. In some embodiments, cells are isolated from adipose tissue. In some embodiments, cells are isolated from a lipoaspirate. Appropriate methods for isolating cells from adipose tissue for ex vivo transfection are known in the art. See, e.g., Kuroda, M., et al., (2011), Journal of Diabetes Investigation, 2:333-340; Kouki Morizono, et al. Human Gene Therapy. January 2003, 14 (1): 59-66; and Patricia A. Zuk, Viral Transduction of Adipose-Derived Stem Cells, Methods in Molecular Biology, 1, Volume 702, Adipose-Derived Stem Cells, Part 4, Pages 345-357.

In some embodiments, the isolated cells comprise stem cells, pluripotent stem cells, neuroprogenitor cells, lipoaspirate derived stem cells, liver cells (e.g., hepatocytes), hematopoietic stem cells, mesenchymal stem cells, stromal cells, hematopoietic cells, blood cells, fibroblasts, endothelial cells, epithelial cells, or other suitable cells. In some embodiments, cells to be transfected are induced pluripotent stem cells prepared from cells isolated from the subject.

In an embodiment, cells or tissue(s) are transduced at a multiplicity of infection (MOI) of at least 10 infectious units (i.u.) of a rAAV per cell (for example, 10, 100, 1,000, 5,000, 10,000, 100,000 or more i.u.) or at a functionally equivalent viral copy number. In one embodiment, cells or tissue(s) are transduced at a MOI of 10 to 10,000 i.u . . . . Routes for transfer of transfected cells or tissue(s) into a subject include, but are not limited to, subcutaneously, intraopancreatically, intranasally, parenterally, intravenously, intravascularly, intramuscularly, intrathecally, intracerebrally, intraperitoneally, or by inhalation. In some embodiments, transfected cells are administered by hepatic portal vein injection. In some embodiments, transfected cells are administered intravascularly. Methods for ex vivo administration of rAAV are well known in the art (see, e.g., Naldini, L. Nature Reviews Genetics (2011) 12, 301-315, Li, H. et al. Molecular Therapy (2010) 18, 1553-1558, and Loiler et al. Gene Therapy (2003) 10, 1551-1558).

Recombinant AAV Compositions

The rAAVs may be delivered to a subject in compositions according to any appropriate methods known in the art. The rAAV, which may be suspended in a physiologically compatible carrier (e.g., in a composition), may be administered to a subject, e.g., a human, mouse, rat, cat, dog, sheep, rabbit, horse, cow, goat, pig, guinea pig, hamster, chicken, turkey, or a non-human primate (e.g., Marmoset, Macaque). The compositions of the invention may comprise a rAAV alone, or in combination with one or more other viruses (e.g., a second rAAV encoding having one or more different transgenes).

In some embodiments, to assess gene silencing in relatively large primates, experiments are performed in African Green Monkeys or other relatively large primates. In some embodiments, rAAV vectors expressing miRNAs (e.g., miR-SOD1) are injected in the CSF of such primates both caudally using an IT injection and rostrally using cisterna *magna* injections.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. Still others will be apparent to the skilled artisan.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The dose of rAAV virions required to achieve a desired effect or "therapeutic effect," e.g., the units of dose in vector genomes/per kilogram of body weight (vg/kg), will vary based on several factors including, but not limited to: the route of rAAV administration, the level of gene or RNA expression required to achieve a therapeutic effect, the specific disease or disorder being treated, and the stability of the gene or RNA product. One of skill in the art can readily determine a rAAV virion dose range to treat a subject having a particular disease or disorder based on the aforementioned factors, as well as other factors that are well known in the art. An effective amount of the rAAV is generally in the range of from about 10 μl to about 100 ml of solution containing from about 109 to 1016 genome copies per subject. Other volumes of solution may be used. The volume used will typically depend, among other things, on the size of the subject, the dose of the rAAV, and the route of administration. For example, for intravenous administration a volume in range of 10 μl to 100 μl, 100 μl to 1 ml, 1 ml to 10 ml, or more may be used. In some cases, a dosage between about $10^{10}$ to $10^{12}$ rAAV genome copies per subject is appropriate. In some embodiments the rAAV is administered at a dose of $10^{10}$, $10^{11}$, $10^{12}$, $10^{13}$, $10^{14}$, or 1015 genome copies per subject. In some embodiments the rAAV is administered at a dose of $10^{10}$, $10^{11}$, $10^{12}$, $10^{13}$, or $10^{14}$ genome copies per kg.

In some embodiments, rAAV compositions are formulated to reduce aggregation of AAV particles in the composition, particularly where high rAAV concentrations are present (e.g., ~$10^{13}$ GC/ml or more). Methods for reducing aggregation of rAAVs are well known in the art and, include, for example, addition of surfactants, pH adjustment, salt concentration adjustment, etc. (Scc, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active ingredient or more, although the percentage of the active ingredient(s) may, of course, be varied and may conveniently be between about 1 or 2% and about 70% or 80% or more of the weight or volume of the total formulation. Naturally, the amount of active ingredient in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present invention into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500. ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (e.g., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Kits and Related Compositions

The recombinant nucleic acids, compositions, rAAV vectors, rAAVs, etc. described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to a subject, such as a syringe, topical application devices, or IV needle tubing and bag.

Exemplary embodiments of the invention are described in more detail by the following examples. These embodiments are exemplary of the invention, which one skilled in the art will recognize is not limited to the exemplary embodiments.

EXAMPLES

Example 1: Assessment and Targeting of C9orf72 Expression

Recombinant adeno-associated viral vectors have been developed that deliver miRNAs targeting C9orf72.

Assessment of C9orf72 expression in cell lines and normal human brain:

Two types of cell lines were used that express either WT or mutant C9orf72. A set of 83 lymphoblastoid cells lines were obtained from patients in 78 familial ALS (FALS) pedigrees that are C9orf72 $G_4C_2$ expansion positive. In addition, continuous HEK and SH-SY5Y cell lines were generated that have:

2.0 kb of the C9orf72 promoter upstream of exon 1a, exons 1a and 1b with the intervening intron containing the $G_4C_2$ repeat, and.

2.1 kb of the following intron and exon 2, whose start codon drives luciferase.

Four sub-lines were produced from these cell lines that have $G_4C_2$ expansions of 50, 90, 160 and 200 repeats. Fibroblast cultures were also obtained from C9orf72 $G_4C_2$ expansion cases.

To probe for the principle transcripts of C9orf72 a series of probes and primers were produced that detect either the pre-mRNA or the spliced mRNA. As depicted in FIG. 1 (top), TaqMan probes were developed for the different pre-mRNA isoforms. One probe, $V_{all}$ detects all pre-mRNA transcripts, while two others ($V_1$ or $V_3$) detect the pre-mRNA isoforms $V_1$ or $V_3$. As shown in FIG. 1 (bottom), primer pairs were generated that detect three distinct spliced mRNA isoforms. $V_1$ detects isoform B, while primer pairs $V_2$ and $V_3$ detect two variants of isoforms A.

Figure 2:
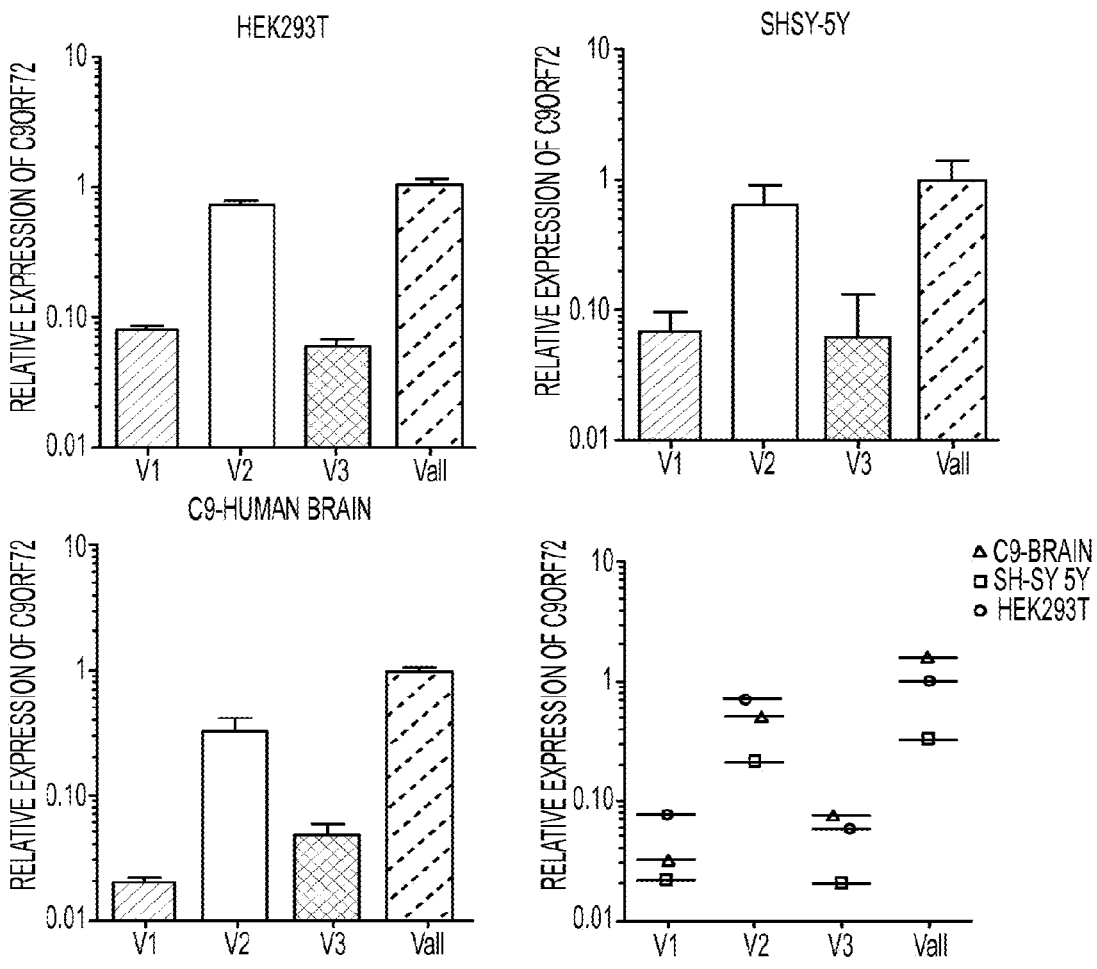
FIG. 2 shows qRT-PCR data relating to detection of C9orf72 variants. TaqMan probe assays designed to detect each individual variant (V1, and V3) or all variants ($V_{all}$) mRNA were tested on various cell lines as well as human brain tissue. The results are means±SD from 3 biological replicates.

As shown in FIG. 2, the TaqMan primers do detect the three major pre-mRNA transcripts from HEK293 and SH-SY5Y cells and from human brain. The transcript levels for $V_1$ and $V_3$ are considerably smaller than $V_{all}$, indicating that, as shown, the predominant transcript in brain and in these cells is $V_2$.

Figure 3:
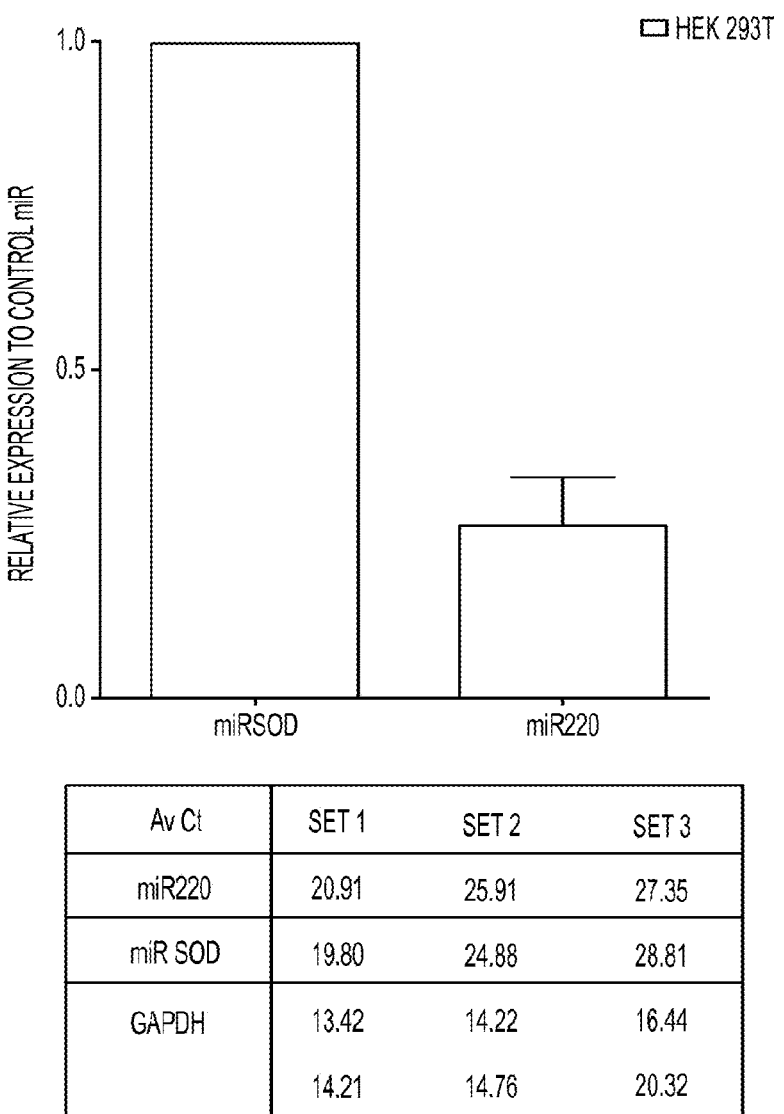
FIG. 3 shows in vitro data relating to miRNA-mediated knockdown of human C9orf72. Relative levels of C9orf72 mRNA after knockdown of C9orf72 with artificial C9miR-220. This miRNA is located in exon 3 and targets all variants. These are results from 3 biological replicates of mir220 (CBA promoter-GFP) transient transfections in HEK293T cells. The control is a miR against SOD1.

MicroRNA Mediated Silencing of Expression of Pre-mRNA and Spliced mRNA in Cells:

The ability of a microRNA targeting the C9orf72 gene to silence its RNA transcripts was assessed. An artificial microRNA, designated C9-miR220 that targets bases 220-241 of the ORF in exon 3 of C9orf72 was developed. Because this miRNA binds in exon 3, it is expected to target all of the mRNA variants. FIG. 3 shows in vitro miRNA-mediated knockdown of human C9orf72. These are results from 3 biological replicates of mir220 (CBA promoter-GFP) transient transfections in HEK293T cells. The control is a miR against SOD1.

Figure 4:
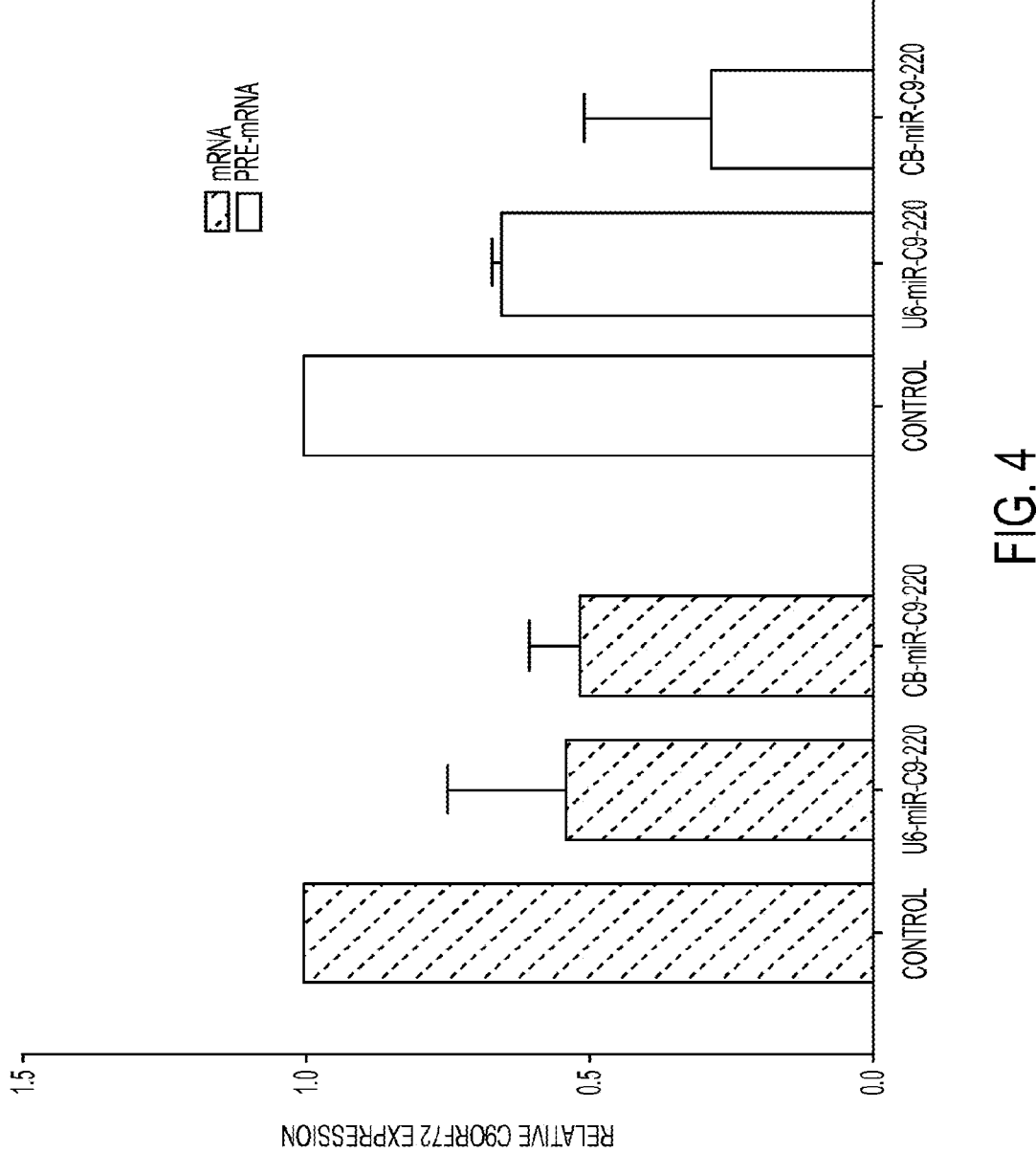
FIG. 4. shows in vitro data relating to knockdown of C9orf72 mRNA and pre-mRNA. C9-miR220 is an artificial miRNA designed to target bases 220-241 of the ORF of C9orf72. This miRNA binds in exon 3 thus targeting all mRNA variants. The miRNA was cloned into either a plasmid using a U6 or Chicken Beta-Actin promoter and transfected into Hek-293 cells. RNA was extracted 72 hours after transfection and DNAse treated prior to RT. Quantitative RT-PCR was done using custom TaqMan probes that either detect spliced (e.g., $V_{all}$ mRNA) or unspliced (e.g.,. $V_{all}$ pre-mRNA) variants. The results are means±SD from 3 biological replicates.

The miRNA was cloned into two different plasmids, using either a U6 or the Chicken Beta-Actin (CBA) promoter. These plasmids were then transfected into Hek-293 cells. After 72 hours, transcripts were assayed using quantitative RT-PCR with the custom TaqMan probes that detect the pre-mRNA transcript or with the primers that detect the spliced mRNA variants. As shown in FIGS. 3 and 4, whether driven by the U6 or the CBA promoter, both forms of the $C_9$-miR220 microRNA reduced levels of spliced mRNA by about 50%. The level of the pre-mRNA transcript was reduced to ~65% (e.g.~ 35% reduction) by the CBA-C9miR220 microRNA, while the U6-C9miR220 suppressed levels of the pre-mRNA to ~ 25% (e.g. ~ 75% reduction). (See FIG. 4) These results demonstrate silencing both the pre-mRNA and mRNA of the C9orf72 gene using an artificial microRNA.

Generation of Mouse Model with BAC Transgenic $G_4C_2$ Expansion:

To generate a mouse model of C9orf72-mediated ALS, a bacterial artificial chromosome (BAC) was isolated from cells of patients having ALS with $G_4C_2$ expansions with ~ 580 repeats and 45 repeats. The BAC having ~ 580 repeats spans exons 1-6 of C9orf72 (Hg18 chr0:27,561,112-27,714,301), while the BAC having 45 repeats spans the full coding sequence. Circularized DNA from these BACs was used to generate transgenic mice. 49 pups were obtained from the 580 repeat BACs, of which 3 were positive for the $G_4C_2$ expansion by PCR assay. One of these three showed germline transmission and produced progeny that have bred well; a colony of these mice with sustained transmission of transgene was established. The original founder aged to ~ 14 months old without an overt motor neuron phenotype. However, brains of $C_9$ BAC transgenic mice at 4 and 6 months of age and presented with salient features. First, as shown in FIG.

5 (lane E), a Southern blot of genomic DNA isolated from the BAC $C_9$ transgenic mouse reveals a dense, heterogeneous band running roughly from 4.5 to ~6.0 kb; this compares well with results using lymphoblastoid (A) and brain (B) DNA from an individual with a $G_4C_2$ expansion. No such band is evident in DNA from brain of an individual without an expansion (lane c) or a non-transgenic mouse (D). A second observation was that probing of sections of the hippocampus from both the 4 and the 6 month 580 repeat BAC $C_9$ transgenic mouse with a $G_4C_2$-CyA probe (to detect the sense-strand RNA) revealed an abundance of intranuclear RNA foci also present throughout the rest of the brain and the spinal cord. (See FIG. 5, right panel). These were detected by a "blinded" observer. The hippocampus control/WT mouse did not show these foci. These results indicate: (1) stable transmission of a BAC C9orf72 transgene with a $G_4C_2$ expansion; and (2) that the mice recapitulate the intranuclear deposits of sense-strand RNA found in human C9orf72 mediated ALS. It has been determined that these foci are not detected after treatment with RNAse. Because these BAC transgenic $C_9$ mice have nuclear RNA foci, silencing of transcript expression from C9orf72 even in the absence of motor neuron disease can be evaluated by assaying for the presence of foci.

Figure 7A:
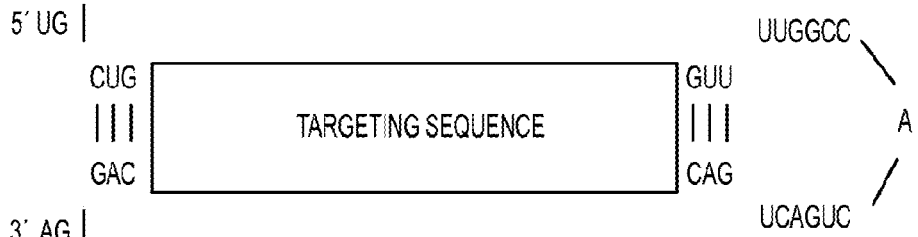
FIGS. 7A-7B illustrate rAAV Vector design for miRNA-mediated silencing of C9orf72.
Figure 7B:
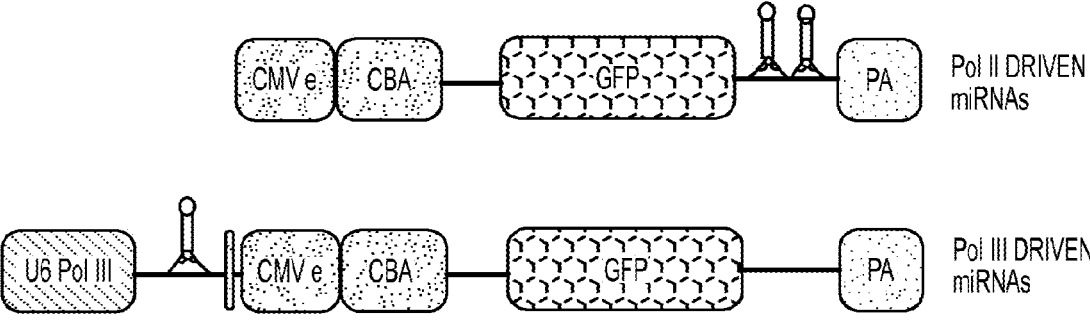

MicroRNA Design:

The miRNA AAV platform is based on miR-155. A stem-loop with a targeting sequence is cloned into the context of the miR-155 flanking regions for efficient recognition and processing by Drosha/DGCR8 complex (FIG. 7). The miRNA design yields a mature 21mer miRNA guide sequence that has either an adenine or uracil at the 5' end. The choice of U or A at the 5'end is driven by the fact that the Mid domain of Ago2 interacts with the 5' end of the mature miRNA and has a 20-fold higher affinity for these two bases over cytosine, and guanine. This design also favors thermodynamic incorporation of the guide strand into the RISC complex. MiRNAs are designed to target areas of low secondary and tertiary complexity target mRNA. This is done with RNA folding algorithms with the goal of increasing the likelihood of miRNA: mRNA cognate binding at the target site. As shown in FIG. 7B the miRNAs are then cloned into a pro-viral plasmid with ITRs expressing GFP and the miRNA of interest either from a polymerase II or polymerase III promoter. 8 miRNA were cloned into these plasmids that target either variants 1 and 3 selectively or all variants (see Table 1).

TABLE 1

| miRNAs Cloned to Target C9orf72 | | | | |
|---|---|---|---|---|
| Name | Targeting miRNA Sequence | SEQ ID NO: | Target Variants | Target Exon |
| miR-C9-123 | 5'-TTTGGAGCCCAAATGTGCCTT-3' | 1 | V1-V2-V3 | 3 |
| miR-C9-220 | 5'-TATAGCACCACTCTCTGCATT-3' | 2 | V1-V2-V3 | 3 |
| miR-C9-220-3'mm | 5'-TATAGCACCACTCTCTGCTAA-3' | 3 | V1-V2-V3 | 3 |
| miR-C9-228 | 5'-TTTACATCTATAGCACCACTC-3' | 4 | V1-V2-V3 | 3 |
| miR-C9-496 | 5'-AATACTCTGACCCTGATCTTC-3' | 5 | V1-V2-V3 | 3 |
| miR-C9-21 | 5'-TGACGCACCTCTCTTTCCTAG-3' | 6 | V1-V3 | 1a-1b |
| miR-C9-48 | 5'-TTTACGTGGGCGGAACTTGTC-3' | 7 | V1-V3 | 1a-1b |

TABLE 1-continued

| | miRNAs Cloned to Target C9orf72 | | | |
|---|---|---|---|---|
| Name | Targeting miRNA Sequence | SEQ ID NO: | Target Variants | Target Exon |
| miR-C9-65 | 5'-TAGATATCAAGCGTCATCTTT-3' | 8 | V1 | 1a-3 |

As shown in Table 1 potential miRNAs have been identified and cloned for the region spanning the hexanucleotide repeat. Pre-mRNA isoforms $V_1$ and $V_3$, were targeted because these encompass the $G_4C_2$ hexanucleotide repeat; as in Table 1, mir-$C_9$-21 and –48 are expected to target $V_1$ and $V_3$.

In addition, miRNAs were used that target all variants. MiR-$C_9$-220 is effective for knock down in vitro of both the mRNA and pre-mRNA species. In certain cases, an miRNA with 40-50% knockdown efficiency in vitro translates to knockdown of more than 80% in vivo due to the increased efficiency of transduction and genome copies achieved with a viral vector. This miRNA function in the nucleus as determined by pre-mRNA knockdown. Nuclear targeting can be improved by modifying the last 3 bases of 3' end of the miRNA to be detargeted from the cognate mRNA. When miRNAs are not 100% complementary to their message and are detargeted at the 3' they form significantly more stable complexes with Ago2. This would increase the residence time of the miRNA in the Ago2 complex and thereby increase the possibility of nuclear translocation. As show in Table 1 we have cloned an miRNA that has a 3' mismatch (miR-$C_9$-220-3'mm) which is useful for assessing this activity.

In vitro Knockdown of C9orf72:

HEK-293T cells and SHSY-5Y cells were transiently transfected with Jet Prime reagent according to the manufacturer's protocol. Transfection of patient fibroblasts uses the protocol for primary fibroblasts on the Nucleofactor electroporator (Lonza AG). Cells are collected 48 hours post transfection, and RNA isolation is performed using Trizol reagent. RNA is then DNAse treated (Turbo DNA-free kit, Applied Biosystems) and reverse-transcribed (High Capacity RNA-to-cDNA kit, Applied Biosystems). For pre-mRNA detection transcript levels are quantified by RT-qPCR (Fast SYBR Green mastermix and primer sets mentioned in the Tables 2 and 3 below, Applied biosystems). For mRNA detection, transcripts are quantified by RT-qPCR (TaqMan mastermix and TaqMan assays in table below, Applied Biosystems). Expression data is analyzed by the 2.4.1Ct.

Primer Design for Pre-mRNA Detection of C9Orf72:

Two primer sets were designed for the detection of pre-mRNA. The first primer set ($V_{all}$) detects all variants, because the primers are located between exon 2 and the adjacent intron. The second set of pre-mRNA primers ($V_1$, $V_3$) detects variants 1 and 3; the primers are located between exon 1 and the adjacent intron (see FIG. 1). Primer sequences are shown in the table below:

TABLE 2

| | C9orf72 pre-mRNA RT-qPCR Assays | |
|---|---|---|
| Name | Primer | SEQ ID NO: |
| $V_{all}$-pre-mRNA-FP | 5'-ACGTAACCTACGGTGTCCC-3' | 9 |

TABLE 2-continued

| | C9orf72 pre-mRNA RT-qPCR Assays | |
|---|---|---|
| Name | Primer | SEQ ID NO: |
| $V_1$ and $V_3$-pre-mRNA-FP | 5'-TGCGGTTGCGGTGCCT-3' | 10 |
| GAPDH-FP | 5'-CTCATGACCACAGTCCATGC-3' | 11 |
| $V_{all}$-pre-mRNA-RP | 5'-CTACAGGCTGCGGTTGTTTC-3' | 12 |
| $V_1$ and $V_3$-pre-mRNA-RP | 5'-CCACCAGTCGCTAGAGGCGA-3' | 13 |
| GAPDH-RP | 5'-ATGACCTTGCCCACAGCCTT-3' | 14 |

Primer-Probe Design for mRNA Detection of C9Orf72:

For the detection of spliced mRNA, primer-probe sets were used. Each set spans exon junctions to discriminate from genomic DNA without having to perform a DNase digestion. $V_1$ detects only variant 1; the primer and probe set span exons 1a and 3. $V_2$ spans the junction between exon 2 and exon 3. $V_3$, which detects variant 3, spans the junction of exon 1b and exon 3. Finally, $V_{all}$ detects all variants; this primer probe set spans the splice junction between exons 3 and 4 (see FIG. 1). TaqMan Primer-probe sequences were ordered through Life Technologies as shown in the table below

TABLE 3

| C9orf72 mRNA RT-qPCR Assays | | |
|---|---|---|
| Name | Catalog# | Sequences |
| $V_1$ | 4331182 | Hs00331877_m1 |
| $V_2$ | 4400294 | Custom |
| $V_3$ | 4400294 | Custom |
| $V_{all}$ | 4331182 | Hs00376619_m1 |
| GAPDH | 4331182 | Hs02758991_g1 |

Fluorescence In Situ Hybridization (FISH) of $G_4C_2$ Nuclear Foci:

Detection of $G_4C_2$ in tissue and patient fibroblasts is achieved by fixing with 4% PFA for 10-20 min on ice, washed 3× with PBS and incubated in 70% Ethanol overnight at 4° C. 40% formamide+2×SSC are added for 20 min at room temperature. The hybridization buffer (250 µl) is prepared with a Cy3 probe specific for the hexanucleotide expansion ($G_4C_2$), incubated for 2 hours at 37° C., and then washed with 40% formamide+1×SSC for 30 min at 37° C.; followed by 2 washes with 1×SSC, RT for 15 min. Slides are then mounted and cover slipped with DAPI-containing mounting media (see FIG. 5, right panel).

C9Orf72 Quantitative Real-Time PCR:

RNA was extracted from cell using Trizol and \reverse-transcribed (High Capacity RNA-to-cDNA kit, Applied Biosystems). Following standard protocols, C9orf72 transcripts levels were quantified by RT-qPCR using Fast Taqman mastermix and the Taqman assays in Tables 2 and 3 (Applied Biosystems). Relative Quantification was determined using the 2-43Ct method.

Quantification of $G_4C_2$ Nuclear Foci:

The frequency of occurrence of RNA foci in patient fibroblasts are assessed by analyzing random microscopically photographed fields at 60×. Automated counting of RNA foci is carried out using the FishJ algorithm macro in the ImageJ software.

Statistical Analysis:

Relative expression of C9orf72 transcripts for both mRNA and pre-mRNA after transfection with the various plasmids are analyzed using the 2-44Ct equation. Values for at least three biological replicates comparing controls (GFP-Scramble-miR) to experimental (GFP-$C_9$-miR) were analyzed with a two sample t-test for statistical significance. A secondary endpoint in the experiments involving patient fibroblast was the average presence of $G_4C_2$ nuclear foci. Foci data were obtained from FishJ digital image analysis for at least 3 biological replicates comparing controls versus experimental transfections, and again were compared using a two sample student t-test.

Example 2: In vivo efficacy of intrathecally-delivered recombinant Adeno-Associated Virus type Rh10 (rAAV.Rh10-C9miR) in silencing expression of pre-mRNA and mature mRNA from the C9orf72 gene in mice Intrathecally delivered rAAV.Rh10 expressing anti-$C_9$ miRs reduce central nervous system levels of C9orf72 RNA transcripts in both wild-type mice and BAC-derived C9orf72$^{mutant}$ transgenic mice. The effectiveness of rAAV.Rh10-C9miR in suppressing levels of C9orf72 and the associated $G_4C_2$ transcripts are evaluated in transgenic mice.

Figure 8:
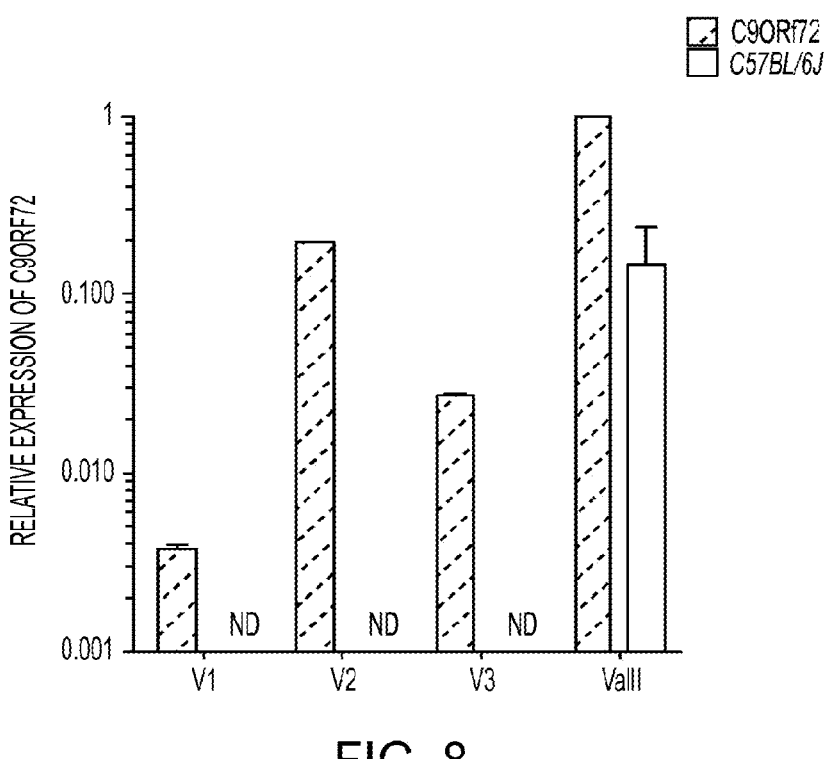
FIG. 8 illustrates qRT-PCR data relating to different C9orf72 variants in mice.

Primers $V_1$, $V_2$. $V_3$, and $V_{all}$ are used to assess C9orf72 transcripts. As shown in FIG. 8, assays using $V_1$, $V_2$ and $V_3$ primers detect transcripts of the transgenic mouse, whereas $V_{all}$ primers detect both mouse and human C9orf72.

Figure 5:
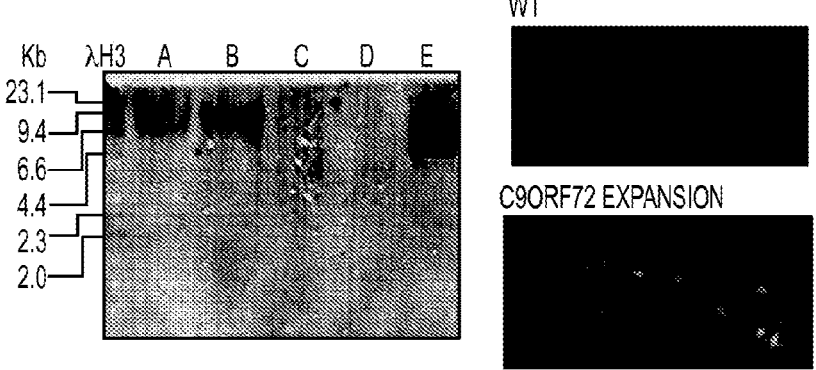
FIG. 5 shows a Southern analysis of DNA (Left panel). Lanes: (A) ALS lymphoblast DNA RB8088. C9orf72 expanded, ~ 8 kb (900repeats); (B) ALS cortex DNA RB9783. C9orf72 expanded, ~9 kb (1000 repeats); (C) ALS cortex DNA RB2952. C9orf72, wild type, no expansion band; (D) Mouse spleen DNA Non transgenic; (E): Mouse spleen DNA CH523-111K12_523. C9orf72 expansion BAC, ~4.5 kb (350 repeats). For each specimen, 25 μg of DNA was digested by Xbal and separated on 0.8% agar gel 2.5 hours at 80-V. Hybridization was at 55oc with an RNA oligo probe ($G_4C2$) 4-DIG and visualized with CDP-Star. Right: Hybridization of hippocampus of WT and C9orf72 mice with $G_4C_2$-CyA probe for sense strand of RNA.
Figure 9:
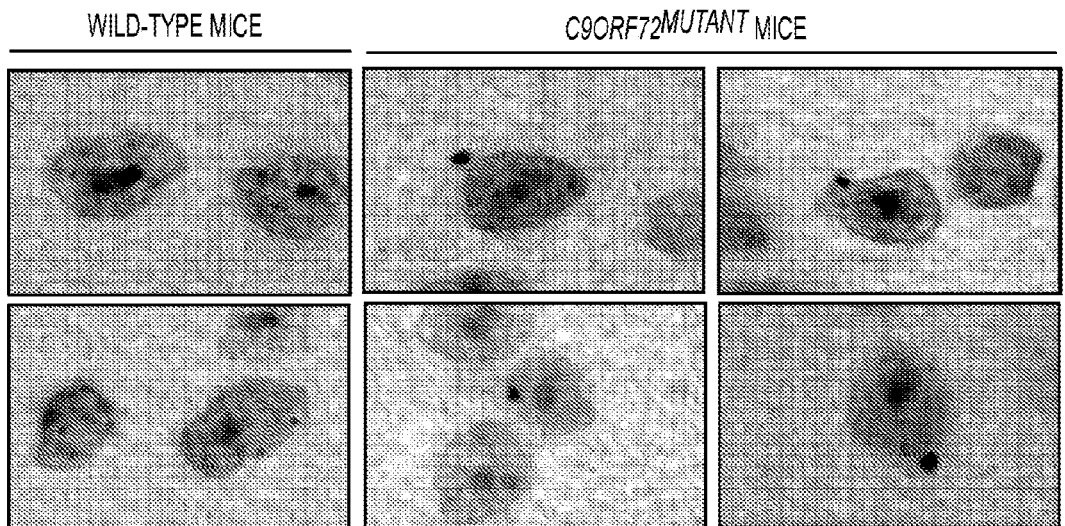
FIG. 9 illustrates that C9orf72 mutant transgenic mice develop poly(GP) inclusions in the frontal cortex.

The effective of rAAV.Rh10-C9miR on reducing levels of the pre-mRNA and spliced mRNA transcripts of C9orf72 is evaluated using both wildtype and our C9orf72"ulant transgenic mice. The extent to which rAAV.Rh10-C9miR reduces numbers of RNAi foci in the transgenic mice is evaluated. The extent to which rAAV.Rh10-C9miR reduces levels of c9-RAN proteins [poly(G), poly(GA), poly(GR)] is also evaluated. rAAV.Rh10-C9miRs are administered in wild-type and C9orf72$^{mutant}$ transgenic mice to assess knockdown of the endogenous C9orf72 pre-mRNA and spliced mRNA. C9orf72$^{mutant}$ transgenic mice demonstrate the presence RNA foci as indicated in FIG. 9,CNS tissue from the C9orf72$^{mutant}$ transgenic mice immunostains positively for RAN-translated peptides. Thus, changes in the occurrence of foci and RAN-translated peptides is used to assess effectiveness of rAAV.Rh10-C9miRs administration. Reduction in dipeptide levels, for example, serves as a measure of efficacy of silencing.

rAAV.Rh10-C9miRs in the C9orf72$^{mutant}$ transgenic mice used to assess the extent to which C9-miRs achieve reductions in (1) pre-mRNA and mRNA levels; (2) numbers of RNA foci, and (3) production of c9 RAN proteins [poly(G), poly(GA), poly(GR)]. Fluorescence in situ hybridization (FISH) of $G_4C_2$ nuclear foci is performed on brain and spinal cord tissue of treated and un-treated mice, as shown in FIG. 5.

As outlined in Tables 4 and 5 rAAVs are injected both neonatal and adult mice; for the former intravenous delivery is used; for the latter, the delivery is intrathecal. Neonatal injections allow widespread CNS transduction with a small volume of vector. Intrathecal administration reduces the amount of virus required to transduce the CNS, and it minimizes systemic exposure to the rAAV.

TABLE 4

Wildtype Mouse Studies with AAVRh10-C9-miRs

| Treatment | Injection Age in C57BL/6 | | |
| | P1 (Neonate)/ Dose | P 28 (Neonate)/ Dose | 3 Months/Dose |
| --- | --- | --- | --- |
| rAAV.Rh10-C9miRs | n = 12 (Males), $1.0e^{11}$ vg | n = 12 (Males), $1e^{12}$ vg | n = 12 (Males), $5e^{10}$ vg |
| rAAV.Rh10-Controls | n = 12 (Males), $1.0e^{11}$ vg | n = 12 (Males), $1e^{12}$ vg | n = 12 (Males), $5e^{10}$ vg |
| PBS Injected Controls | n = 12 (Males), $1.0e^{11}$ vg | n = 12 (Males), $1e^{12}$ vg | n = 12 (Males), $5e^{10}$ vg |

TABLE 5

Transgenic Mouse Studies with AAVRh10-C9-miRs

| Treatment | Injection Age in C9orf72$^{mutant}$ Transgenic mice | | |
| | P1 (Neonate) | P 28 (Neonate)/ Dose | 3 Months/Dose |
| --- | --- | --- | --- |
| rAAV.Rh10-C9miRs | n = 12 (Males), $1.0e^{11}$ vg | n = 12 (Males), $1e^{12}$ vg | n = 12 (Males), $5e^{10}$ vg |
| rAAV.Rh10-Controls | n = 12 (Males), $1.0e^{11}$ vg | n = 12 (Males), $1e^{12}$ vg | n = 12 (Males), $5e^{10}$ vg |
| PBS Injected Controls | n = 12 (Males), $1.0e^{11}$ vg | n = 12 (Males), $1e^{12}$ vg | n = 12 (Males), $5e^{10}$ vg |

Neonate Peripheral Injection:

For neonate injections, hypothermia is used to anesthetize animals prior to intravenous administration. Animals are placed on a bed of wet ice for 1-3 minutes, then injected in the facial vein for P1 and caudal vein for p28 and returned to bedding with their littermates. The neonate injection procedure takes approximately 5 minutes.

Lumbar Intrathecal Injection:

Adult mice are anesthetized with isoflurane in an induction chamber at 2.5%. Once asleep, the animals are transferred to a nose cone where continuous isoflurane is administered. Mice are injected with of either a vector encoding a miR against C9orf72 or a scrambled control miR at a dose of $5\times10^{10}$ vector genomes/animal in a 5 µl volume. This dose is equivalent to $2\times10^{12}$ vg/kg (considering a 25 gr. mouse). Intrathecal (IT) administration is performed using a 30-gauge, 0.5 inch sterile disposable needle connected to a 50 µl glass Luer-hub Hamilton syringe. The site of injection is between L5 and L6. Post-procedural pain is managed with Ketoprofen (5 mg/kg, s.c.) at the time of IT injection, and 24 to 48 hours later if the animal appears to be in discomfort.

Figure 10A:
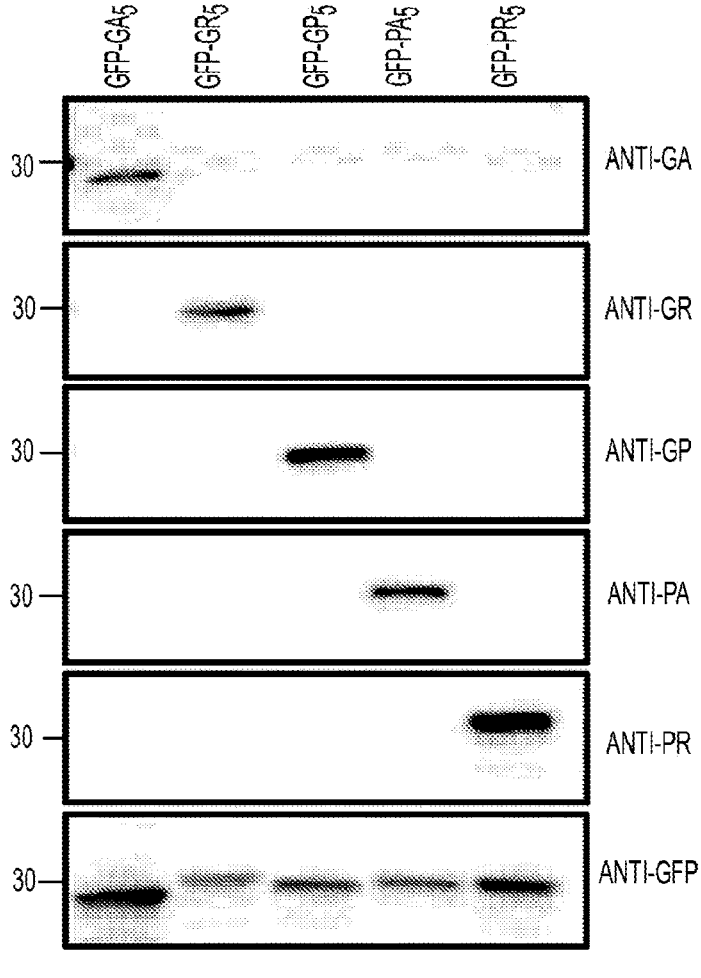
FIGS. 10A-10B show antibodies directed against RAN-translated peptides detect inclusions in C9FTD/ALS brain tissue.
Figure 10B:
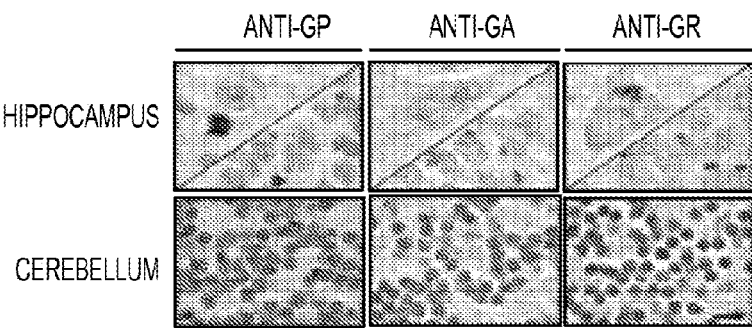

Detection of RAN-Translated Peptides:

Cytoplasmic inclusions immunopositive for a poly(GP) antibody are present in the frontal cortex of C9orf72$^{mutant}$ transgenic mice as shown in FIG. 9. To determine whether C9orf72$^{mutant}$ transgenic mice express other RAN-translated peptides, and to evaluate whether the extent of RAN trans-
lation increases with age, expression of poly(GA), poly(GR)
and poly(GP) peptides are examined at multiple time-points
using rabbit polyclonal antibodies. These antibodies, which
specifically detect their immunogen and show no cross-
reactivity with other peptides RAN-translated from sense or
antisense transcripts of the C9orf72 repeat expansion (FIG.
10A), detect neuronal inclusions throughout the CNS of
c9FTD/ALS patients (FIG. 10B).

At 2, 4, 8, and 12 months of age, brain and spinal cord are
harvested from wild-type and transgenic mice. Each brain is
hemisected across the sagittal midline: one half is fixed in
10% formalin, while the other half is dissected into 6 regions
(cortex, subcortex, hippocampus, midbrain, brainstem and
cerebellum) and frozen. Each spinal cord is cut into 4
transverse sections; sections 1 and 3 are fixed, and sections
2 and 4 are frozen.

For immunohistochemical studies, fixed spinal cord and
hemi-brains are embedded in paraffin and sectioned (sagi-
tally for brain and transversely for spinal cord). Sections are
immunostained with poly(GA), poly(GR) and poly(GP)
antibodies using the DAKO Autostainer (DAKO Auto
Machine Corporation) with DAKO Envision+HRP System.
In addition, to assess the extent to which inclusions of RAN
translated peptides are found only in neurons, as is the case
in human c9FTD/ALS brain, double-immunofluorescence
staining is carried out using antibodies for RAN-translated
peptides and neuronal or astrocytic makers.

To assess expression levels of RAN-translated peptides,
and peptide solubility changes in an age-dependent manner,
frozen brain and spinal cord tissues are subjected to sequen-
tial extractions to collect fractions of soluble and insoluble
proteins. These fractions are examined by Western blot and
quantitative electrochemiluminescent immunoassay using
poly(GA), poly(GR) or poly(GP) antibodies.

Effect of anti-C9orf72 miRNAs on expression of RAN-
translated peptides in C9orf72mutant transgenic mice:

To assess the extent to which silencing of C9orf72 tran-
scripts by rAAV.Rh10-C9mir decreases expression of poly
(GP) peptides and other RAN translated products expressed
in C9orf72$^{mutant}$ transgenic mice, brain and spinal cord of
mice are harvested at various time-points post-transduction.
IHC, Western blot and immunoassay analysis of RAN-
translated peptides are carried-out to the number of inclu-
sions, as well as levels of soluble and/or insoluble RAN-
translated peptides.

TABLE 6

Summary of endpoints and outcome measures for animal studies

| Endpoint/Procedure | Histology |
|---|---|
| GFP | to track cellular distribution of vector |
| Chat/NeuN | as a co-stain with GFP to track Neurons |
| GFAP | as a co-stain with GFP to track Astrocytes |
| Cd11b | as a co-stain with GFP to track Microglia |
| Olig1 | as a co-stain with GFP to track Oligodendricytes |
| $G_4C_2$ FISH | to assess RNA foci in the nucleus (FIG. 5) |
| RAN-Translated proteins | to assess a RAN translation products (FIG. 9) |

| mRNA, miR and Vector Genome Quantification | |
|---|---|
| C9orf72 mRNA | RT-qPCR are as shown in FIG. 2 |
| C9orf72 pre-mRNA | RT-qPCR as shown in FIG. 4 |
| C9-miR Quantification | RT-qPCR using custom assays |
| rAAV Quantification | qPCR for rAAV genomes (biodistribution) |

Digital Image Analysis:

Quantification RAN-Translated Protein Foci:

Analysis of IHC stained slides for RAN-translated pro-
teins is performed using the Aperio positive pixel count
image analysis program. Whole slides are scanned and
digitized using Aperio Software. Analyses are conducted on
the entire brain and spinal cord sections unless staining
artifacts are noted, such as precipitated chromogen. These
areas are excluded from analysis using the pen tool to outline
the region. The analysis procedure is conducted on all
images which are submitted for batch processing using the
Spectrum software. This process subjects all IHC stained
slides to the one standard positive pixel count algorithm. The
default settings used for brown chromogen quantification are
in the three intensity ranges (220-175, 175-100, and 100-0).
Pixels which are stained, but do not fall into the positive-
color specification, are considered negative stained pixels.
These pixels are counted as well, so that the fraction of
positive to total positive and negative pixels is determined.
Positivity (%) data are reported as the number of positive
pixels (medium and strong positives)/total positive and
negative pixel number.

Quantification of $G_4C_2$ Nuclear Foci:

The frequency of the RNA foci are assessed by transect-
sampling across the cerebellum and gray matter of the spinal
cord. Microscopic fields are randomly chosen by a blinded
operator and photographed with an oil immersion 60× lens.
Automated counting of RNA foci in the images is then
carried out using the FishJ algorithm macro in the ImageJ
software.

Statistical Considerations:

Quantification of relative changes in gene expression of
the C9orf72 mRNA and pre-mRNA transcripts after AAV
delivery with the various constructs are analyzed using the
2-3.JCt equation. To determine statistical significant differ-
ences average values are compared for the control groups
(GFP-Scramble-miR) or (PBS controls) to averages from the
experimental group (AAVRh-C9-miR) using a two sample
t-test for statistical significance. Digital image analysis for
RNA nuclear foci and RAN-translated proteins from trans-
genic mouse tissue sections are quantified by FishJ and
Aperio software respectively. Values are obtained for each
animal and averaged according to groups for statistical
analysis (Student t-test). The data for cerebellum and spinal
cord from each group are analyzed individually.

Example 3: miRNA Targeting of C9orf72 in Primates

Assessment of rAAV.Rh10-C9miR and the extent of
silencing of transcripts of C9orf72 in the central nervous
system of non-human primates (NHP) after intrathecal
delivery.

The extent to which intrathecally administered
rAAV.Rh10-C9miR spreads throughout spinal cord, cere-
brum and cerebellum in non-human primates (NHPs) is
assessed. Three rAAV.Rh10 vectors are prepared for the
delivery of expression constructs encoding anti-$C_9$ miRNA.
The vectors are delivered via the intrathecal injection. Both
spread and tropism of AAVRh 10 are assessed, as well as the
silencing efficacy of C9-miRs from two different promoters
over a3 week period. One of the cohorts is injected with
vectors expressing the miRNA is from a polymerase II
promoter (a hybrid chicken beta actin promoter) driving
GFP. Another cohort is administered a bicistronic vector in
which the miRNA is expressed from a U6 polymerase III
promoter which is placed upstream of the hybrid chicken beta actin promoter driving GFP expression (FIG. 7B). A third cohort receives a GFP only control (see Table 7 below). RT-qPCR is performed on RNAs obtained from motor neurons that are laser captured by micro-dissection. The dose of vector used is based on IT rAAV delivery in NHP studies showing robust cortical and spinal cord transduction.

TABLE 7

Short-term C9orf72 Silencing Study in NHPs
Comparing Pol II vs. Pol III Promoters

| rAAV Construct | CB6-GFP | CB6-GFP-C9-miR | U6-C9-miR-GFP |
|---|---|---|---|
| Number of Animals | 3 Marmosets under 4 years of Age | 3 Marmosets under 4 years of Age | 3 Marmosets under 4 years of Age |
| Route of Delivery and Volume | AAVRh10 Intrathecal (300 ul) | AAVRh10 Intrathecal (300 ul) | AAVRh10 Intrathecal (300 ul) |
| Total rAAV Dose | $1 \times 10^{12}$ vector particles (vp) | $1 \times 10^{12}$ vector particles | $1 \times 10^{12}$ vector particles |
| Approx. NHP Weight | 400-500 grams | 400-500 grams | 400-500 grams |
| Approx. Dose/Weight | $2 \times 10^{12}$ vp/ Kilogram | $2 \times 10^{12}$ vp/ Kilogram | $2 \times 10^{12}$ vp/ Kilogram |
| Promoter Driving GFP | Chicken/ Beta Actin | Chicken/ Beta Actin | Chicken/ Beta Actin |
| Promoter Driving miRNA | Polymerase II (same as above) | Polymerase II (same as above) | Polymerase III (U6 promoter) | rAAV.Rh10-C9-miR vectors that do not encode GFP are used to examine long-term safety of viral delivery of rAAV.Rh10 in marmosets (e.g., 4 controls and 4 treated). In-life endpoints include detailed physical examinations, detailed clinical observations, body weight, standard hematologic and chemistry parameters in blood, assessment of serum antibodies to AAVRh10, T cell responses to AAV peptides, and extent of shedding of vector in body fluids and excreta. Post mortem endpoints include gross necropsy observations, organ weights and histopathology, and blood and tissue rAAV.Rh10-C9-miR vector DNA content (Table 9). In addition the extent of miR silencing of C9orf72 is assessed using methods disclosed herein.

TABLE 8

Endpoints for the NHP biodistribution/toxicology study.

| Endpoint Assessment | Timing of Endpoint |
|---|---|
| Clinical assessment | Daily |
| Quantitative Taqman PCR of blood | Day 0, 1, 7, 21, 90 |
| Quantitative Taqman PCR of semen | Day 0, 1, 7, 21, 90 |
| Quantitative Taqman PCR of multiple organs* | Time of sacrifice |
| Necropsy with multiple organ* histopathology | Time of sacrifice |
| Complete Blood Counts (Hematocrit, leukocytes, platelets) | Day 0, 1, 3, 7, 21, 90 |
| Chemistry Panel (electrolytes, BUN, creatinine, AST, ALT, CK) | Day 0, 1, 3, 7, 21, 90 |
| INF-Gamma ELISPOT for AAVRh10 capsid | Day 0, 7, 21, 60, 90 |
| Neutralizing AAV Antibodies | Day 0, 7, 21, 60, 90 |
| Bisulfite sequencing for $T_{reg}$ analysis | Time of sacrifice |

(*the organ panel for histopathology and quantitative PCR includes brain, spinal cord, heart, lungs, liver, kidney, spleen, pancreas, jejunum, gonads, muscle at injection site, and inguinal lymph node)

Laser Capture Microdissection:

12 mm lumbar spinal cord frozen sections are collected onto PEN membrane slides (Zeiss, Munich, Germany) and stained with 1% Cresyl violet (Sigma, St. Louis, MO) in methanol. Sections are air dried and stored at –80° C. After thawing, motor neurons are collected within 30 min from staining using the laser capture microdissector PALM Robo3 Zeiss) using the following settings: Cut energy: 48, LPC energy: 20, Cut focus: 80/81, LPC focus: 1, Position speed: 100, Cut speed: 50. About 500 MNs are collected per animal. Non-neuronal cells from the ventral horn are collected from the same sections after collecting the motor neurons. RNA is then isolated using the RNaqueous Micro Kit (Ambion, Grand Island, NY) according to manufacturer's instructions.

Interferon Gamma Elispot in Response to rAAV.Rh10 Capsid:

To characterize the immune response to rAAV.Rh10 after IT delivery, lymphocyte proliferation to pooled rAAV.Rh10 capsid peptides are assessed using the ELISPOT assay. Blood obtained at the various time points is processed using a standard Ficoll-Paque™ Plus protocol to obtain peripheral blood mononuclear cells. PBMC at a concentration of $2 \times 10^5$ cells per well is added to a plate coated with IFN-gamma capture antibody. Antigen specific stimulation with rAAV.Rh10 is performed for 18-24 hrs after which cells are thoroughly washed. This is followed by addition of the detection antibody and subsequently Avidin-HRP which is developed with the appropriate substrate for a colorimetric reading.

AAV Neutralizing Antibody Assays:

The presence of AAV-Neutralizing antibodies are assessed using appropriate techniques at a vector core laboratory.

Example 4: Assessment and Targeting of SOD1 Expression

Delivery of the rAAV Vector to Transgenic Mice

Figure 11A:
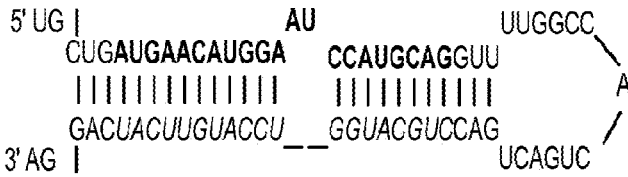
FIGS. 11A-11C show rAAV vector design for miRNA mediated silencing of SOD1. The flanking regions of miR-155 were cloned upstream of the BGH poly A region of a proviral AAV expression cassette composed of the CMV enhancer, chicken Beta actin hybrid promoter with a short SV40 intron.
Figure 11B:
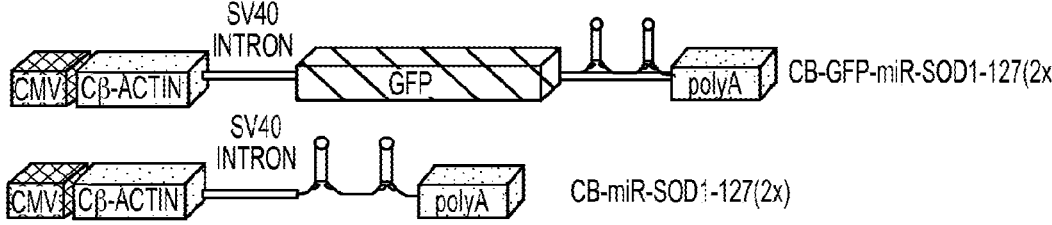
Figure 11C:
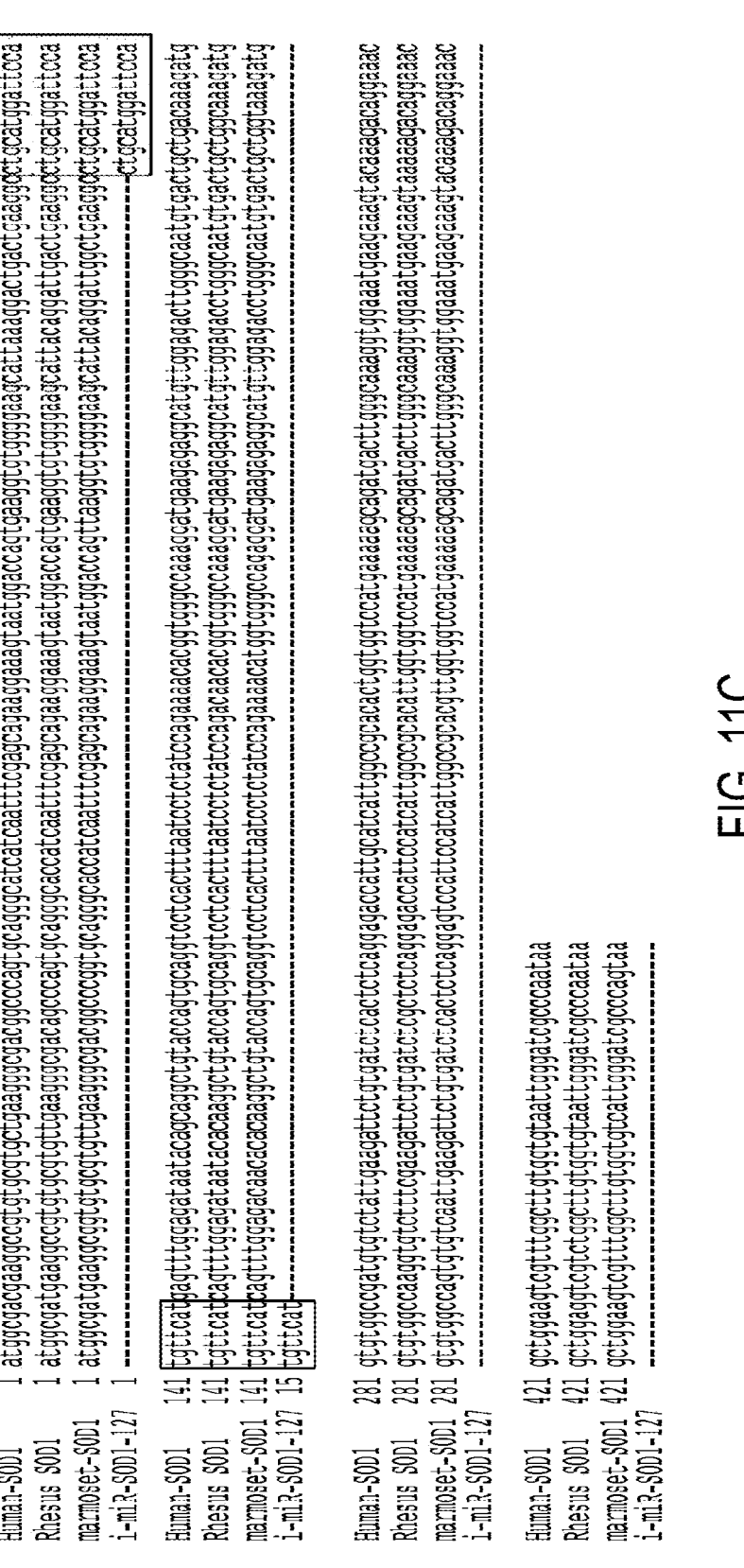
Figure 12B:
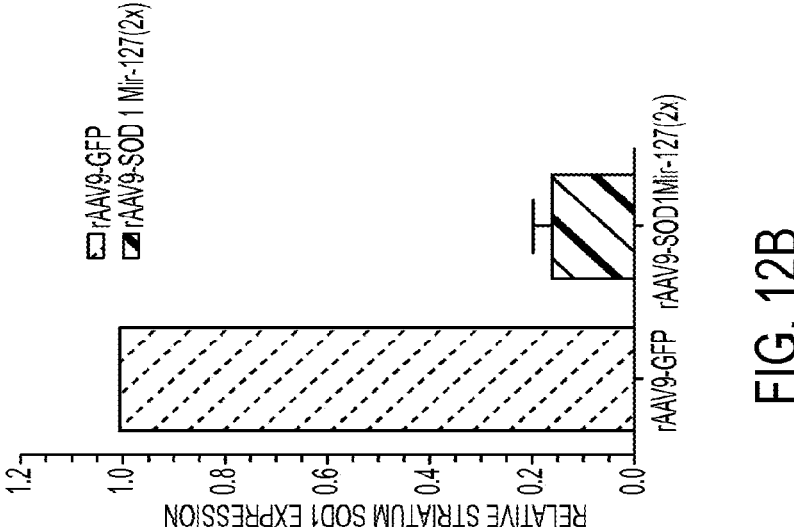
FIGS. 12A-12B show data relating to in vivo rAAV mediated knockdown of human SOD1 in the transgenic mice. Transgenic mice expressing the humans SOD1 G93A mutation were injected with rAAV9 vectors expressing the anti-SOD1 miRs.
Figure 12A:
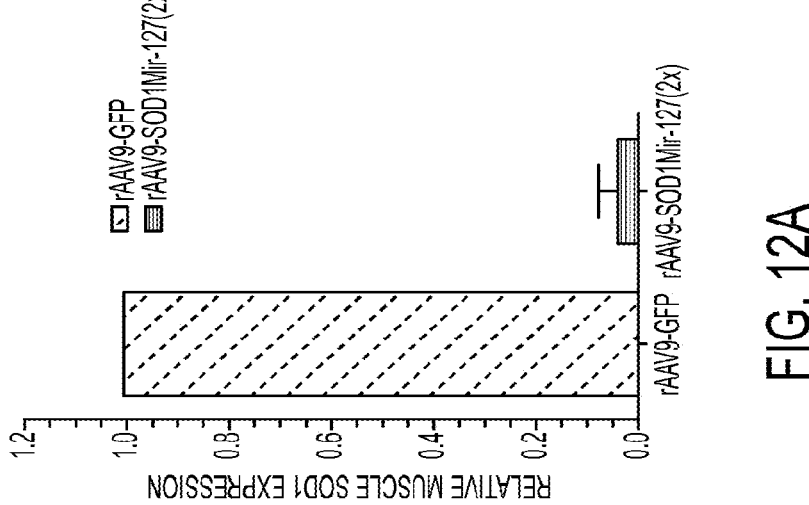
Figure 13:
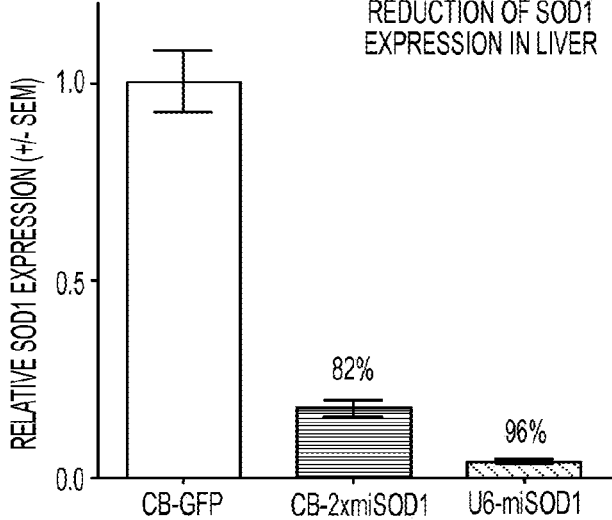
FIG. 13 shows data relating to AAV.Rh10 vector constructs (top), and results indicating reduction of SOD1 expression in marmoset liver (bottom).

A recombinant adeno-associated viral vector has been developed that delivers miRNAs against SOD1 (See FIGS. 11A-C) to cells in vitro or in vivo. Delivery of the rAAV vector to transgenic mice expressing the mutant form of SOD1 resulted in 80-90% knockdown of the target mRNA in transduced tissues (FIG. 12). For example, it was determined anti-SOD1 (miR) silences expression of SOD1 in mouse liver, as shown in FIG. 13.

For these experiments rAAV vectors are used with three types of constructs: (a) chicken beta actin (CB) driving GFP followed by tandem anti-SOD1 miRs (mir127); (b) the U6 promoter driving miR-SOD1 followed by CB-GFP; and as a control CB-GFP alone. FIG. 13 (top panel) shows schematics of these constructs.

It was determined that intrathecally delivered rAAV9 bearing a microRNA to attenuate expression of SOD1 prolongs survival in SOD1G93A transgenic ALS mice. $2.4 \times 10^{10}$ viral genomes/5 µl injected into the lumbar intrathecal space of 60 day old mouse achieved widespread delivery of the microRNA to multiple cell types along the spinal cord. (This dose is ~1/16th the dose used in our IV delivery). In animals that were highly transduced, reduction of SOD1 expression by ~50% was observed as assessed by western immunoblotting. Also observed was a prolongation of survival by ~14 days overall and to more than 160 days in mice with the highest level of SOD1 silencing (as compared to 123 days in ALS mice treated with rAAV9-scrambled microRNA). These results indicate that C9-miR220 can be administered along the length of the spinal cord in rodents and non-human primates using rAAV.Rh10.

Figure 20:
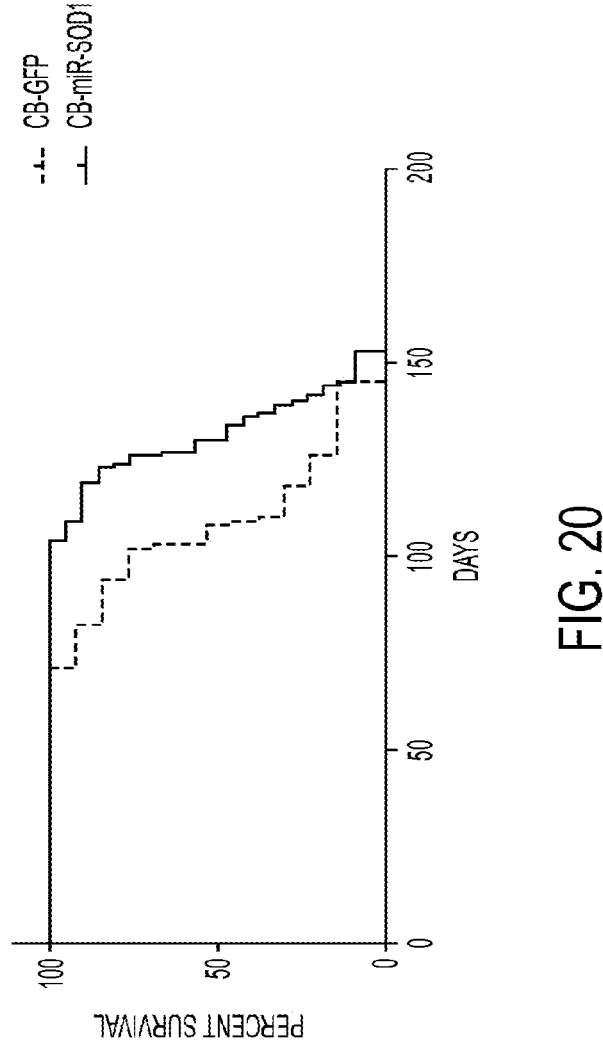
FIG. 20 shows data relating to treatment of G93A SOD1 mice with CB-miR-SOD1 vector. Mice were intravenously injected with $2×10^{12}$ gc of vector (CB-GFP or CB-miR-SOD1-GFP) at day 56-68 of age and subsequently blindly monitored until advanced paralysis required euthanasia. Results show median survival was 108 days for the CB-GFP group and 130 days for the CB-miR-SOD1-GFP group (log-rank test, p=0.018), indicating a significant increase in survival of CB-miR-SOD1-treated mice.

FIG. 20 indicates that treatment of G93A SOD1 mice with CB-miR-SOD1 significantly increases survival compared to control animals. G93A SOD1 mice were injected with $2 \times 10^{12}$ genome copies (gc) of CB-GFP or CB-miR-SOD1-GFP vector at day 56-68 of age and blindly monitored until advanced paralysis required euthanasia. Median survival was 108 days for control animals (CB-GFP, n=19) and 130 days for CB-miR-SOD1-GFP (n=28). Log-rank test results in a p-value of 0.018, suggesting that increased survival is statistically significant. These data further indicate that systemic delivery of mir-SOD1 by intravenous injection results in significant increase in survival of G93A SOD1 mice.

Example 5: miRNA-Targeting of SOD1 in Primates

Intrathecal Delivery of Recombinant AAV (rAAV) Expressing SOD1 miRNA to Brain and Spinal Cord.

Adeno-associated virus (AAV)-mediated delivery of microRNA has been used to silence SOD1 in mammalian tissues, including spinal cord.

Figures 6A, 6B, 6C:
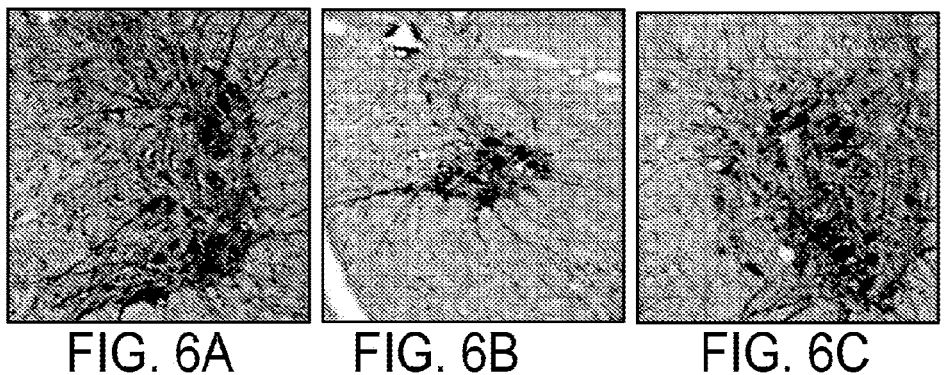
FIGS. 6A-6D provide data indicating robust EGFP transduction and miRNA mediated knockdown in the spinal cord after I.T. injection with rAAV.Rh10. A 4 year-old male marmoset was I.T. injected with either a rAAV.Rh10.CBEGFP or rAAV.Rh10.U6ant—SOD1 miR at a dose of 5×10e12 GCs/kg. The animal was necropsied 2 weeks later and CNS tissues isolated and fixed. Forty micron sections of spinal cord were stained with antibody against EGFP and visualized by DAB. All sections were counterstained with Haematoxylin. Shown are low magnification images (4×objective) of (FIG. 6A) Lumbar spinal cord, (FIG. 6B) thoracic spinal cord, and (FIG. 6C) cervical spinal cord.
Figure 6D:
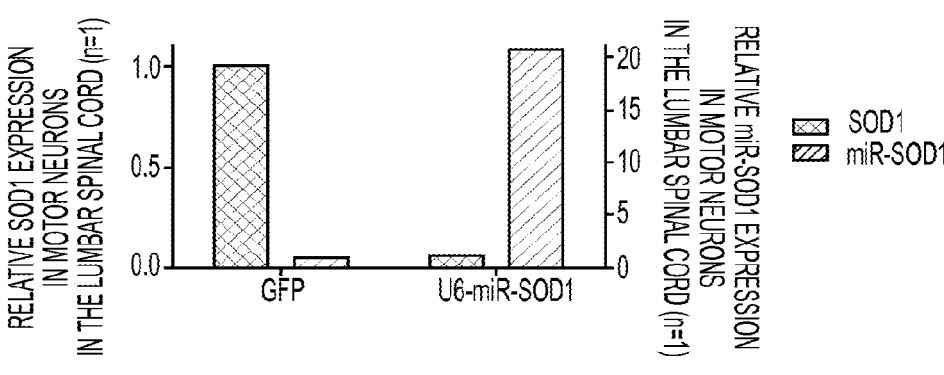

As shown in FIG. 6 intrathecal administration of rAAV.Rh10.EGFP to an adult marmoset resulted in remarkable uptake in gray matter of both the (A) lumbosacral and (B) cervical anterior horns, with prominent labeling of motor neurons (as identified by their sizes and location). Laser-capture lumbo-sacral motor neurons were obtained from this marmoset (treated with rAAV.Rh10.EGFP) and another treated with rAAV.Rh10.U6-miR-SOD1, which expresses a SOD1 silencing miR. As in FIG. 6 (bottom), the control animal showed high levels of SOD1 transcript and minimal (essentially 0 baseline) miR-SOD1. By contrast, in the treated animal the SOD1 transcript was almost undetectable while there was a high level of the miR-SOD1 microRNA.

These constructs were used in studies conducted in nine marmosets, using intrathecal delivery with a newer strain of AAV, designated AAV.Rh10. Details of the design are in FIG. 14. In certain instances, IT injections in these monkeys resulted in tail flick and a dural "pop" as the needle was inserted. In others, needle placement did not result in an observable tail flick. In both instances, there was good delivery of AAV into the CSF. These points are illustrated in FIG. 15. Animals were sacrificed after 3.5-4 weeks. As the table in FIG. 15 notes, three animals were perfused with fixative (PFA) and six with saline. Three of the latter, which had the "good" injections, were used for laser capture of motor neurons and assays of miR and SOD1 levels in the motor neurons.

Figure 16:
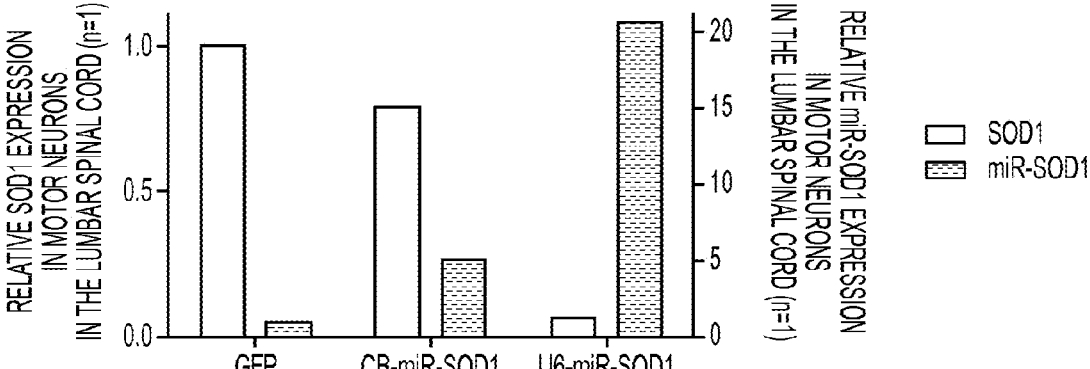
FIG. 16 shows that in 3 male marmosets injected intrathecally (IT) and subjected to laser capture micro-dissection (LCM) (animals 6, 8, 9 in FIG. 15), SOD1 expression was reduced in MNs by AAV.Rh10 CB-2x-miR-SOD1 (light grey) and U6-miR-SOD1 (dark gray). The U6 promoter drove higher levels of the anti-SOD1 miR and more effectively silenced SOD1.
Figure 17A:
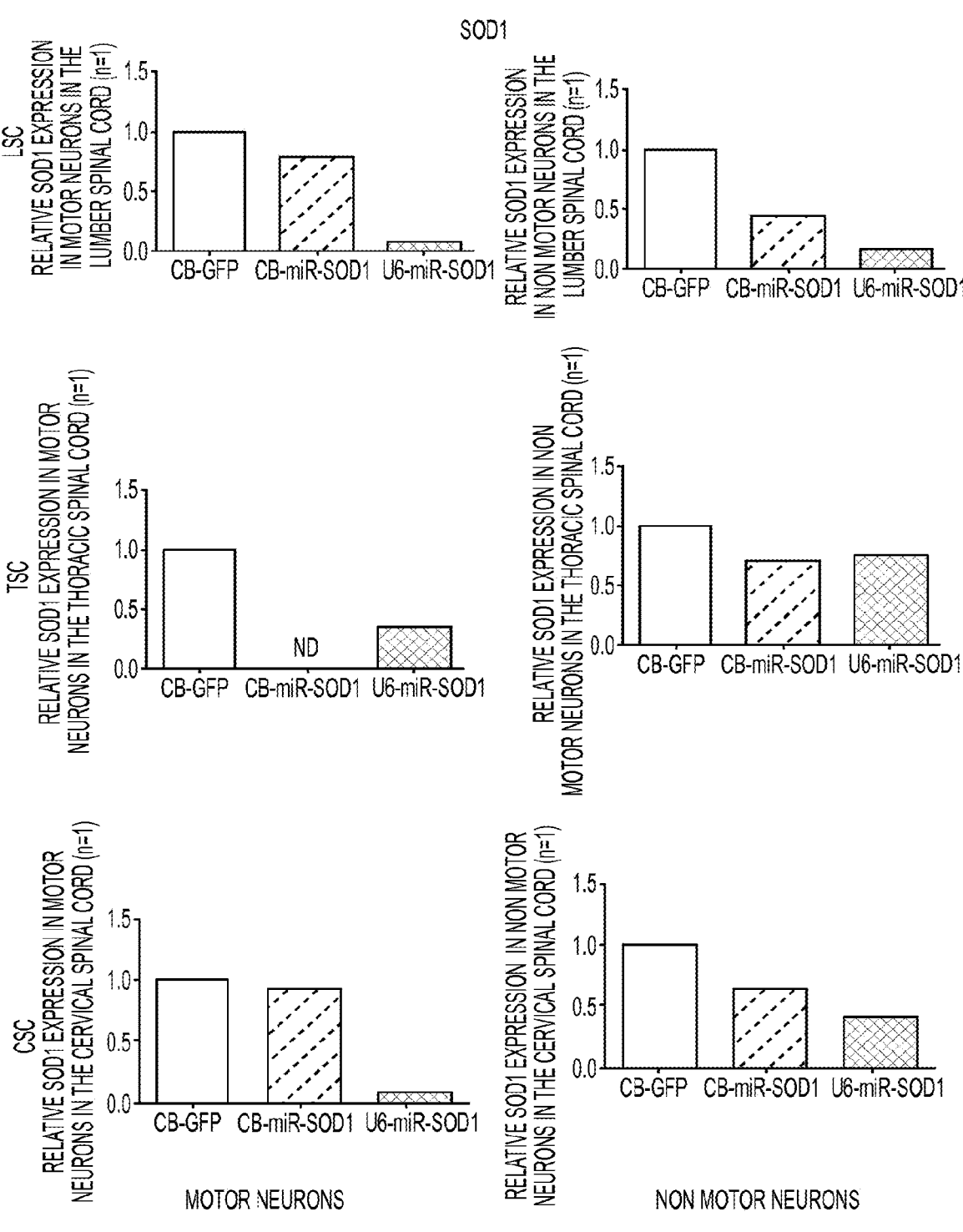
FIGS. 17A-17B show data related to 3 male marmosets (animals 6, 8, 9 in FIG. 15).
Figure 17B:
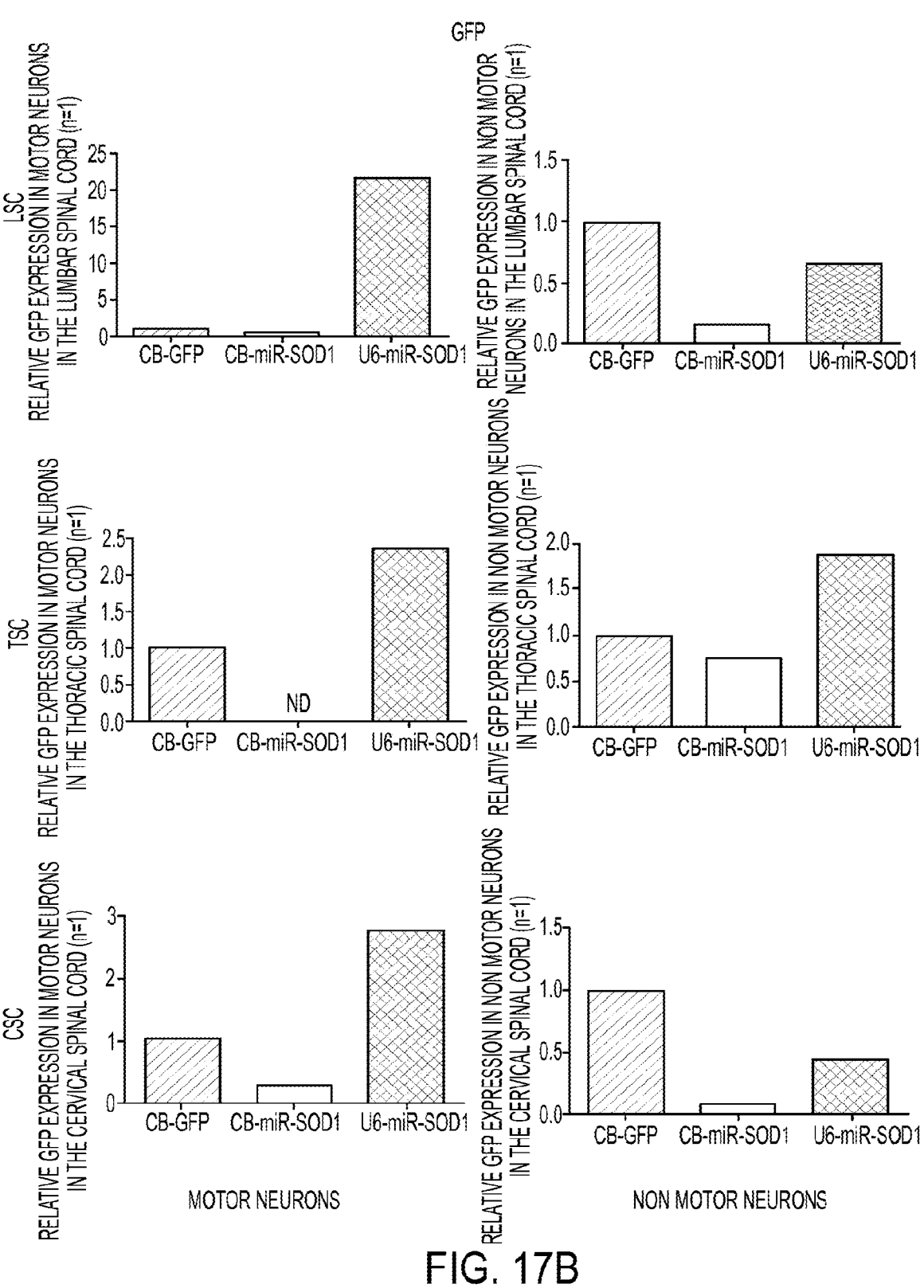
Figure 18:
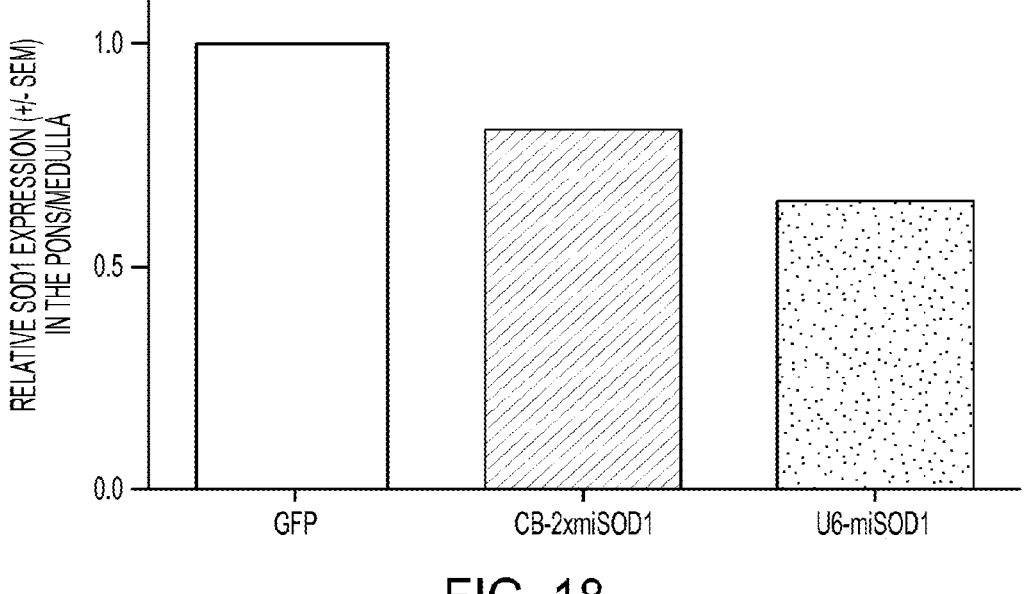
FIG. 18 shows that in the same 3 male marmosets described in FIGS. 17A-17B, the IT injection of AAV.Rh10 CB-2×-miR-SOD1 (light grey) and U6-miR-SOD1 (dark gray) also produced silencing of SOD1 in the lower brainstem. In these studies, qPCR was performed on whole tissue homogenates (not laser captured neurons).

As shown in FIG. 16, after laser capture, MNs transduced with control CB-GFP showed high levels of SOD1 and no miR-SOD1 as gauged by qPCR. Those transduced with U6-miR-SOD1 and CB-miR-SOD1 showed silencing of SOD1 expression. The U6 construct produced more miR; in that animal, there was less SOD1 expression. FIGS. 17A-B extend the results to three regions of the spinal cord (lumbar, thora and examines silencing in both laser-captured MNs and the residual tissue of the cord after MNs were resected (non-MNs). There is evidence of SOD1 silencing in both sets of tissue. FIG. 18 shows silencing in the brainstem as assessed using qPCR with tissue homogenates.

Figure 19:
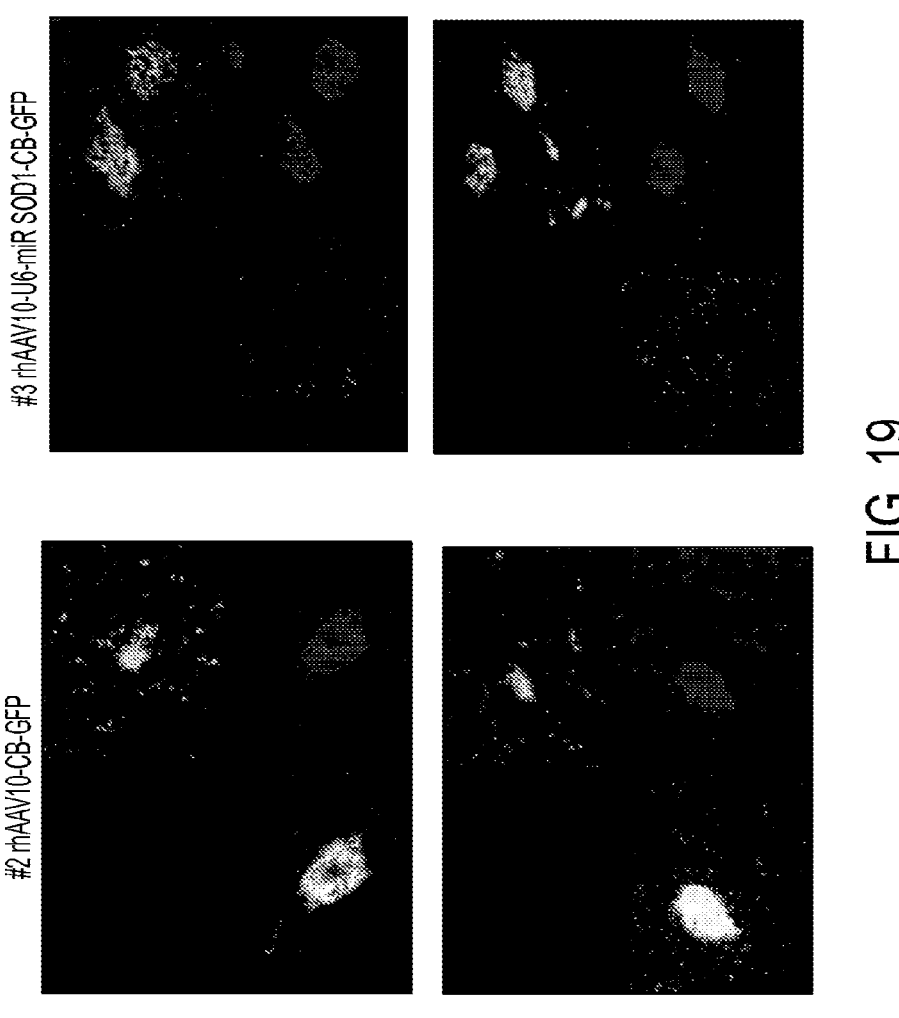
FIG. 19 shows data relating to an assessment of motor neuron (MN) SOD1 expression using RNA hybridization (RNAScope) in cords of two male marmosets (#2 and 3 in FIG. 15). In #2, IT injection with CB-GFP (no miR) achieved some GFP expression in MNs (ChAT pos) which showed prominent SOD1 expression (left). In #3, IT injection with U6-SOD1 miR-CB-GFP produced GFP expression in MN and reduction in SOD1 expression in the same neurons (right).

FIG. 19 uses RNA hybridization ("RNAScope") to demonstrate in single motor neurons that expression of miR-SOD1 (in this case from the U6 construct) correlates with absence of SOD1 expression, while in the MN transduced with CB-GFP alone there is ample SOD1 expression. In summary, these data demonstrate that miR-SOD1 reagents are delivered to spinal cord after IT injection, and achieve substantial silencing of SOD1.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only and the invention is described in detail by the claims that follow.

As used herein, the terms "approximately" or "about" in reference to a number are generally taken to include numbers that fall within a range of 1%, 5%, 10%, 15%, or 20% in either direction (greater than or less than) of the number unless otherwise stated or otherwise evident from the context (except where such number would be less than 0% or exceed 100% of a possible value).

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The entire contents of all references, publications, abstracts, and database entries cited in this specification are incorporated by reference herein.

---

What is claimed is:

1. A method of treating a subject having or suspected of having ALS, the method comprising:
administering to the subject an effective amount of a recombinant adeno-associated virus (rAAV) harboring a nucleic acid that is engineered to express, in a cell of the subject, a miRNA that targets RNA encoded by a SOD1 gene,
wherein the miRNA comprises 21 continuous nucleotides encoded by a sequence set forth in SEQ ID NO: 17: CTGCATGGATTCCATGTTCAT (SOD-miR-127), wherein the rAAV comprises an AAV.Rh10 capsid protein.

2. The method of claim 1, wherein the rAAV targets CNS tissue.

3. The method of claim 1, wherein the rAAV is administered intrathecally, intracerebrally, intraventricularly or intravenously.

4. The method of claim 1, wherein the microRNA further comprises flanking regions of miR-155.

5. The method of claim 1, wherein the nucleic acid further comprises AAV2 inverted terminal repeats (ITRs).

6. The method of claim 1, wherein the nucleic acid further comprises a promoter operably linked with a region(s) encoding the miRNA.

7. The method of claim 6, wherein the promoter is a tissue-specific promoter.

8. The method of claim 7, wherein the promoter is a polymerase II promoter or a polymerase III promoter.

9. A recombinant nucleic acid comprising a sequence set forth in 21 consecutive nucleotides of SEQ ID NO: 17, flanking regions of miR-155, and further comprising an inverted terminal repeat (ITR) of AAV2.

10. The recombinant nucleic acid of claim 9, further comprising a promoter operably linked with a region(s) encoding the miRNA.

11. The recombinant nucleic acid of claim 10, wherein the promoter is a tissue-specific promoter.

12. The recombinant nucleic acid of claim 11, wherein the promoter is a polymerase II promoter.

13. The recombinant nucleic acid of claim 11, wherein the promoter is a polymerase III promoter.

14. A composition comprising the recombinant nucleic acid of claim 9.

15. A recombinant Adeno-Associated Virus (AAV) comprising a recombinant nucleic acid encoding a miRNA comprising 21 consecutive nucleotides encoded by a sequence as set forth in SEQ ID NO: 17, flanking regions of miR-155, and further comprising a capsid protein of AAV.Rh10.

16. The recombinant AAV of claim 15, wherein the recombinant nucleic acid comprises an inverted terminal repeat (ITR) of AAV2.

17. The recombinant AAV (rAAV) of claim 15, wherein the rAAV is formulated for administration intrathecally, intracerebrally, intraventricularly or intravenously.

18. A composition comprising the recombinant AAV of claim 15.

19. The composition of claim 18, further comprising a pharmaceutically acceptable carrier.

20. A kit comprising a container comprising the composition of claim 18.

\* \* \* \* \*

SEQUENCE LISTING

```
Sequence total quantity: 25
SEQ ID NO: 1           moltype = DNA  length = 21
FEATURE                Location/Qualifiers
misc_feature           1..21
                       note = Synthetic nucleic acid
source                 1..21
                       mol_type = other DNA
                       organism = synthetic construct
SEQUENCE: 1
tttggagccc aaatgtgcct t                                    21

SEQ ID NO: 2           moltype = DNA  length = 21
FEATURE                Location/Qualifiers
misc_feature           1..21
                       note = Synthetic nucleic acid
source                 1..21
                       mol_type = other DNA
                       organism = synthetic construct
SEQUENCE: 2
tatagcacca ctctctgcat t                                    21
```

-continued

```
SEQ ID NO: 3           moltype = DNA  length = 21
FEATURE                Location/Qualifiers
misc_feature           1..21
                       note = Synthetic nucleic acid
source                 1..21
                       mol_type = other DNA
                       organism = synthetic construct
SEQUENCE: 3
tatagcacca ctctctgcta a                                       21

SEQ ID NO: 4           moltype = DNA  length = 21
FEATURE                Location/Qualifiers
misc_feature           1..21
                       note = Synthetic nucleic acid
source                 1..21
                       mol_type = other DNA
                       organism = synthetic construct
SEQUENCE: 4
tttacatcta tagcaccact c                                       21

SEQ ID NO: 5           moltype = DNA  length = 21
FEATURE                Location/Qualifiers
misc_feature           1..21
                       note = Synthetic nucleic acid
source                 1..21
                       mol_type = other DNA
                       organism = synthetic construct
SEQUENCE: 5
aatactctga ccctgatctt c                                       21

SEQ ID NO: 6           moltype = DNA  length = 21
FEATURE                Location/Qualifiers
misc_feature           1..21
                       note = Synthetic nucleic acid
source                 1..21
                       mol_type = other DNA
                       organism = synthetic construct
SEQUENCE: 6
tgacgcacct ctctttccta g                                       21

SEQ ID NO: 7           moltype = DNA  length = 21
FEATURE                Location/Qualifiers
misc_feature           1..21
                       note = Synthetic nucleic acid
source                 1..21
                       mol_type = other DNA
                       organism = synthetic construct
SEQUENCE: 7
tttacgtggg cggaacttgt c                                       21

SEQ ID NO: 8           moltype = DNA  length = 21
FEATURE                Location/Qualifiers
misc_feature           1..21
                       note = Synthetic nucleic acid
source                 1..21
                       mol_type = other DNA
                       organism = synthetic construct
SEQUENCE: 8
tagatatcaa gcgtcatctt t                                       21

SEQ ID NO: 9           moltype = DNA  length = 19
FEATURE                Location/Qualifiers
misc_feature           1..19
                       note = Synthetic nucleic acid
source                 1..19
                       mol_type = other DNA
                       organism = synthetic construct
SEQUENCE: 9
acgtaaccta cggtgtccc                                          19

SEQ ID NO: 10          moltype = DNA  length = 16
FEATURE                Location/Qualifiers
misc_feature           1..16
                       note = Synthetic nucleic acid
source                 1..16
                       mol_type = other DNA
                       organism = synthetic construct
SEQUENCE: 10
tgcggttgcg gtgcct                                             16
```

-continued

```
SEQ ID NO: 11           moltype = DNA  length = 20
FEATURE                 Location/Qualifiers
misc_feature            1..20
                        note = Synthetic nucleic acid
source                  1..20
                        mol_type = other DNA
                        organism = synthetic construct
SEQUENCE: 11
ctcatgacca cagtccatgc                                          20

SEQ ID NO: 12           moltype = DNA  length = 20
FEATURE                 Location/Qualifiers
misc_feature            1..20
                        note = Synthetic nucleic acid
source                  1..20
                        mol_type = other DNA
                        organism = synthetic construct
SEQUENCE: 12
ctacaggctg cggttgtttc                                          20

SEQ ID NO: 13           moltype = DNA  length = 20
FEATURE                 Location/Qualifiers
misc_feature            1..20
                        note = Synthetic nucleic acid
source                  1..20
                        mol_type = other DNA
                        organism = synthetic construct
SEQUENCE: 13
ccaccagtcg ctagaggcga                                          20

SEQ ID NO: 14           moltype = DNA  length = 20
FEATURE                 Location/Qualifiers
misc_feature            1..20
                        note = Synthetic nucleic acid
source                  1..20
                        mol_type = other DNA
                        organism = synthetic construct
SEQUENCE: 14
atgaccttgc ccacagcctt                                          20

SEQ ID NO: 15           moltype = DNA  length = 21
FEATURE                 Location/Qualifiers
misc_feature            1..21
                        note = Synthetic nucleic acid
source                  1..21
                        mol_type = other DNA
                        organism = synthetic construct
SEQUENCE: 15
agcattaaag gactgactga a                                        21

SEQ ID NO: 16           moltype = DNA  length = 21
FEATURE                 Location/Qualifiers
misc_feature            1..21
                        note = Synthetic nucleic acid
source                  1..21
                        mol_type = other DNA
                        organism = synthetic construct
SEQUENCE: 16
gactgaaggc ctgcatggat t                                        21

SEQ ID NO: 17           moltype = DNA  length = 21
FEATURE                 Location/Qualifiers
misc_feature            1..21
                        note = Synthetic nucleic acid
source                  1..21
                        mol_type = other DNA
                        organism = synthetic construct
SEQUENCE: 17
ctgcatggat tccatgttca t                                        21

SEQ ID NO: 18           moltype = DNA  length = 1957
FEATURE                 Location/Qualifiers
source                  1..1957
                        mol_type = genomic DNA
                        organism = Homo sapiens
SEQUENCE: 18
acgtaaccta cggtgtcccg ctaggaaaga gaggtgcgtc aaacagcgac aagttccgcc  60
cacgtaaaag atgacgcttg atatctccgg agcatttgga taatgtgaca gttggaatgc  120
```

-continued

```
agtgatgtcg actctttgcc caccgccatc tccagctgtt gccaagacag agattgcttt    180
aagtggcaaa tcacctttat tagcagctac ttttgcttac tgggacaata ttcttggtcc    240
tagagtaagg cacatttggg ctccaaagac agaacaggta cttctcagtg atggagaaat    300
aacttttctt gccaaccaca ctctaaatgg agaaatcctt cgaaatgcag agagtggtgc    360
tatagatgta aagtttttg tcttgtctga aaagggagtg attattgttt cattaatctt    420
tgatggaaac tggaatgggg atcgcagcac atatggacta tcaattatac ttccacagac    480
agaacttagt ttctacctcc cacttcatag agtgtgtgtt gatagattaa cacatataat    540
ccggaaagga agaatatgga tgcataagga aagacaagaa aatgtccaga agattatctt    600
agaaggcaca gagagaatgg aagatcaggg tcagagtatt attccaatgc ttactggaga    660
agtgattcct gtaatggaac tgctttcatc tatgaaatca cacagtgttc ctgaagaaat    720
agatatagct gatacagtac tcaatgatga tgatattggt gacagctgtc atgaaggctt    780
tcttctcaag taagaatttt tctttttcata aaagctggat gaagcagata ccatcttatg    840
ctcacctatg acaagatttg gaagaaagaa aataacagac tgtctactta gattgttcta    900
gggacattac gtatttgaac tgttgcttaa atttgtgtta tttttcactc attatatttc    960
tatatatatt tggtgttatt ccatttgcta tttaaagaaa ccgagtttcc atcccagaca    1020
agaaatcatg gccccttgct tgattctggt ttcttgtttt acttctcatt aaagctaaca    1080
gaatcctttc atattaagtt gtactgtaga tgaacttaag ttatttaggc gtagaacaaa    1140
attattcata tttatactga tctttttcca tccagcagtg gagtttagta cttaagagtt    1200
tgtgcccta aaccagactc cctggattaa tgctgtgtac ccgtgggcaa ggtgcctgaa    1260
ttctctatac acctatttcc tcatctgtaa aatggcaata atagtaatag tacctaatgt    1320
gtagggttgt tataagcatt gagtaagata aataatataa agcacttaga acagtgcctg    1380
gaacataaaa acacttaata atagctcata gctaacattc cctatttaca tttcttctag    1440
aaatagccag tatttgttga gtgcctacat gttagttcct ttactagttg ctttacatgt    1500
attatcttat attctgtttt aaagtttctt cacagttaca gattttcatg aaatttttact    1560
tttaataaaa gagaagtaaa agtataaagt attcactttt atgttcacag tctttttcctt    1620
taggctcatg atggagtatc agaggcatga gtgtgtttaa cctaagagcc ttaatggctt    1680
gaatcagaag cactttagtc ctgtatctgt tcagtgtcag cctttcatac atcattttaa    1740
atcccatttg actttaagta agtcacttaa tctctctaca tgtcaatttc ttcagctata    1800
aaatgatggt atttcaataa ataaatacat taattaaatg atattatact gactaattgg    1860
gctgttttaa ggctcaataa gaaaatttct gtgaaaggtc tctagaaaat gtaggttcct    1920
atacaaataa aagataacat tgtgcttata aaaaaaa                             1957
```

SEQ ID NO: 19            moltype = DNA   length = 3244
FEATURE                  Location/Qualifiers
source                   1..3244
                         mol_type = genomic DNA
                         organism = Homo sapiens SEQUENCE: 19
```
gggcggggct gcggttgcgg tgcctgcgcc cgcggcggcg gaggcgcagg cggtggcgag    60
tggatatctc cggagcattt ggataatgtg acagttggaa tgcagtgatg tcgactcttt    120
gcccaccgcc atctccagct gttgccaaga cagagattgc tttaagtggc aaatcacctt    180
tattagcagc tacttttgct tactgggaca atattcttgg tcctagagta aggcacattt    240
gggctccaaa gacagaacag gtacttctca gtgatggaaa tcaactttt cttgccaacc    300
acactctaaa tggagaaatc cttcgaaatg cagagagtgg tgctatagat gtaaagtttt    360
ttgtcttgtc tgaaaaggga gtgattattg tttcattaat ctttgatgga aactggaatg    420
gggatcgcag cacatatgga ctatcaatta tacttccaca gacagaactt agtttctacc    480
tcccacttca tagagtgtgt gttgatagat taacacatat aatccggaaa ggaagaaat    540
ggatgcataa ggaaagacaa gaaaatgtcc agaagattat cttagaaggc acagagagaa    600
tggaagatca gggtcagagt attattccaa tgcttactgg agaagtgatt cctgtaatgg    660
aactgctttc atctatgaaa tcacacagtg ttcctgaaga aatagatata gctgatacag    720
tactcaatga tgatgatatt ggtgacagct gtcatgaagg ctttcttctc aatgccatca    780
gctcacactt gcaaacctgt ggctgttccg ttgtagtagg tagcagtgca gagaaagtaa    840
ataagatagt cagaacatta tgccttttc tgactccagc agagagaaaa tgctccaggt    900
tatgtgaagc agaatcatca tttaaatatg agtcagggct ctttgtacaa ggcctgctaa    960
aggattcaac tggaagcttt gtgctgcctt tccggcaagt catgtatgct ccatatccca    1020
ccacacacat agatgtggat gtcaatactg tgaagcagat gccaccctgt catgaacata    1080
tttataatca gcgtagatac atgagatccg agctgacagc cttctggaga gccacttcag    1140
aagaagacat ggctcaggat acgatcatct cactgacga aagctttact cctgatttga    1200
atattttca agatgtctta cacagagaca ctctagtgaa agcttcctg gatcaggtct    1260
ttcagctgaa acctggctta tctctcagaa gtactttcct tgcacagttt ctacttgtcc    1320
ttcacagaaa agccttgaca ctaataaaat atatagaaga cgatacgcag aagggaaaaa    1380
agccctttaa atctcttcgg aacctgaaga tagaccttga tttaacagca gagggcgatc    1440
ttaacataat aatggctctg gctgagaaaa ttaaaccagg cctacactct tttatctttg    1500
gaagaccttt ctacactagt gtgcaagaac gagatgttct aatgactttt taaatgtgta    1560
acttaataag cctattccat cacaatcatg atcgctggta aagtagctca gtggtgtggg    1620
gaaacgttcc cctggatcat actccagaat tctgctctca gcaattgcag ttaagtaagt    1680
tacactacag ttctcacaag agcctgtgag gggatgtcag gtgcatcatt acattgggtg    1740
tctctttttcc tagatttatg cttttgggat acagacctat gtttacaata taataaaat    1800
tattgctatc ttttaaagat ataataatag gatgtaaact tgaccacaac tactgttttt    1860
ttgaaataca tgattcatgg tttacatgtg tcaaggtgaa atctgagttg gcttttacag    1920
atagttgact ttctatcttt tggcattctt tggtgtgtag aattactgta atacttctgc    1980
aatcaactga aaactagagc ctttaaatga tttcaattcc acagaagaa agtgagcttg    2040
aacataggat gagctttaga aagaaaattg atcaagcaga tgtttaattg gaattgatta    2100
ttagatccta ctttgtggat ttagtccctg ggattcagtc gtagaaatg tctaatagtt    2160
ctctatagtc cttgttcctg gtgaaccaca gttagggtgt tttgtttatt ttattgttct    2220
tgctattgtt gatattctat gtagttgagc tctgtaaaag gaaattgtat tttatgtttt    2280
agtaattgtt gccaactttt taaattaatt ttcattattt ttgagccaaa ttgaaatgtg    2340
cacctcctgt gccttttttc tccttagaaa atctaattac ttggaacaag ttcagatttc    2400
actggtcagt cattttcatc ttgttttctt cttgctaagt cttaccatgt acctgctttg    2460
```

```
gcaatcattg caactctgag attataaaat gccttagaga atatactaac taataagatc  2520
ttttttttcag aaacagaaaa tagttccttg agtacttcct tcttgcattt ctgcctatgt  2580
ttttgaagtt gttgctgttt gcctgcaata ggctataagg aatagcagga gaaattttac  2640
tgaagtgctg ttttcctagg tgctactttg gcagagctaa gttatctttt gttttcttaa  2700
tgcgtttgga ccattttgct ggctataaaa taactgatta atataattct aacacaatgt  2760
tgacattgta gttacacaaa cacaaataaa tattttattt aaaattctgg aagtaatata  2820
aaagggaaaa tatatttata agaaagggat aaaggtaata gagcccttct gcccccccacc  2880
caccaaattt acacaacaaa atgacatgtt cgaatgtgaa aggtcataat agctttccca  2940
tcatgaatca gaaagatgtg gacagcttga tgttttagac aaccactgaa ctagatgact  3000
gttgtactgt agctcagtca tttaaaaaat atataaatac taccttgtag tgtcccatac  3060
tgtgttttttt acatggtaga ttcttatttta agtgctaact ggttattttc tttggctggt  3120
ttattgtact gttatacaga atgtaagttg tacagtgaaa taagttatta aagcatgtgt  3180
aaacattgtt atatatcttt tctccctaaat ggagaatttt gaataaaata tatttgaaat  3240
tttg                                                                3244
```

```
SEQ ID NO: 20          moltype = DNA  length = 3339
FEATURE                Location/Qualifiers
source                 1..3339
                       mol_type = genomic DNA
                       organism = Homo sapiens
SEQUENCE: 20
acgtaaccta cggtgtcccg ctaggaaaga gaggtgcgtc aaacagcgac aagttccgcc  60
cacgtaaaag atgacgcttg gtgtgtcagc cgtccctgct gcccggttgc ttctcttttg  120
ggggcggggt ctagcaagag caggtgtggg tttaggagat atctccggag catttggata  180
atgtgacagt tggaatgcag tgatgtcgac tctttgccca ccgccatctc cagctgttgc  240
caagacagag attgctttaa gtggcaaatc acctttatta gcagctactt ttgcttactg  300
ggacaatatt cttggtccta gagtaaggca catttgggct ccaaagacag aacaggtact  360
tctcagtgat ggagaaataa cttttcttgc caaccacact ctaaatggag aaatccttcg  420
aaatgcagag agtggtgcta tagatgtaaa gtttttttgtc ttgtctgaaa agggagtgat  480
tattgtttca ttaatctttg atggaaactg gaatggggat cgcagcacat atggactatc  540
aattatactt ccacagacag aacttagttt ctacctccca cttcatagag tgtgtgttga  600
tagattaaca catataatcc ggaaaggaag aatatggatg cataaggaaa gacaagaaaa  660
tgtccagaag attatcttag aaggcacaga gagaatggaa gatcagggtc agagtattat  720
tccaatgctt actggagaag tgattcctgt aatggaactg ctttcatcta tgaaatcaca  780
cagtgttcct gaagaaatag atatagctga tacagtactc aatgatgatg atattggtga  840
cagctgtcat gaaggctttc ttctcaatgc catcagctca cacttgcaaa cctgtggctg  900
ttccgttgta gtaggtagca gtgcagagaa agtaaataag atagtcagaa cattatgcct  960
ttttctgact ccagcagaga gaaaatgctc caggttatgt gaagcagaat catcatttaa  1020
atatgagtca gggctctttg tacaaggcct gctaaaggat tcaactggaa gcttttgtgct  1080
gcctttccgg caagtcatgt atgctccata tcccaccaca cacatagatg tggatgtcaa  1140
tactgtgaag cagatgccac cctgtcatga acatatttat aatcagcgta gatacatgag  1200
atccgagctg acagccttct ggagagccac ttcagaagaa gacatggctc aggatacgat  1260
catctacact gacgaaagct ttactcctga tttgaatatt tttcaagatg tcttacacag  1320
agacactcta gtgaaagcct tcctggatca ggtctttcag ctgaaacctg gcttatctct  1380
cagaagtact ttccttgcac agtttctact tgtccttcac agaaaagcct tgacactaat  1440
aaaatatata gaagacgata cgcagaaggg aaaaaagccc tttaaatctc ttcggaacct  1500
gaagatagac cttgatttaa cagcagaggg cgatcttaac ataataatgg ctctggctga  1560
gaaaattaaa ccaggcctac actctttat ctttggaaga cctttctaca ctagtgtgca  1620
agaacgagat gttctaatga ctttttaaat gtgtaactta ataagcctat tccatcacaa  1680
tcatgatcgc tggtaaagta gctcagtggt gtggggaaac gttccctgg atcatactcc  1740
agaattctgc tctcagcaat tgcagttaag taagttacac tacagttctc acaagagcct  1800
gtgaggggat gtcaggtgca tcattacatt gggtgtctct tttcctagat ttatgctttt  1860
gggatacaga cctatgttta caatataata aatattattg ctatctttta aagatataat  1920
aataggatgt aaacttgacc acaactactg ttttttttgaa atacatgatt catggtttac  1980
atgtgtcaag gtgaaatctg agttggcttt tacagatagt tgactttcta tcttttggca  2040
ttctttggtg tgtagaatta ctgtaatact tctgcaatca actgaaaact agagccttta  2100
aatgatttca attccacaga aagaaagtga gcttgaacat aggatgagct ttagaaagaa  2160
aattgatcaa gcagatgttt aattggaatt gattattaga tcctactttg tggatttagt  2220
ccctgggatt cagtctgtag aaatgtctaa tagttctcta tagtccttgt tcctggtgaa  2280
ccacagttag ggtgtttttgt ttattttatt gttcttgcta ttgttgatat tctatgtagt  2340
tgagctctgt aaaaggaaat tgtatttttat gtttttagtaa ttgttgccaa cttttttaaat  2400
taatttttcat tattttttgag ccaaattgaa atgtgcacct cctgtgcctt ttttctcctt  2460
agaaaatcta attacttgga acaagttcag atttcactgg tcagtcattt tcatcttgtt  2520
ttcttcttgc taagtcttac catgtacctg ctttggcaat cattgcaact ctgagattat  2580
aaaatgcctt agagaatata ctaactaata agatctttt ttcagaaaca gaaaatagtt  2640
ccttgagtac ttccttcttg catttctgcc tatgtttttg aagttgttgc tgtttgcctg  2700
caataggcta taggaatag caggagaaat tttactgaag tgctgttttc ctaggtgcta  2760
ctttggcaga gctaagttat ctttgttttc ttaatgatttca attccacaga aagaaagtga  2820
taaataact gattaatata attctaacac aatgttgaca ttgtagttac acaaacacaa  2880
ataaatattt tatttaaaat ctggaagta atataaaagg gaaaatatat ttataagaaa  2940
gggataaagg taatagagcc cttctgcccc ccacccacca aatttacaca acaaaatgac  3000
atgttcgaat gtgaaaggtc ataatagctt tcccatcatg aatcagaaag atgtggacag  3060
cttgatgttt tagacaacca ctgaactaga tgactgttgt actgtagctc agtcatttaa  3120
aaaatatata aatactacct tgtagtgtcc catactgtgt ttattt gtactgttat acagaatgta  3180
atttaagtgc taactggtta ttttctttgg ctggtttatt gtactgttat acagaatgta  3240
agttgtacag tgaaataagt tattaaagca tgtgtaaaca ttgttatata tcttttctcc  3300
taaatggaga attttgaata aaatatattt gaatttttg                          3339
```

```
SEQ ID NO: 21          moltype = RNA  length = 65
```

-continued

```
FEATURE              Location/Qualifiers
misc_feature         1..65
                     note = Synthetic
source               1..65
                     mol_type = other RNA
                     organism = synthetic construct
SEQUENCE: 21
ctgatgaaca tggaatccat gcaggttttg gccactgact gacctgcatg gtccatgttc  60
atcag                                                              65

SEQ ID NO: 22        moltype = DNA  length = 465
FEATURE              Location/Qualifiers
source               1..465
                     mol_type = genomic DNA
                     organism = Homo sapiens
SEQUENCE: 22
atggcgacga aggccgtgtg cgtgctgaag ggcgacggcc cagtgcaggg catcatcaat  60
ttcgagcaga aggaaagtaa tggaccagtg aaggtgtggg gaagcattaa aggactgact  120
gaaggcctgc atggattcca tgttcatgag tttggagata atacagcagg ctgtaccagt  180
gcaggtcctc actttaatcc tctatccaga aaacacggtg ggccaaagga tgaagagagg  240
catgttggag acttgggcaa tgtgactgct gacaaagatg gtgtggccga tgtgtctatt  300
gaagattctg tgatctcact ctcaggagac cattgcatca ttggccgcac actggtggtc  360
catgaaaaag cagatgactt gggcaaaggt ggaaatgaag aaagtacaaa gacaggaaac  420
gctggaagtc gtttggcttg tggtgtaatt gggatcgccc aataa                 465

SEQ ID NO: 23        moltype = DNA  length = 465
FEATURE              Location/Qualifiers
source               1..465
                     mol_type = genomic DNA
                     organism = Macaca mulatta
SEQUENCE: 23
atggcgatga aggccgtgtg cgtgttgaag ggcgacagcc cagtgcaggg caccatcaat  60
ttcgagcaga aggaaagtaa tggaccagtg aaggtgtggg gaagcattac aggattgact  120
gaaggcctgc atggattcca tgttcatgag tttggagata atacagcagg ctgtaccagt  180
gcaggtcctc actttaatcc tctatccaga aaacacggtg ggccaaagga tgaagagagg  240
catgttggag acttgggcaa tgtgactgct gacaaagatg gtgtggccaa ggtgtctttc  300
gaagattctg tgatctcgct ctcaggagac cattccatca ttggccgcac attggtggtc  360
catgaaaaag cagatgactt gggcaaaggt ggaaatgaag aaagtaaaaa gacaggaaac  420
gctggaggtc gtctggcttg tggtgtaatt gggatcgccc aataa                 465

SEQ ID NO: 24        moltype = DNA  length = 465
FEATURE              Location/Qualifiers
source               1..465
                     mol_type = genomic DNA
                     organism = Callithrix jacchus
SEQUENCE: 24
atggcgatga aggcggtgtg cgtgttgaag ggcgacggcc cggtgcaggg caccatcaat  60
ttcgagcaga aggaaagtaa tggaccagtt aaggtgtggg gaagcattac aggattggct  120
gaaggcctgc atggattcca tgttcatcag tttggagaca acacacaagg ctgtaccagt  180
gcaggtcctc actttaatcc tctatccaga aaacatggtg ggccagagga tgaagagagg  240
catgttggag acctgggcaa tgtgactgct ggtaaagatg gtgtggccag tgtgtcaatt  300
gaagattctg tgatctcact ctcaggagtc cattccatca ttggccgcac gttggtggtc  360
catgaaaaag cagatgactt gggcaaaggt ggaaatgaag aaagtacaaa gacaggaaac  420
gctggaagtc gtttggcttg tggtgtcatt gggatcgccc agtaa                 465

SEQ ID NO: 25        moltype = RNA  length = 19
FEATURE              Location/Qualifiers
source               1..19
                     mol_type = other RNA
                     organism = synthetic construct
SEQUENCE: 25
gttttggcca ctgactgac                                               19
```